US012398117B2

(12) United States Patent
Jeong et al.

(10) Patent No.: US 12,398,117 B2
(45) Date of Patent: Aug. 26, 2025

(54) HETEROARYLAMIDOPYRIDINOL DERIVATIVE AND PHARMACEUTICAL COMPOSITION COMPRISING SAME AS ACTIVE INGREDIENT FOR PREVENTION OR TREATMENT OF AUTOIMMUNE DISEASE

(71) Applicant: INNOVO THERAPEUTICS INC., Seoul (KR)

(72) Inventors: Byeong-Seon Jeong, Seoul (KR); Jung-Ae Kim, Seoul (KR); Tae-gyu Nam, Seoul (KR)

(73) Assignee: Innovo Therapeutics Inc., Seoul (KR)

( * ) Notice: Subject to any disclaimer, the term of this patent is extended or adjusted under 35 U.S.C. 154(b) by 843 days.

(21) Appl. No.: 17/639,886

(22) PCT Filed: Sep. 24, 2020

(86) PCT No.: PCT/KR2020/013003
§ 371 (c)(1),
(2) Date: Mar. 2, 2022

(87) PCT Pub. No.: WO2021/060890
PCT Pub. Date: Apr. 1, 2021

(65) Prior Publication Data
US 2022/0324834 A1    Oct. 13, 2022

(30) Foreign Application Priority Data
Sep. 24, 2019    (KR) .................. 10-2019-0117253

(51) Int. Cl.
*A61P 1/00*    (2006.01)
*A61P 19/02*    (2006.01)
(Continued)

(52) U.S. Cl.
CPC .............. *C07D 401/12* (2013.01); *A61P 1/00* (2018.01); *A61P 19/02* (2018.01); *C07D 405/12* (2013.01); *C07D 409/12* (2013.01)

(58) Field of Classification Search
CPC .. C07D 401/12; C07D 405/12; C07D 409/12; C07D 409/14; C07D 333/70; A61P 1/00;
(Continued)

(56) References Cited

U.S. PATENT DOCUMENTS

2015/0322012 A1    11/2015   Whitten et al.

FOREIGN PATENT DOCUMENTS

EP              2987786 A1    2/2016
JP           2012107001 A     6/2012
(Continued)

OTHER PUBLICATIONS

Barnett et al., "Treatment of Rheumatoid Arthritis with Oral Type II Collagen," *Arthritis & Rheumatism* 41.2: 290-297, Feb. 1998.
(Continued)

*Primary Examiner* — Taylor V Oh
(74) *Attorney, Agent, or Firm* — Klarquist Sparkman, LLP

(57) ABSTRACT

The present invention relates to a heteroarylamidopyridinol derivative and a pharmaceutical composition comprising same as an active ingredient for prevention or treatment of an autoimmune disease, specifically, inflammatory bowel disease, rheumatoid arthritis, etc. The heteroarylamidopyridinol derivative exhibits an excellent effect of inhibiting TNF-α- or IL-6-induced monocyte adhesion to gut epithelial cells and is proven to have a therapeutic effect on inflammatory bowel disease and rheumatoid arthritis in vivo. Thus, the heteroarylamidopyridinol derivative can be advantageously used for treatment of an autoimmune disease, specifically, inflammatory bowel disease or rheumatoid arthritis.

11 Claims, 18 Drawing Sheets

(51) Int. Cl.
*C07D 401/12* (2006.01)
*C07D 405/12* (2006.01)
*C07D 409/12* (2006.01)

(58) Field of Classification Search
CPC .. A61P 19/02; A61P 7/06; A61P 29/00; A61P 37/00; A61P 1/04; A61P 1/12; A61P 1/16; A61P 3/10; A61P 13/12; A61P 17/00; A61P 17/06; A61P 17/14; A61P 21/04; A61P 25/28; A61P 27/02; A61P 37/06; A23L 33/10; A23V 2002/00; A61K 31/443; A61K 31/4439
USPC .......................................................... 514/343
See application file for complete search history.

(56) References Cited

FOREIGN PATENT DOCUMENTS

| | | |
|---|---|---|
| KR | 20140125738 A | 10/2014 |
| KR | 101600613 B1 | 3/2016 |
| KR | 101663864 | 10/2016 |
| KR | 101770310 | 8/2017 |
| WO | WO 2004/076412 A2 | 9/2004 |
| WO | WO 2007/022380 A2 | 2/2007 |
| WO | WO 2014/186035 A1 | 11/2014 |
| WO | WO 2016/089060 A2 | 6/2016 |
| WO | WO 2018/131924 A1 | 7/2018 |
| WO | WO 2019/087129 A1 | 5/2019 |

OTHER PUBLICATIONS

Carvalho et al., "IgG Antiendothelial Cell Autoantibodies from Scleroderma Patients Induce Leukocyte Adhesion to Human Vascular Endothelial Cells In Vitro: Induction of Adhesion Molecule Expression and Involvement of Endothelium-derived Cytokines,," *J Clin Invest.* 97.1: 111-119, Jan. 1996.

International Search Report and Written Opinion from the Korean Search Authority of the Korean Intellectual Property Office, in PCT/KR2020/013003, mailed on Jan. 4, 2021, 11 pages (with English translation of the International Search Report, 4 pages).

Thapa et al., "Clotrimazole Ameliorates Intestinal Inflammation and Abnormal Angiogenesis by Inhibiting Interleukin-8 Expression through a Nuclear Factor-κB-Dependent Manner," *The Journal of Pharmacology and Experimental Therapeutics* 327.2: 353-364, 2008.

Staining of knee joints tissue

*** $P<0.001$ vs vehicle-control
$P<0.05$ vs tofacitinib 50 mg/kg

HETEROARYLAMIDOPYRIDINOL DERIVATIVE AND PHARMACEUTICAL COMPOSITION COMPRISING SAME AS ACTIVE INGREDIENT FOR PREVENTION OR TREATMENT OF AUTOIMMUNE DISEASE

CROSS REFERENCE TO RELATED APPLICATIONS

This is the U.S. National Stage of International Application No. PCT/KR2020/013003, filed Sep. 24, 2020, which in turn claims the benefit of priority under 35 U.S.C. § 119 from Korean Patent Application No. 10-2019-0117253, filed Sep. 24, 2019. The Korean patent application is incorporated herein by reference in its entirety.

BACKGROUND OF THE INVENTION

1. Field of the Invention

The present invention relates to a heteroarylamidopyridinol derivative and a pharmaceutical composition comprising the same as an active ingredient for the prevention or treatment of autoimmune diseases such as inflammatory bowel disease and rheumatoid arthritis.

2. Description of the Related Art

Immunity is one of the self-protection systems of a living body against all the foreign polymers that invade or are injected into the living tissues. All normal individuals do not react detrimentally to antigens constituting the self, whereas they have the ability to recognize and react to non-self antigens and remove them. However, if the host's immune system fails to distinguish foreign antigens from self-antigens and induces an abnormal immune response, the immune cells in the body attack their own cellular components and cause various diseases, which are called autoimmune diseases.

Autoimmune disease is caused by a variety of causes, such as heredity, stress, hormones, heavy metals, food, infection, and pesticides, and occurs in about 5 to 8% of the world's population. Examples of autoimmune diseases include inflammatory bowel disease, autism, asthma, type 1 diabetes, rheumatoid arthritis, polymyalgia rheumatica, ankylosing spondylitis, psoriatic arthritis, psoriasis, eczema, scleroderma, vitiligo, multiple sclerosis, IL-17-induced dementia, peripheral neuritis, uveitis, dry eye syndrome, organ transplantation rejection, and cancer. Currently, anti-inflammatory and immunosuppressive drugs are used as therapeutic agents for autoimmune disease, but some patients are resistant to these drugs, making treatment difficult.

Among the autoimmune diseases, inflammatory bowel disease is an inflammatory disease of the digestive tract with a chronic and recurrent course, and is classified into two diseases: ulcerative colitis and Crohn's disease. The exact cause of the disease is not yet known, but it is caused by an inappropriate immune response to bacteria in the intestinal tract in a person with a genetic predisposition. Continuous or inappropriate activation of the enteric immune system, such as neutrophils and macrophages, which are innate immune cells, as well as lymphocytes, which are acquired immune cells, eventually leads to mucosal destruction and ulceration. Various inflammatory cytokines are produced and secreted in the mucous membrane of the intestinal tract in an inflamed state, and among them, TNF-α (tumor necrosis factor-α) is highly expressed in the intestinal lumen and epithelial cells of ulcerative colitis patients. According to recent studies, TNF-α is known to play an important role in the pathogenesis of ulcerative colitis.

Infliximab, an anti-TNF-α antibody, is known to be effective not only in the treatment of furuncles, but also in the treatment of Crohn's disease previously untreated. However, such treatment is expensive and causes side effects such as fluid reactions or infectious complications in some patients. Tofacitinib (Xeljanz®), a Janus kinase (JAK) inhibitor, has been confirmed to have therapeutic efficacy in ulcerative colitis, but has been confirmed to be ineffective in Crohn's disease. In other words, there are still no reliable oral treatment agents for inflammatory bowel disease, so there is a need to develop an effective and low-cost oral treatment for the disease.

Among the autoimmune diseases, rheumatoid arthritis is a disease that is common enough to account for about 1% of the adult population, and is a disease that results in joint destruction and joint deformity in most patients, eventually resulting in disability. In the pathophysiology of rheumatoid arthritis, the disease is reported to occur by the activation of autoreactive T cells specific to neopeptides made by the antigens in the joint such as collagen or proteoglycan due to chronic inflammation after an inflammatory response according to viral or bacterial infection. The correlation between rheumatoid arthritis and T lymphocytes as well as B lymphocytes and synovial cells is well known. Important cytokines associated with rheumatoid arthritis are TNF-α, IL-1, and IL-6. They increase the expression of adhesion molecules in endothelial cells to increase the influx of leukocytes into the joint, and promote the secretion of matrix metalloproteinase in synovial cells and chondrocytes to induce tissue destruction. Among the newly developed drugs for the treatment of rheumatoid arthritis, anti-TNF-α antibody preparations are the most representative, and among them, etanercept (Enbrel®), infliximab (Remicade®), and adalimumab (Humira®) are the most commonly used drugs.

However, these drugs are expensive and the inconvenience of administration is an obstacle in treatment. In the case of tofacitinib, which was recently developed as a treatment for rheumatoid arthritis that can be administered orally, diverticulitis was reported as a 'serious' infection in a series of clinical trials targeting rheumatoid arthritis patients. In particular, as diverticulum perforation, one of the cases of gastrointestinal perforation, was reported in clinical trials, both the 'caution' and 'adverse reactions' sections were updated by the FDA in December 2015. To date, there is no development of a safe and effective oral therapeutic agent as a drug targeting TNF-α or TNF receptor, which has emerged as the most effective therapeutic target for rheumatoid arthritis. Therefore, there is a request for the development of an effective, low-cost, safe, and highly effective oral rheumatoid arthritis therapeutic agent targeting the same.

T cells, which play a central role in the immune system, a biological defense system against various pathogens, exist as various types of differentiated cells. Th1 cells are involved in cell-mediated immunity, Th2 cells are involved in humoral immunity, Th17 cells are involved in infectious and inflammatory diseases, and Treg cells are responsible for maintaining homeostasis by suppressing immunity. However, it is known that autoimmune disease occurs when the activities of Th1 cells and Th17 cells are abnormally increased, and immune disease occurs when the activity of Th2 cells is abnormally increased due to hypersensitivity reaction. Since Treg cells that can regulate the activity of these cells have the property of controlling the inflammatory response by suppressing the functions of abnormally activated immune cells, many experiments have been reported to treat immune diseases through the action of increasing the activity of Treg cells. In the case of autoimmune disease that is not controlled by Treg cells, the development of therapeutic agents for autoimmune disease targeting the inhibition of the activations of Th1 and Th17 cells has been highlighted. In addition to treating immune diseases by inhibiting the activation of T cells, therapies that control the amount of cytokines secreted from immune cells and therapies using antibodies targeting cytokines secreted from immune cells are being developed. However, among them, the method using antibodies has problems in that the manufacturing cost is high and administration is inconvenient. Therefore, there is a need to develop a novel low molecular weight compound immune disease treatment agent that can be administered orally with excellent therapeutic and preventive effects on various autoimmune diseases.

SUMMARY OF THE INVENTION

It is an object of the present invention to provide a heteroarylamidopyridinol derivative.

It is another object of the present invention to provide a method for preparing a heteroarylamidopyridinol derivative.

It is another object of the present invention to provide a pharmaceutical composition comprising a heteroarylamidopyridinol derivative as an active ingredient for the prevention or treatment of autoimmune disease.

To achieve the above objects, in one aspect of the present invention, the present invention provides a compound represented by formula 1, an isomer thereof, a solvate thereof, a hydrate thereof or a pharmaceutically acceptable salt thereof:

[Formula 1]

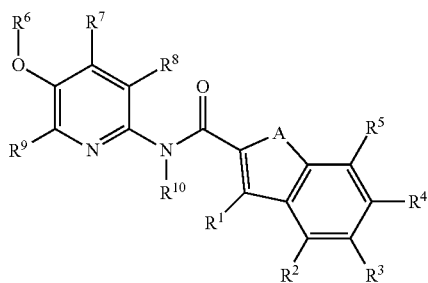

(In formula 1,

A, $R^1$, $R^2$, $R^3$, $R^4$, $R^5$, $R^6$, $R^7$, $R^8$, $R^9$, and $R^{10}$ are as defined in this specification).

In another aspect of the present invention, the present invention provides a method for preparing a compound represented by formula 1 comprising a step of preparing a compound represented by formula 1 by reacting a compound represented by formula 2 with a compound represented by formula 3, as shown in reaction formula 1 below:

[Reaction Formula 1]

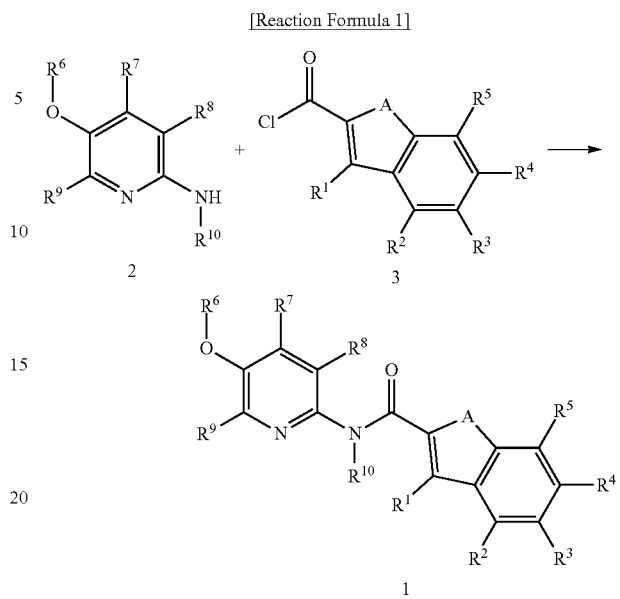

(In reaction formula 1,

A, $R^1$, $R^2$, $R^3$, $R^4$, $R^5$, $R^6$, $R^7$, $R^8$, $R^9$, and $R^{10}$ are as defined in this specification).

In another aspect of the present invention, the present invention provides a method for preparing a compound represented by formula 1 comprising the following steps, as shown in reaction formula 2 below:

preparing a compound represented by formula 4 by reacting a compound represented by formula 2a with a compound represented by formula 3 (step 1);

preparing a compound represented by formula 1a by deprotecting the compound represented by formula 4 obtained in step 1 above (step 2); and preparing a compound represented by formula 1b by reacting the compound represented by formula 1a obtained in step 2 above with a compound represented by formula 5 (step 3):

[Reaction Formula 2]

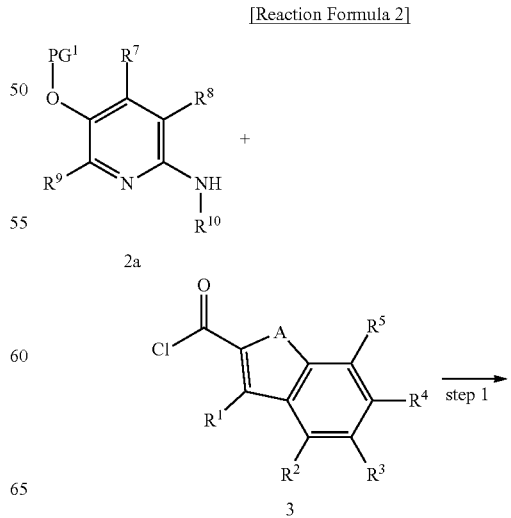

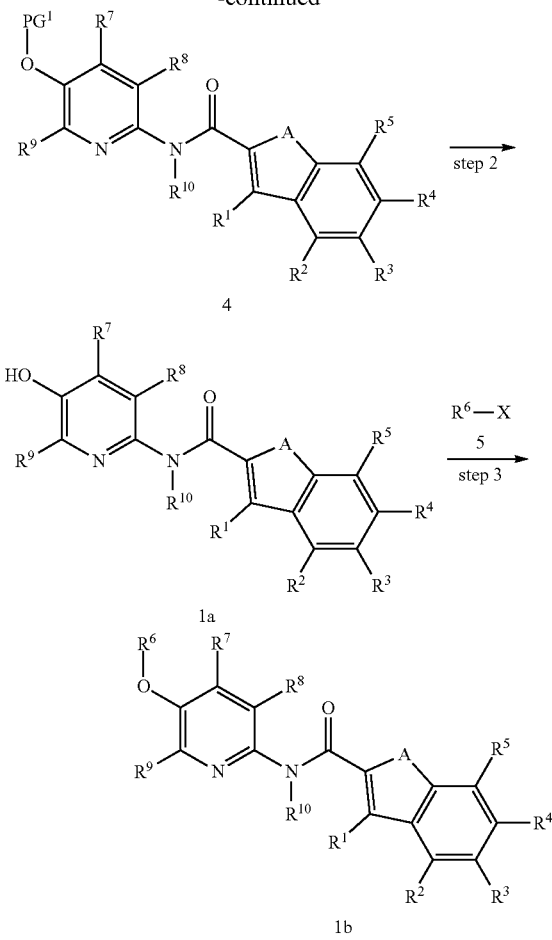

(In reaction formula 2,

A, $R^1$, $R^2$, $R^3$, $R^4$, $R^5$, $R^6$, $R^7$, $R^8$, $R^9$, and $R^{10}$ are as defined in this specification except when $R^6$ is hydrogen;

the compound represented by formula 1a is a derivative of formula 1 wherein $R^6$ is hydrogen;

the compound represented by formula 1b is a derivative of formula 1 except when $R^6$ is hydrogen;

$PG^1$ is an alcohol protecting group selected from the group consisting of acetyl (Ac), benzoyl (Bz), benzyl (Bn), methylthiomethyl ether, MEM (β-methoxyethoxymethyl ether), DMT (dimethoxytrityl, [bis-(4-methoxyphenyl)phenylmethyl]), MOM (methoxymethyl ether), MMT (methoxytrityl [(4-methoxyphenyl)diphenylmethyl]), PMP (p-methoxybenzyl ether), Piv (pivaloyl), THP (tetrahydropyranyl), THF (tetrahydrofuran) and Trityl (triphenylmethyl, Tr); and X is halogen).

In another aspect of the present invention, the present invention provides a pharmaceutical composition comprising a compound represented by formula 1, an isomer thereof, a solvate thereof, a hydrate thereof, or a pharmaceutically acceptable salt thereof as an active ingredient for the prevention or treatment of autoimmune disease.

In another aspect of the present invention, the present invention provides a health functional food comprising a compound represented by formula 1, an isomer thereof, a solvate thereof, a hydrate thereof, or a pharmaceutically acceptable salt thereof as an active ingredient for the prevention or amelioration of autoimmune disease.

In another aspect of the present invention, the present invention provides a method for preventing or treating autoimmune disease, which comprises a step of administering a pharmaceutical composition or a health functional food comprising a compound represented by formula 1, an isomer thereof, a solvate thereof, a hydrate thereof, or a pharmaceutically acceptable salt thereof as an active ingredient to a subject in need.

In another aspect of the present invention, the present invention provides a use of the pharmaceutical composition or the health functional food above comprising a compound represented by formula 1, an isomer thereof, a solvate thereof, a hydrate thereof, or a pharmaceutically acceptable salt thereof as an active ingredient for the prevention or treatment of autoimmune disease.

Advantageous Effect

The heteroarylamidopyridinol derivative of the present invention exhibits an excellent effect of inhibiting TNF-α- or IL-6-induced monocyte adhesion to gut epithelial cells and is proven to have a therapeutic effect on inflammatory bowel disease and rheumatoid arthritis in vivo. Thus, the heteroarylamidopyridinol derivative can be advantageously used for the treatment of autoimmune disease, specifically, inflammatory bowel disease or rheumatoid arthritis.

BRIEF DESCRIPTION OF THE DRAWINGS

FIG. 1A: a graph showing the degree of colon mucosa damage and recovery by scoring, FIG. 1B: images of the colon tissue stained with hematoxylin & eosin.

FIG. 4A: a graph showing the results of scoring and comparing the degree of colon mucosa damage, FIG. 4B: images of the colon tissue stained with hematoxylin & eosin after morphology observation.

FIG. 7A: hematoxylin & eosin staining and safranin O stained images, FIG. 7B: a graph showing the degree of the articular tissue recovery converted to scores.

DESCRIPTION OF THE PREFERRED EMBODIMENTS

Figure 1A:
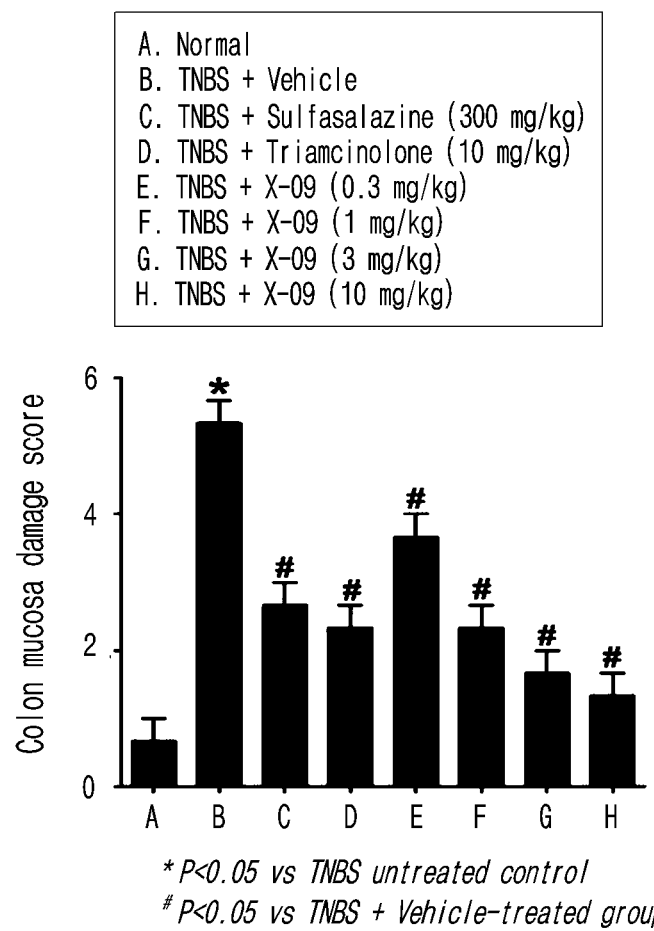
FIGS. 1A-1B are a set of diagrams showing the results of measuring the intestinal mucosal damage recovery effect according to the treatment of the compound of the present invention in a TNBS-induced inflammatory bowel disease animal model in Experimental Example 3.

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely. In addition, the "inclusion" of an element throughout the specification does not exclude other elements, but may include other elements, unless specifically stated otherwise.

In one aspect of the present invention, the present invention provides a compound represented by formula 1, an isomer thereof, a solvate thereof, a hydrate thereof or a pharmaceutically acceptable salt thereof.

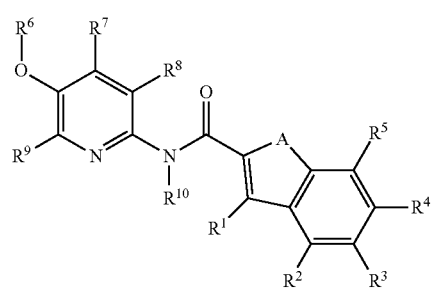

[Formula 1]

(In formula 1,

A is $NR^a$, O or S, wherein, the $R^a$ is hydrogen or straight chained or branched $C_1$ s alkyl;

$R^1$, $R^2$, $R^3$, $R^4$, and $R^5$ are independently hydrogen, halogen, straight chained or branched $C_{1-5}$ alkyl or straight chained or branched $C_{1-5}$ alkoxy, wherein the alkyl and alkoxy can be independently substituted with one or more halogens;

$R^6$ is hydrogen, straight chained or branched $C_{1-5}$ alkyl, $-(CH_2)mC(=O)NH(CH_2)nR^b$ or $-C(=O)R^c$, wherein the alkyl can be substituted with one or more halogens, and m and n are independently integers of 0 to 5, $R^b$ is hydrogen, straight chained or branched $C_{1-10}$ alkyl, $C_{3-10}$ cycloalkyl or $C_{6-10}$ aryl, $R^c$ is adamantanyl

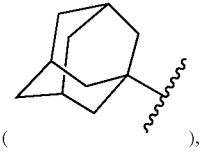

( ), 3-10 membered heterocycloalkyl containing one or more hetero atoms selected from the group consisting of N, O and S, $C_{6-10}$ aryl, or 5-10 membered heteroaryl containing one or more hetero atoms selected from the group consisting of N, O and S, wherein the aryl and heteroaryl can be independently substituted with at least one selected from the group consisting of halogen, straight chained or branched $C_{1-5}$ alkyl and straight chained or branched $C_{1-5}$ alkoxy;

$R^7$, $R^8$, and $R^9$ are independently straight chained or branched $C_{1-5}$ alkyl; and $R^{10}$ is hydrogen or straight chained or branched $C_{1-5}$ alkyl).

In formula 1 above, A is $NR^a$, O or S, wherein the $R^a$ is hydrogen or straight chained or branched $C_{1-3}$ alkyl;

$R^1$, $R^2$, $R^3$, $R^4$, and $R^5$ are independently hydrogen, halogen, straight chained or branched $C_{1-3}$ alkyl, or straight chained or branched $C_{1-3}$ alkoxy, wherein the alkyl and alkoxy can be independently substituted with one or more halogens;

$R^6$ is hydrogen, straight chained or branched $C_{1-3}$ alkyl, $-(CH_2)mC(=O)NH(CH_2)nR^b$, or $-C(=O)R^c$, wherein the alkyl can be substituted with one or more halogens, and m and n are independently integers of 0 to 3, $R^b$ is hydrogen, straight chained or branched $C_{1-6}$ alkyl, $C_{3-8}$ cycloalkyl or phenyl, $R^c$ is adamantanyl

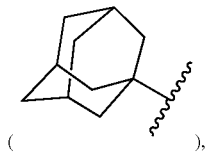 [SMILES: *C12CC3CC(CC(C3)C1)C2]

( ), 3-8 membered heterocycloalkyl containing one or more hetero atoms selected from the group consisting of N, O and S, phenyl, or 5-6 membered heteroaryl containing one or more hetero atoms selected from the group consisting of N, O and S, wherein the phenyl and heteroaryl can be independently substituted with at least one selected from the group consisting of halogen, straight chained or branched $C_{1-3}$ alkyl and straight chained or branched $C_{1-3}$ alkoxy;

$R^7$, $R^8$, and $R^9$ are independently straight chained or branched $C_{1-3}$ alkyl; and $R^{10}$ is hydrogen or straight chained or branched $C_{1-3}$ alkyl.

In formula 1 above, A is $NR^a$, O or S, wherein the $R^a$ is hydrogen or methyl;

$R^1$, $R^2$, $R^3$, $R^4$, and $R^5$ are independently hydrogen, —Cl, —Br, —F, methyl, methoxy, —$CF_3$ or —$OCF_3$;

$R^6$ is hydrogen, methyl, —$(CH_2)mC(=O)NH(CH_2)nR^b$, or —$C(=O)R^c$, wherein m is 1, and n is 0 or 1, $R^b$ is hydrogen, straight chained or branched $C_{1-3}$ alkyl, $C_{3-6}$ cycloalkyl or phenyl, $R^c$ is adamantanyl

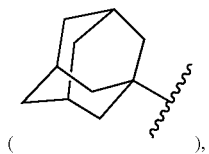 [SMILES: *C12CC3CC(CC(C3)C1)C2]

( ), 6 membered heterocycloalkyl containing one or more hetero atoms selected from the group consisting of N, O and S, phenyl, or 6 membered heteroaryl containing one or more hetero atoms selected from the group consisting of N, O and S, wherein the phenyl and heteroaryl can be independently substituted with at least one selected from the group consisting of halogen, and straight chained or branched $C_{1-3}$ alkoxy;

$R^7$, $R^8$, and $R^9$ are methyl; and $R^{10}$ is hydrogen or methyl.

In formula 1 above, $R^6$ is hydrogen, methyl, —$(CH_2)C(=O)NHR^b$, or —$C(=O)R^c$, $R^b$ is hydrogen, isopropyl, cyclopropyl, cyclohexyl, phenyl or benzyl, $R^c$ is adamantanyl

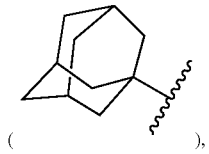 [SMILES: *C12CC3CC(CC(C3)C1)C2]

( ), morpholinyl, phenyl or pyridinyl, wherein the phenyl and pyridinyl can be independently substituted with at least one selected from the group consisting of F, Cl and methoxy.

Examples of the compound represented by formula 1 according to the present invention include the following compounds:

<1> N-(5-(benzyloxy)-3,4,6-trimethylpyridin-2-yl)-1H-indole-2-carboxamide; <2> N-(5-(benzyloxy)-3,4,6-trimethylpyridin-2-yl)-1-methyl-1H-indole-2-carboxamide; <3> N-(5-(benzyloxy)-3,4,6-trimethylpyridin-2-yl)-7-bromo-1H-indole-2-carboxamide; <4> N-(5-(benzyloxy)-3,4,6-trimethylpyridin-2-yl)-6-chloro-1H-indole-2-carboxamide; <5> N-(5-(benzyloxy)-3,4,6-trimethylpyridin-2-yl)-6-bromo-1H-indole-2-carboxamide; <6> N-(5-(benzyloxy)-3,4,6-trimethylpyridin-2-yl)-5-fluoro-1H-indole-2-carboxamide; <7> N-(5-(benzyloxy)-3,4,6-trimethylpyridin-2-yl)-5-bromo-1H-indole-2-carboxamide; <8> N-(5-(benzyloxy)-3,4,6-trimethylpyridin-2-yl)-5-chloro-1H-indole-2-carboxamide; <9> N-(5-(benzyloxy)-3,4,6-trimethylpyridin-2-yl)-5-methyl-1H-indole-2-carboxamide; <10> N-(5-(benzyloxy)-3,4,6-trimethylpyridin-2-yl)-5-(trifluoromethyl)-1H-indole-2-carboxamide; <11> N-(5-(benzyloxy)-3,4,6-trimethylpyridin-2-yl)-5-(trifluoromethoxy)-1H-indole-2-carboxamide; <12> N-(5-(benzyloxy)-3,4,6-trimethylpyridin-2-yl)-6-methoxy-1H-indole-2-carboxamide; <13> N-(5-(benzyloxy)-3,4,6-trimethylpyridin-2-yl)-5-methoxy-1H-indole-2-carboxamide; <14> N-(5-(benzyloxy)-3,4,6-trimethylpyridin-2-yl)-5,6-dimethoxy-1H-indole-2-carboxamide; <15> N-(5-(benzyloxy)-3,4,6-trimethylpyridin-2-yl)benzofuran-2-carboxamide; <16> N-(5-(benzyloxy)-3,4,6-trimethylpyridin-2-yl)-5-chlorobenzofuran-2-carboxamide; <17> N-(5-(benzyloxy)-3,4,6-trimethylpyridin-2-yl)-5-bromobenzofuran-2-carboxamide; <18> N-(5-(benzyloxy)-3,4,6-trimethylpyridin-2-yl)-7-methoxybenzofuran-2-carboxamide; <19> N-(5-(benzyloxy)-3,4,6-trimethylpyridin-2-yl)-3-methylbenzofuran-2-carboxamide; <20> N-(5-(benzyloxy)-3,4,6-trimethylpyridin-2-yl)benzo[b]thiophene-2-carboxamide; <21> N-(5-(benzyloxy)-3,4,6-trimethylpyridin-2-yl)-3-chlorobenzo[b]thiophene-2-carboxamide; <22> N-(5-(benzyloxy)-3,4,6-trimethylpyridin-2-yl)-3-bromobenzo[b]thiophene-2-carboxamide; <23> N-(5-(benzyloxy)-3,4,6-trimethylpyridin-2-yl)-3-chloro-6-methylbenzo[b]thiophene-2-carboxamide; <24> N-(5-(benzyloxy)-3,4,6-trimethylpyridin-2-yl)-3-chloro-6-fluorobenzo[b]thiophene-2-carboxamide; <25> N-(5-(benzyloxy)-3,4,6-trimethylpyridin-2-yl)-3,6-dichlorobenzo[b]thiophene-2-carboxamide; <26> N-(5-(benzyloxy)-3,4,6-trimethylpyridin-2-yl)-3-chloro-6-methoxybenzo[b]thiophene-2-carboxamide; <27> N-(5-hydroxy-3,4,6-trimethylpyridin-2-yl)-1H-indole-2-carboxamide; <28> N-(5-hydroxy-3,4,6-trimethylpyridin-2-yl)-1-methyl-1H-indole-2-carboxamide; <29>7-bromo-N-(5-hydroxy-3,4,6-trimethylpyridin-2-yl)-1H-indole-2-carboxamide; <30>6-chloro-N-(5-hydroxy-3,4,6-trimethylpyridin-2-yl)-1H-indole-2-carboxamide; <31>6-bromo-N-(5-hydroxy-3,4,6-trimethylpyridin-2-yl)-1H-indole-2-carboxamide; <32>5-fluoro-N-(5-hydroxy-3,4,6-trimethylpyridin-2-yl)-1H-indole-2-carboxamide; <33>5-bromo-N-(5-hydroxy-3,4,6-trimethylpyridin-2-yl)-1H-indole-2-carboxamide; <34>5-chloro-N-(5-hydroxy-3,4,6-trimethylpyridin-2-yl)-1H-indole-2-carboxamide; <35> N-(5-hydroxy-3,4,6-trimethylpyridin-2-yl)-5-methyl-1H-indole-2-carboxamide; <36> N-(5-hydroxy-3,4,6-trimethylpyridin-2-yl)-5-(trifluoromethyl)-1H-indole-2-carboxamide; <37> N-(5-hydroxy- 3,4,6-trimethylpyridin-2-yl)-5-(trifluoromethoxy)-1H-indole-2-carboxamide; <38> N-(5-hydroxy-3,4,6-trimethylpyridin-2-yl)-6-methoxy-1H-indole-2-carboxamide; <39> N-(5-hydroxy-3,4,6-trimethylpyridin-2-yl)-5-methoxy-1H-indole-2-carboxamide; <40> N-(5-hydroxy-3,4,6-trimethylpyridin-2-yl)-5,6-dimethoxy-1H-indole-2-carboxamide; <41> N-(5-hydroxy-3,4,6-trimethylpyridin-2-yl)benzofuran-2-carboxamide; <42>5-chloro-N-(5-hydroxy-3,4,6-trimethylpyridin-2-yl)benzofuran-2-carboxamide; <43>5-bromo-N-(5-hydroxy-3,4,6-trimethylpyridin-2-yl)benzofuran-2-carboxamide; <44> N-(5-hydroxy-3,4,6-trimethylpyridin-2-yl)-7-methoxybenzofuran-2-carboxamide; <45> N-(5-hydroxy-3,4,6-trimethylpyridin-2-yl)-3-methylbenzofuran-2-carboxamide; <46> N-(5-hydroxy-3,4,6-trimethylpyridin-2-yl)benzo[b]thiophene-2-carboxamide; <47>3-chloro-N-(5-hydroxy-3,4,6-trimethylpyridin-2-yl)benzo[b]thiophene-2-carboxamide; <48>3-bromo-N-(5-hydroxy-3,4,6-trimethylpyridin-2-yl)benzo[b]thiophene-2-carboxamide; <49>3-chloro-N-(5-hydroxy-3,4,6-trimethylpyridin-2-yl)-6-methylbenzo[b]thiophene-2-carboxamide; <50>3-chloro-6-fluoro-N-(5-hydroxy-3,4,6-trimethylpyridin-2-yl)benzo[b]thiophene-2-carboxamide; <51>3,6-dichloro-N-(5-hydroxy-3,4,6-trimethylpyridin-2-yl)benzo[b]thiophene-2-carboxamide; <52>3-chloro-N-(5-hydroxy-3,4,6-trimethylpyridin-2-yl)-6-methoxybenzo[b]thiophene-2-carboxamide; <53>3-chloro-6-fluoro-N-(5-methoxy-3,4,6-trimethylpyridin-2-yl)benzo[b]thiophene-2-carboxamide; <54>3-chloro-6-fluoro-N-(5-methoxy-3,4,6-trimethylpyridin-2-yl)-N-methylbenzo[b]thiophene-2-carboxamide; <55>3-chloro-6-fluoro-N-(5-(2-(isopropylamino)-2-oxoethoxy)-3,4,6-trimethylpyridin-2-yl)benzo[b]thiophene-2-carboxamide; <56>3-chloro-N-(5-(2-(cyclopropylamino)-2-oxoethoxy)-3,4,6-trimethylpyridin-2-yl)-6-fluorobenzo[b]thiophene-2-carboxamide; <57>3-chloro-N-(5-(2-(cyclohexylamino)-2-oxoethoxy)-3,4,6-trimethylpyridin-2-yl)-6-fluorobenzo[b]thiophene-2-carboxamide; <58> N-(5-(2-(benzylamino)-2-oxoethoxy)-3,4,6-trimethylpyridin-2-yl)-3-chloro-6-fluorobenzo[b]thiophene-2-carboxamide; <59>3-chloro-6-fluoro-N-(3,4,6-trimethyl-5-(2-oxo-2-(phenylamino)ethoxy)pyridin-2-yl)benzo[b]thiophene-2-carboxamide; <60>6-(3-chloro-6-fluorobenzo[b]thiophene-2-carboxamido)-2,4,5-trimethylpyridin-3-yl benzoate; <61>6-(3-chloro-6-fluorobenzo[b]thiophene-2-carboxamido)-2,4,5-trimethylpyridin-3-yl 4-fluorobenzoate; <62>6-(3-chloro-6-fluorobenzo[b]thiophene-2-carboxamido)-2,4,5-trimethylpyridin-3-yl 3-methoxybenzoate; <63>6-(3-chloro-6-fluorobenzo[b]thiophene-2-carboxamido)-2,4,5-trimethylpyridin-3-yl 4-methoxybenzoate; <64>6-(3-chloro-6-fluorobenzo[b]thiophene-2-carboxamido)-2,4,5-trimethylpyridin-3-yl 5-fluoropicolinate; <65>6-(3-chloro-6-fluorobenzo[b]thiophene-2-carboxamido)-2,4,5-trimethylpyridin-3-yl 6-fluoronicotinate; <66>6-(3-chloro-6-fluorobenzo[b]thiophene-2-carboxamido)-2,4,5-trimethylpyridin-3-yl 5-chloropicolinate; <67>6-(3-chloro-6-fluorobenzo[b]thiophene-2-carboxamido)-2,4,5-trimethylpyridin-3-yl 6-chloropicolinate; <68>6-(3-chloro-6-fluorobenzo[b]thiophene-2-carboxamido)-2,4,5-trimethylpyridin-3-yl (3r,5r,7r)-adamantane-1-carboxylate; <69>6-(3-chloro-6-fluorobenzo[b]thiophene-2-carboxamido)-2,4,5-trimethylpyridin-3-yl morpholine-4-carboxylate.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, methylene chloride and acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an optical isomer, or a hydrate possibly produced from the same.

The term "hydrate" refers to a compound or a salt thereof of the present invention containing a stoichiometric or non-stoichiometric amount of water bound by a non-covalent intermolecular force. The hydrate of the compound represented by formula 1 of the present invention can contain a stoichiometric or non-stoichiometric amount of water bonded by a non-covalent intermolecular force. The hydrate can contain 1 equivalent or more of water, preferably 1 to 5 equivalents of water. The hydrate can be prepared by crystallizing the compound represented by formula 1, the isomer thereof, or the pharmaceutically acceptable salt thereof from water or the solvent containing water.

The term "solvate" refers to a compound or a salt thereof of the present invention containing a stoichiometric or non-stoichiometric amount of solvent bound by a non-covalent intermolecular force. Preferred solvents therefor include volatile, non-toxic, and/or solvents suitable for administration to human.

The term "isomer" refers to a compound or a salt thereof of the present invention having the same chemical formula or molecular formula, but structurally or sterically different. Such isomers include structural isomers such as tautomers, R or S isomers having an asymmetric carbon center, stereoisomers such as geometric isomers (trans, cis), and optical isomers (enantiomers). All these isomers and mixtures thereof are also included in the scope of the present invention.

The compound represented by formula 1 of the present invention can be prepared according to the preparation method shown in reaction formula 1 or reaction formula 2 below, but this is only an example, and is not limited thereto, and each preparation step can be performed using a method well known to those in the art.

The compound represented by formula 1 according to the present invention can be prepared by a method for preparing a compound represented by formula 1 comprising a step of preparing a compound represented by formula 1 by reacting a compound represented by formula 2 with a compound represented by formula 3, as shown in reaction formula 1 below:

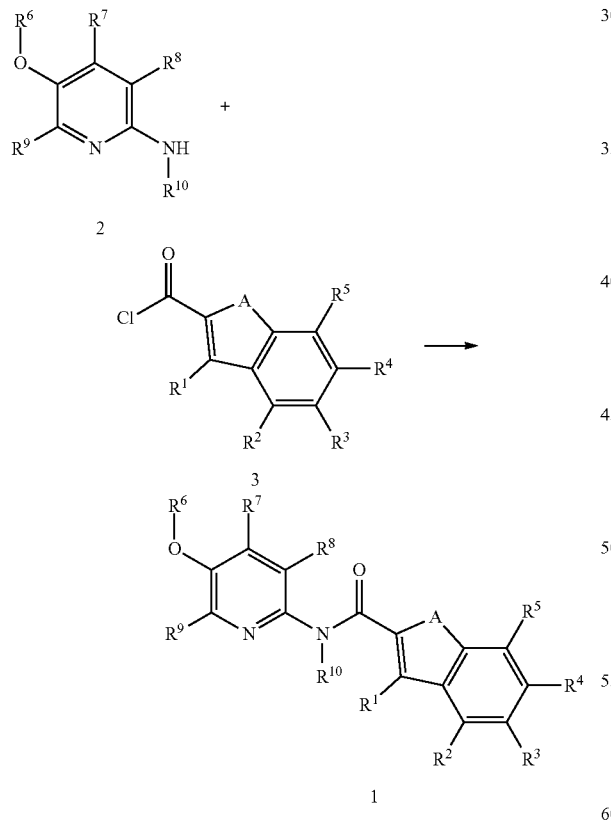

[Reaction Formula 1]

(In reaction formula 1,
A, $R^1$, $R^2$, $R^3$, $R^4$, $R^5$, $R^6$, $R^7$, $R^8$, $R^9$, and $R^{10}$ are as defined in formula 1).

As shown in reaction formula 1, amine of the compound represented by formula 2 and Cl of the compound represented by formula 3 react to prepare a compound represented by Formula 1 in which an amide bond is formed. The above step can be performed using a method well known to those in the art, and the compound can be prepared according to an embodiment of the present invention, but this is only an example and is not limited thereto.

The compound represented by formula 1 according to the present invention can be prepared by a method for preparing a compound represented by formula 1 comprising the following steps, as shown in reaction formula 2 below:

preparing a compound represented by formula 4 by reacting a compound represented by formula 2a with a compound represented by formula 3 (step 1);

preparing a compound represented by formula 1a by deprotecting the compound represented by formula 4 obtained in step 1 above (step 2); and preparing a compound represented by formula 1b by reacting the compound represented by formula 1a obtained in step 2 above with a compound represented by formula 5 (step 3):

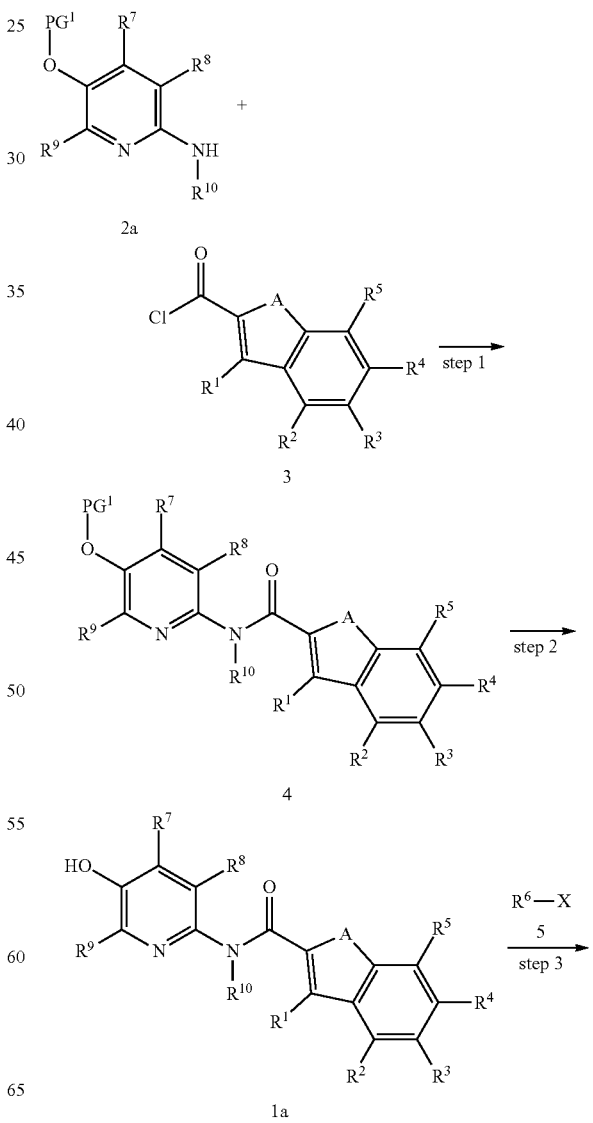

[Reaction Formula 2]

-continued

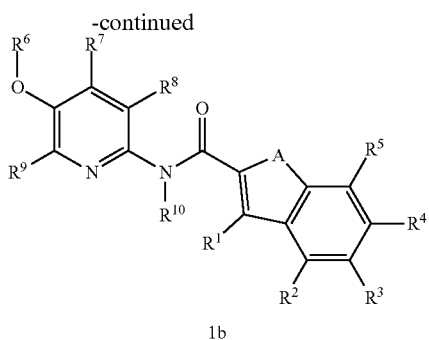

1b (In reaction formula 2,

A, $R^1$, $R^2$, $R^3$, $R^4$, $R^5$, $R^6$, $R^7$, $R^8$, $R^9$, and $R^{10}$ are as defined in formula 1 except when $R^6$ is hydrogen;

the compound represented by formula 1a is a derivative of formula 1 wherein $R^6$ is hydrogen;

the compound represented by formula 1b is a derivative of formula 1 except when $R^6$ is hydrogen;

$PG^1$ is an alcohol protecting group selected from the group consisting of acetyl (Ac), benzoyl (Bz), benzyl (Bn), methylthiomethyl ether, MEM (0-methoxyethoxymethyl ether), DMT (dimethoxytrityl, [bis-(4-methoxyphenyl)phenylmethyl]), MOM (methoxymethyl ether), MMT (methoxytrityl [(4-methoxyphenyl)diphenylmethyl]), PMP (p-methoxybenzyl ether), Piv (pivaloyl), THP (tetrahydropyranyl), THF (tetrahydrofuran) and Trityl (triphenylmethyl, Tr); and X is halogen).

As shown in step 1 of reaction formula 2, amine of the compound represented by formula 2a and Cl of the compound represented by formula 3 react to prepare a compound represented by Formula 4 in which an amide bond is formed. The above step can be performed using a method well known to those in the art, and the compound can be prepared according to an embodiment of the present invention, but this is only an example and is not limited thereto.

Step 2 of reaction formula 2 is a step of preparing an alcohol compound represented by formula 1a by removing an alcohol protecting group of the compound represented by formula 4. The step can be performed according to a known method capable of removing the alcohol protecting group, and those skilled in the art can easily select and proceed under what conditions the removal reaction can be performed according to the type of the protecting group. The compound can be prepared according to an embodiment of the present invention, but this is only an example and is not limited thereto.

Step 3 of Scheme 2 is a step of preparing a compound represented by formula 1b by reacting hydroxyl of the compound represented by formula 1a with halide of the compound represented by formula 4. The above step can be performed using a method well known to those in the art, and the compound can be prepared according to an embodiment of the present invention, but this is only an example and is not limited thereto.

In another aspect of the present invention, the present invention provides a pharmaceutical composition comprising a compound represented by formula 1, an isomer thereof, a solvate thereof, a hydrate thereof, or a pharmaceutically acceptable salt thereof as an active ingredient for the prevention or treatment of autoimmune disease.

The compound may inhibit the adhesion of monocytes to intestinal epithelial cells by TNF-α or IL-6.

The autoimmune disease can be at least one selected from the group consisting of inflammatory bowel disease, asthma, type 1 diabetes, rheumatoid arthritis, polymyalgia rheumatica, ankylosing spondylitis, psoriatic arthritis, psoriasis, eczema, sclerosis, vitiligo, multiple sclerosis, IL-17-induced dementia, peripheral neuritis, uveitis, polymyositis/dermatomyositis, autoimmune cytopenia, autoimmune myocarditis, atopic dermatitis, primary cirrhosis, dry eye syndrome, fibromyalgia, Goodpasture's syndrome, autoimmune meningitis, Sjogren's syndrome, systemic lupus erythematosus, Addison's disease, alopecia areata, autoimmune hepatitis, autoimmune mumps, dystrophic epidermolysis bullosa, epididymitis, glomerulonephritis, Graves' disease, celiac disease, Guillain-Barré syndrome, Hashimoto's disease, hemolytic anemia, myasthenia gravis, amyotrophic lateral sclerosis, pemphigus vulgaris, rheumatic fever, sarcoidosis, skin sclerosis, spondyloarthrosis, thyroiditis, vasculitis, vitiligo, myxedema, pernicious anemia, antiphospholipid syndrome, late and chronic rejection of solid organ transplantation, and graft-versus-host disease.

The inflammatory bowel disease can be any one selected from the group consisting of enteritis, colitis, ulcerative enteritis, Crohn's disease, Crohn's cytoma, irritable bowel syndrome, hemorrhagic rectal ulcer, pouchitis, peptic ulcer, intestinal Behcet's disease and gastritis.

In the pharmaceutical composition according to the present invention, the compound represented by formula 1 or the pharmaceutically acceptable salt thereof can be administered orally or parenterally, preferably parenterally, and be used in general forms of pharmaceutical formulation. That is, the compound or the pharmaceutically acceptable salt thereof can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

At this time, to prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example: lactose, dextrose, sucrose, mannitol, sorbitol, cellulose and/or glycine) and lubricants (for example: silica, talc, stearate and its magnesium or calcium salt and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides a health functional food comprising a compound represented by formula 1, an isomer thereof, a solvate thereof, a hydrate thereof or a pharmaceutically acceptable salt thereof as an active ingredient for the prevention or amelioration of autoimmune disease.

In another aspect of the present invention, the present invention provides a method for preventing or treating autoimmune disease, which comprises a step of administering a pharmaceutical composition or a health functional food comprising a compound represented by formula 1, an isomer thereof, a solvate thereof, a hydrate thereof or a pharmaceutically acceptable salt thereof as an active ingredient to a subject in need.

In another aspect of the present invention, the present invention provides a use of the pharmaceutical composition or the health functional food above comprising a compound represented by formula 1, an isomer thereof, a solvate thereof, a hydrate thereof or a pharmaceutically acceptable salt thereof as an active ingredient for the prevention or treatment of autoimmune disease.

Hereinafter, the present invention will be described in detail by the following examples and experimental examples.

However, the following examples and experimental examples are only for illustrating the present invention, and the contents of the present invention are not limited thereto.

<Preparative Example 1> Preparation of 5-(benzyloxy)-3,4,6-trimethylpyridin-2-amine

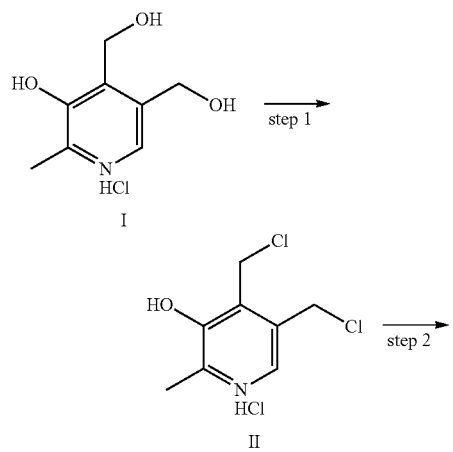

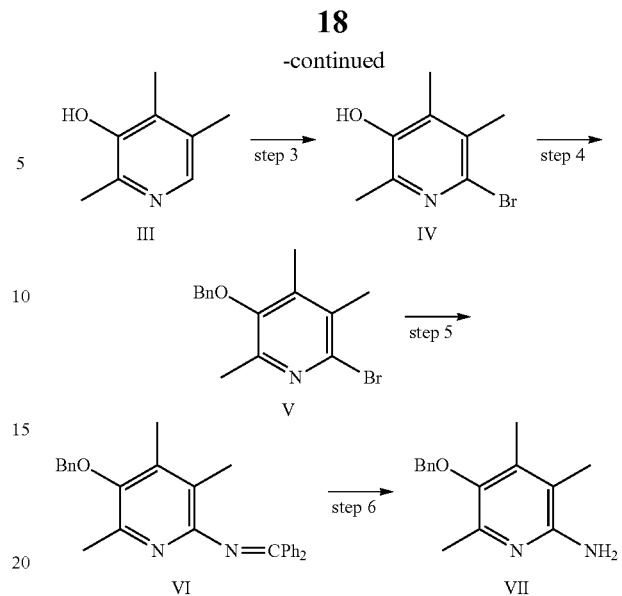

Step 1: Synthesis of 4,5-bis(chloromethyl)-2-methylpyridin-3-ol hydrochloride (Formula II)

SOCl$_2$ (15 mL) and DMF (0.38 mL) were added to pyridoxinehydrochloride (Formula I) (10 g), and the mixture was stirred at 80° C. for 30 minutes. The reaction mixture was cooled to room temperature, to which Et$_2$O (140 mL) was added, and the mixture was stirred under ice cooling for 1 hour. The precipitated solid in the reaction solution was filtered under reduced pressure, and the filtered solid was washed with Et$_2$O and dried to give the target compound II (11.3 g) as a white solid.

$^1$H-NMR ((CD$_3$)$_2$SO) δ 8.42 (s, 1H), 4.99 (s, 2H), 4.96 (s, 2H), 2.63 (s, 3H).

Step 2: Synthesis of 2,4,5-trimethylpyridin-3-ol (Formula III)

Zinc powder (8.08 g) was added in small portions to the acetic acid (50 mL) suspension of compound II (10 g) several times, and the mixture was stirred under reflux at 130° C. for 2 hours. The reaction mixture was cooled to room temperature, and the solid in the reaction solution was removed by filtration under reduced pressure. Then, the pH of the filtrate was adjusted to 6 using 10 M NaOH solution. The filtrate was saturated with salt and then extracted several times with EtOAc. The extract was washed with saturated brine, dried over anhydrous MgSO$_4$, filtered, and concentrated under reduced pressure. The residue was purified by column chromatography (CHCl$_3$:MeOH=20:1) to give the target compound III (5.2 g) as a white solid.

$^1$H-NMR ((CD$_3$)$_2$SO) δ 8.49 (s, 1H), 7.72 (s, 1H), 2.31 (s, 3H), 2.12 (s, 3H), 2.08 (s, 3H).

Step 3: Synthesis of 6-bromo-2,4,5-trimethylpyridin-3-ol (Formula IV)

1,3-Dibromo-5,5-dimethylhydantoin (DBDMH, 2.5 g) was added to the THF suspension (30 mL) of Compound III (2.5 g), followed by stirring at room temperature for 3 hours. After the reaction mixture was concentrated, the residue was diluted with EtOAc and water, and the aqueous layer was extracted with EtOAc. The EtOAc solution was washed with saturated brine, dried over anhydrous MgSO$_4$, filtered, and concentrated under reduced pressure. The residue was purified by column chromatography (EtOAc:Hexanes=1:4) to give the target compound IV (3.22 g) as a pale yellow solid.

$^1$H-NMR (CDCl$_3$) δ 5.56 (br s, 1H), 2.42 (s, 3H), 2.31 (s, 3H), 2.25 (s, 3H).

Step 4: Synthesis of 3-(benzyloxy)-6-bromo-2,4,5-trimethylpyridine (Formula V)

K$_2$CO$_3$ (20.78 g) and benzyl chloride (5.2 mL) were sequentially added to a DMF solution (15 mL) of compound IV (6.5 g), followed by stirring at room temperature for 12 hours. The reaction solution was diluted with EtOAc and washed several times with a small amount of water. The EtOAc solution was washed with saturated brine, dried over anhydrous MgSO$_4$, filtered, and concentrated under reduced pressure. The residue was purified by column chromatography (EtOAc:Hexanes=1:20) to give the target compound V (8.9 g) as a white solid.

$^1$H-NMR (CDCl$_3$) δ 7.38-7.43 (m, 5H), 4.77 (s, 2H), 2.46 (s, 3H), 2.32 (s, 3H), 2.24 (s, 3H).

Step 5: Synthesis of 5-(benzyloxy)-N-(diphenylmethylene)-3,4,6-trimethylpyridin-2-amine (Formula VI)

Benzophenoneimine (1.73 mL) was added to a toluene (30 mL) solution of compound V (3 g), tris(dibenzylideneacetone)dipalladium(0) (203 mg), 2,2'-bis(diphenylphosphino)-1,1'-binaphthyl (249 mg) and NaO$^t$Bu (1.36 g), and the mixture was stirred under reflux for 12 hours. The reaction solution was cooled to room temperature, and diluted with EtOAc and water. The EtOAc solution was washed several times with saturated brine, dried over anhydrous MgSO$_4$, filtered, and concentrated under reduced pressure. The residue was purified by column chromatography (EtOAc:Hexanes=1:4) to give the target compound VI (3.28 g) as a yellow solid.

$^1$H-NMR (CDCl$_3$) δ 7.80 (d, J=7.1 Hz, 2H), 7.17-7.48 (m, 13H), 4.69 (s, 2H), 2.29 (s, 3H), 2.03 (s, 3H), 1.91 (s, 3H).

Step 6: Synthesis of 5-(benzyloxy)-3,4,6-trimethylpyridin-2-amine (Formula VII)

A solution in which acetyl chloride (3.2 mL) was added little by little to methanol (20 mL) under ice cooling was added to a methanol (60 mL)-THF (20 mL) mixed solution of compound VI (7.7 g), followed by stirring at room temperature for 12 hours. After the reaction solution was concentrated under reduced pressure, the residue was diluted with EtOAc and washed several times with saturated sodium hydrogen carbonate solution. The EtOAc solution was washed with saturated brine, dried over anhydrous MgSO$_4$, filtered, and concentrated under reduced pressure. The residue was purified by column chromatography (CHCl$_3$:MeOH=20:1) to give the target compound VII (4.36 g) as a pale yellow solid.

$^1$H-NMR (CDCl$_3$) δ 7.31-7.45 (m, 5H), 4.68 (s, 2H), 4.25 (br s, 1H), 2.34 (s, 3H), 2.16 (s, 3H), 1.99 (s, 3H).

General Preparation Procedure 1 of Examples

According to the preparation method of reaction formula A, the compounds of examples 1-26 (Compounds IX-01~IX-26) were prepared.

[Reaction Formula A]

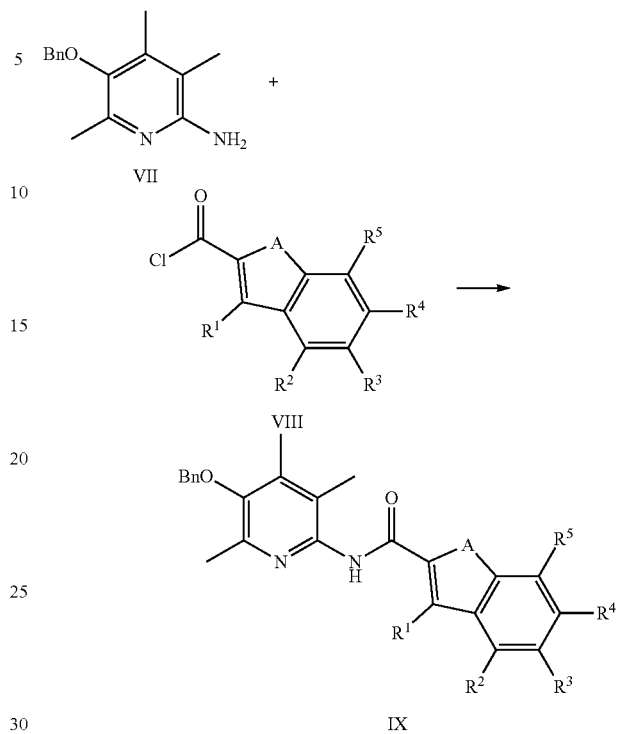

In reaction formula A above,

A, R$^1$, R$^2$, R$^3$, R$^4$ and R$^5$ are as defined in this specification.

Particularly, compound VIII (1.5~2.0 mmol) and Et$_3$N (2.0 mmol) were sequentially added to a CH$_2$Cl$_2$ (or ClCH$_2$CH$_2$Cl, 10 mL) solution of compound VII (1.0 mmol) at room temperature, and the reaction mixture was stirred at room temperature ~60° C. until the compound VII disappeared on TLC. The reaction mixture was diluted with CH$_2$Cl$_2$ and washed with saturated NaHCO$_3$ aqueous solution. The CH$_2$Cl$_2$ solution was dried over anhydrous MgSO$_4$, filtered, concentrated under reduced pressure, and the residue was purified by silica gel column chromatography to give compounds IX-01 to IX-26.

<Example 1> Synthesis of N-(5-(benzyloxy)-3,4,6-trimethylpyridin-2-yl)-1H-indole-2-carboxamide (Formula IX-01)

The target compound was prepared according to the method of general preparation procedure 1 of examples.

$^1$H-NMR (CDCl$_3$) δ 9.69 (s, 1H), 8.75 (s, 1H), 7.67 (d, J=7.9 Hz, 1H), 7.52-7.27 (m, 7H), 7.19-7.08 (m, 2H), 4.80 (s, 2H), 2.47 (s, 3H), 2.31 (s, 3H), 2.23 (s, 3H).

<Example 2> Synthesis of N-(5-(benzyloxy)-3,4,6-trimethylpyridin-2-yl)-1-methyl-1H-indole-2-carboxamide (Formula IX-02)

The target compound was prepared according to the method of general preparation procedure 1 of examples.

$^1$H-NMR (CDCl$_3$) δ 8.34 (s, 1H), 7.68 (d, J=8.0 Hz, 1H), 7.51-7.32 (m, 7H), 7.15 (d, J=0.5 Hz, 2H), 4.80 (s, 2H), 4.06 (s, 3H), 2.47 (s, 3H), 2.30 (s, 3H), 2.23 (s, 3H).

<Example 3> Synthesis of N-(5-(benzyloxy)-3,4,6-trimethylpyridin-2-yl)-7-bromo-1H-indole-2-carboxamide (Formula IX-03)

The target compound was prepared according to the method of general preparation procedure 1 of examples.
$^1$H-NMR (CDCl$_3$) δ 9.45 (s, 2H), 7.60 (d, J=8.0 Hz, 1H), 7.51-7.33 (m, 6H), 7.21 (s, 1H), 7.04 (d, J=7.8 Hz, 1H), 4.77 (s, 2H), 2.45 (s, 3H), 2.26 (s, 3H), 2.22 (s, 3H).

<Example 4> Synthesis of N-(5-(benzyloxy)-3,4,6-trimethylpyridin-2-yl)-6-chloro-1H-indole-2-carboxamide (Formula IX-04)

The target compound was prepared according to the method of general preparation procedure 1 of examples.
$^1$H-NMR ((CD$_3$)$_2$SO) δ 11.84 (s, 1H), 10.51 (s, 1H), 7.69 (d, J=8.5 Hz, 1H), 7.56-7.35 (m, 7H), 7.08 (dd, J=8.5, 1.9 Hz, 1H), 4.85 (s, 2H), 2.40 (s, 3H), 2.26 (s, 3H), 2.08 (s, 3H).

<Example 5> Synthesis of N-(5-(benzyloxy)-3,4,6-trimethylpyridin-2-yl)-6-bromo-1H-indole-2-carboxamide (Formula IX-05)

The target compound was prepared according to the method of general preparation procedure 1 of examples.
$^1$H-NMR ((CD$_3$)$_2$SO) δ 11.84 (s, 1H), 10.52 (s, 1H), 7.65 (d, J=10.3 Hz, 2H), 7.58-7.35 (m, 6H), 7.20 (dd, J=8.4, 1.2 Hz, 1H), 4.86 (s, 2H), 2.40 (s, 3H), 2.27 (s, 3H), 2.09 (s, 3H).

<Example 6> Synthesis of N-(5-(benzyloxy)-3,4,6-trimethylpyridin-2-yl)-5-fluoro-1H-indole-2-carboxamide (Formula IX-06)

The target compound was prepared according to the method of general preparation procedure 1 of examples.
$^1$H-NMR (CDCl$_3$) δ 9.66 (s, 1H), 8.64 (s, 1H), 7.52-7.37 (m, 5H), 7.30 (dd, J=6.6, 2.8 Hz, 2H), 7.09-6.99 (m, 2H), 4.81 (s, 2H), 2.46 (s, 3H), 2.30 (s, 3H), 2.22 (s, 3H).

<Example 7> Synthesis of N-(5-(benzyloxy)-3,4,6-trimethylpyridin-2-yl)-5-bromo-1H-indole-2-carboxamide (Formula IX-07)

The target compound was prepared according to the method of general preparation procedure 1 of examples.
$^1$H-NMR (CDCl$_3$) δ 9.93 (s, 1H), 7.80 (d, J=1.7 Hz, 1H), 7.50-7.37 (m, 6H), 7.35 (d, J=1.8 Hz, 1H), 7.30 (s, 1H), 7.06 (d, J=1.4 Hz, 1H), 4.75 (s, 2H), 2.48 (s, 3H), 2.21 (d, J=8.1 Hz, 6H).

<Example 8> Synthesis of N-(5-(benzyloxy)-3,4,6-trimethylpyridin-2-yl)-5-chloro-1H-indole-2-carboxamide (Formula IX-08)

The target compound was prepared according to the method of general preparation procedure 1 of examples.
$^1$H-NMR (CDCl$_3$) δ 10.25 (s, 1H), 9.18 (dd, J=5.2, 2.9 Hz, 1H), 7.58 (s, 1H), 7.43 (dd, J=11.2, 5.4 Hz, 5H), 7.19 (d, J=2.6 Hz, 2H), 7.02 (s, 1H), 4.81 (s, 2H), 2.45 (s, 3H), 2.30 (s, 3H), 2.23 (s, 3H).

<Example 9> Synthesis of N-(5-(benzyloxy)-3,4,6-trimethylpyridin-2-yl)-5-methyl-1H-indole-2-carboxamide (Formula IX-09)

The target compound was prepared according to the method of general preparation procedure 1 of examples.
$^1$H-NMR (CDCl$_3$) δ 12.72 (s, 1H), 11.04 (s, 1H), 10.37 (s, 1H), 7.84 (s, 1H), 7.55-7.35 (m, 7H), 7.20 (d, J=8.4 Hz, 1H), 4.84 (s, 2H), 2.55 (s, 3H), 2.52 (s, 3H), 2.31 (s, 3H), 2.25 (s, 3H).

<Example 10> Synthesis of N-(5-(benzyloxy)-3,4,6-trimethylpyridin-2-yl)-5-(trifluoromethyl)-1H-indole-2-carboxamide (Formula IX-10)

The target compound was prepared according to the method of general preparation procedure 1 of examples.
$^1$H-NMR (CDCl$_3$) δ 10.26 (s, 1H), 9.16 (s, 1H), 7.94 (s, 1H), 7.53-7.33 (m, 7H), 7.17 (d, J=1.3 Hz, 1H), 4.83 (s, 2H), 2.46 (s, 3H), 2.32 (s, 3H), 2.24 (s, 3H).

<Example 11> Synthesis of N-(5-(benzyloxy)-3,4,6-trimethylpyridin-2-yl)-5-(trifluoromethoxy)-1H-indole-2-carboxamide (Formula IX-11)

The target compound was prepared according to the method of general preparation procedure 1 of examples.
$^1$H-NMR (CDCl$_3$) δ 10.06 (s, 1H), 9.03 (s, 1H), 7.53-7.28 (m, 7H), 7.12 (d, J=11.8 Hz, 2H), 4.82 (s, 2H), 2.46 (s, 3H), 2.31 (s, 3H), 2.23 (s, 3H).

<Example 12> Synthesis of N-(5-(benzyloxy)-3,4,6-trimethylpyridin-2-yl)-6-methoxy-1H-indole-2-carboxamide (Formula IX-12)

The target compound was prepared according to the method of general preparation procedure 1 of examples.
$^1$H-NMR (CDCl$_3$) δ 9.54 (s, 1H), 8.76-8.54 (m, 1H), 7.56-7.35 (m, 6H), 7.03 (d, J=1.8 Hz, 1H), 6.81 (dd, J=4.6, 2.4 Hz, 2H), 4.79 (s, 2H), 3.83 (s, 3H), 2.45 (s, 3H), 2.28 (s, 3H), 2.22 (s, 3H).

<Example 13> Synthesis of N-(5-(benzyloxy)-3,4,6-trimethylpyridin-2-yl)-5-methoxy-1H-indole-2-carboxamide (Formula IX-13)

The target compound was prepared according to the method of general preparation procedure 1 of examples.
$^1$H-NMR (CDCl$_3$) δ 9.72 (s, 1H), 9.24-8.76 (m, 1H), 7.54-7.33 (m, 5H), 7.23 (s, 1H), 7.04 (s, 2H), 6.98-6.89 (m, 1H), 4.78 (s, 2H), 3.83 (s, 3H), 2.46 (s, 3H), 2.28 (s, 3H), 2.22 (s, 3H).

<Example 14> Synthesis of N-(5-(benzyloxy)-3,4,6-trimethylpyridin-2-yl)-5,6-dimethoxy-1H-indole-2-carboxamide (Formula IX-14)

The target compound was prepared according to the method of general preparation procedure 1 of examples.
$^1$H-NMR (CDCl$_3$) δ 9.57 (s, 1H), 7.41 (dd, J=8.6, 3.9 Hz, 5H), 7.02 (s, 2H), 6.84 (s, 1H), 4.73 (s, 2H), 3.91 (s, 6H), 2.47 (s, 3H), 2.22 (d, J=4.8 Hz, 6H).

<Example 15> Synthesis of N-(5-(benzyloxy)-3,4,6-trimethylpyridin-2-yl)benzofuran-2-carboxamide (Formula IX-15)

The target compound was prepared according to the method of general preparation procedure 1 of examples.
$^1$H-NMR (CDCl$_3$) δ 8.60 (s, 1H), 7.70 (d, J=7.7 Hz, 1H), 7.59 (d, J=0.8 Hz, 1H), 7.57-7.28 (m, 8H), 4.81 (s, 2H), 2.47 (s, 3H), 2.30 (s, 3H), 2.23 (s, 3H).

<Example 16> Synthesis of N-(5-(benzyloxy)-3,4,
6-trimethylpyridin-2-yl)-5-chlorobenzofuran-2-carboxamide (Formula IX-16)

The target compound was prepared according to the method of general preparation procedure 1 of examples.
$^1$H-NMR (CDCl$_3$) δ 8.64 (s, 1H), 7.70-7.64 (m, 1H), 7.52 (d, J=0.8 Hz, 1H), 7.50-7.36 (m, 7H), 4.81 (s, 2H), 2.46 (s, 3H), 2.30 (s, 3H), 2.22 (s, 3H).

<Example 17> Synthesis of N-(5-(benzyloxy)-3,4,
6-trimethylpyridin-2-yl)-5-bromobenzofuran-2-carboxamide (Formula IX-17) [N-(5-(benzyloxy)-3,4,
6-trimethylpyridin-2-yl)-5-bromobenzofuran-2-carboxamide]

The target compound was prepared according to the method of general preparation procedure 1 of examples.
$^1$H-NMR (CDCl$_3$) δ 8.70 (s, 1H), 7.85 (d, J=1.9 Hz, 1H), 7.54 (d, J=3.3 Hz, 2H), 7.50-7.38 (m, 6H), 4.81 (s, 2H), 2.47 (s, 3H), 2.31 (s, 3H), 2.22 (s, 3H).

<Example 18> Synthesis of N-(5-(benzyloxy)-3,4,
6-trimethylpyridin-2-yl)-7-methoxybenzofuran-2-carboxamide (Formula IX-18)

The target compound was prepared according to the method of general preparation procedure 1 of examples.
$^1$H-NMR (CDCl$_3$) δ 8.98 (s, 1H), 7.66-7.59 (m, 1H), 7.51-7.33 (m, 5H), 7.25-7.22 (m, 2H), 6.94 (dd, J=7.3, 1.6 Hz, 1H), 4.81 (s, 2H), 4.03 (s, 3H), 2.49 (s, 3H), 2.31 (d, J=2.3 Hz, 3H), 2.22 (s, 3H).

<Example 19> Synthesis of N-(5-(benzyloxy)-3,4,
6-trimethylpyridin-2-yl)-3-methylbenzofuran-2-carboxamide (Formula IX-19)

The target compound was prepared according to the method of general preparation procedure 1 of examples.
$^1$H-NMR (CDCl$_3$) δ 8.59 (s, 1H), 7.63 (d, J=7.9 Hz, 1H), 7.56-7.27 (m, 8H), 4.81 (s, 2H), 2.64 (s, 3H), 2.48 (s, 3H), 2.27 (d, J=10.2 Hz, 6H).

<Example 20> Synthesis of N-(5-(benzyloxy)-3,4,
6-trimethylpyridin-2-yl)benzo[b]thiophene-2-carboxamide (Formula IX-20)

The target compound was prepared according to the method of general preparation procedure 1 of examples.
$^1$H-NMR (CDCl$_3$) δ 8.69 (s, 1H), 7.97 (s, 1H), 7.90-7.82 (m, 2H), 7.51-7.35 (m, 7H), 4.80 (s, 2H), 2.44 (s, 3H), 2.29 (s, 3H), 2.23 (s, 3H).

<Example 21> Synthesis of N-(5-(benzyloxy)-3,4,
6-trimethylpyridin-2-yl)-3-chlorobenzo[b]thiophene-2-carboxamide (Formula IX-21)

The target compound was prepared according to the method of general preparation procedure 1 of examples.
$^1$H-NMR (CDCl$_3$) δ 8.87 (s, 1H), 7.97-7.90 (m, 1H), 7.85 (dt, J=5.2, 3.3 Hz, 1H), 7.54-7.39 (m, 7H), 4.81 (s, 2H), 2.48 (s, 3H), 2.29 (s, 3H), 2.24 (s, 3H).

<Example 22> Synthesis of N-(5-(benzyloxy)-3,4,
6-trimethylpyridin-2-yl)-3-bromobenzo[b]thiophene-2-carboxamide (Formula IX-22)

The target compound was prepared according to the method of general preparation procedure 1 of examples.

$^1$H-NMR (CDCl$_3$) δ 8.89 (s, 1H), 7.97-7.82 (m, 2H), 7.56-7.38 (m, 7H), 4.81 (s, 2H), 2.47 (s, 3H), 2.30 (s, 3H), 2.25 (s, 3H).

<Example 23> Synthesis of N-(5-(benzyloxy)-3,4,
6-trimethylpyridin-2-yl)-3-chloro-6-methylbenzo[b]thiophene-2-carboxamide (Formula IX-23)

The target compound was prepared according to the method of general preparation procedure 1 of examples.
$^1$H-NMR (CDCl$_3$) δ 10.27 (s, 1H), 8.65 (s, 1H), 8.34 (d, J=1.6 Hz, 1H), 7.91 (d, J=8.7 Hz, 1H), 7.63 (dd, J=8.7, 1.9 Hz, 1H), 2.32 (s, 3H), 2.18 (s, 3H), 2.10 (s, 3H).

<Example 24> Synthesis of N-(5-(benzyloxy)-3,4,
6-trimethylpyridin-2-yl)-3-chloro-6-fluorobenzo[b]thiophene-2-carboxamide (Formula IX-24)

The target compound was prepared according to the method of general preparation procedure 1 of examples.
$^1$H-NMR (CDCl$_3$) δ 8.84 (s, 1H), 7.89 (dd, J=9.0, 5.0 Hz, 1H), 7.58-7.50 (m, 1H), 7.49-7.33 (m, 5H), 7.32-7.27 (m, 1H), 4.81 (s, 2H), 2.47 (s, 3H), 2.30 (s, 3H), 2.24 (s, 3H).

<Example 25> Synthesis of N-(5-(benzyloxy)-3,4,
6-trimethylpyridin-2-yl)-3,6-dichlorobenzo[b]thiophene-2-carboxamide (Formula IX-25)

The target compound was prepared according to the method of general preparation procedure 1 of examples.
$^1$H-NMR (CDCl$_3$) δ 8.97-8.61 (m, 1H), 7.84 (dd, J=5.2, 3.4 Hz, 2H), 7.53-7.34 (m, 6H), 4.81 (s, 6H), 2.46 (s, 3H), 2.29 (s, 3H), 2.24 (s, 3H).

<Example 26> Synthesis of N-(5-(benzyloxy)-3,4,
6-trimethylpyridin-2-yl)-3-chloro-6-methoxybenzo[b]thiophene-2-carboxamide (Formula IX-26)

The target compound was prepared according to the method of general preparation procedure 1 of examples.
$^1$H-NMR (CDCl$_3$) δ 8.77 (s, 1H), 7.79 (d, J=9.0 Hz, 1H), 7.53-7.33 (m, 5H), 7.12 (dd, J=9.0, 2.3 Hz, 1H), 4.81 (s, 2H), 3.91 (s, 3H), 2.47 (s, 3H), 2.29 (s, 3H), 2.23 (s, 3H).

General Preparation Procedure 2 of Examples

According to the preparation method of reaction formula B below, the compounds of examples 27-52 (Compounds X-01~X-26) were prepared.

[Reaction Formula B]

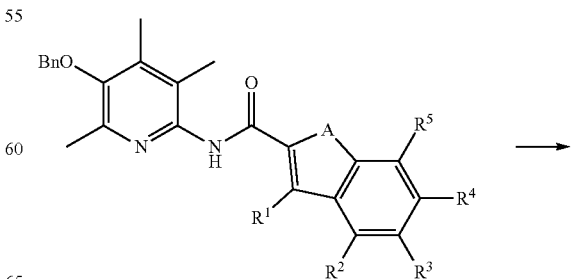

IX

-continued

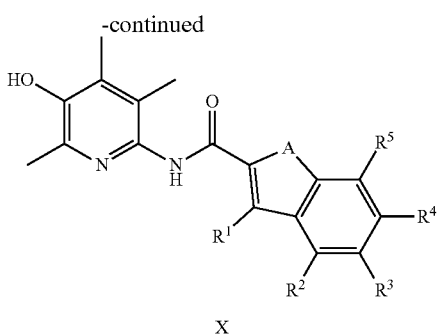

X

In reaction formula B above,

A, $R^1$, $R^2$, $R^3$, $R^4$ and $R^5$ are as defined in this specification.

Pentamethylbenzene (3.0 mmol) was added to a $CH_2Cl_2$ (10 mL) of compound IX (1.0 mmol), and the reaction solution was cooled with ice. A $CH_2Cl_2$ solution (2.0 mmol) of 1 M $BCl_3$ was slowly added thereto, and the reaction mixture was stirred under ice cooling until the compound IX disappeared on TLC. To the reaction solution, 10 mL of a 9:1 mixed solution of $CHCl_3$ and MeOH was added, stirred at room temperature for 30 minutes, and then concentrated under reduced pressure. The residue was purified by silica gel column chromatography to give compounds X-01~X-26.

<Example 27> Synthesis of N-(5-hydroxy-3,4,6-trimethylpyridin-2-yl)-1H-indole-2-carboxamide (Formula X-01)

The target compound was prepared according to the method of general preparation procedure 2 of examples.
$^1$H-NMR (($CD_3$)$_2$SO) δ 11.64 (s, 1H), 10.24 (s, 1H), 8.60 (s, 1H), 7.64 (d, J=8.0 Hz, 1H), 7.45 (d, J=8.2 Hz, 1H), 7.36 (d, J=1.4 Hz, 1H), 7.31-7.13 (m, 1H), 7.10-6.99 (m, 1H), 2.35 (s, 3H), 2.18 (s, 3H), 2.05 (s, 3H).

<Example 28> Synthesis of N-(5-hydroxy-3,4,6-trimethylpyridin-2-yl)-1-methyl-1H-indole-2-carboxamide (Formula X-02)

The target compound was prepared according to the method of general preparation procedure 2 of examples.
$^1$H-NMR (($CD_3$)$_2$SO) δ 10.18 (s, 1H), 8.56 (s, 1H), 7.67 (d, J=7.9 Hz, 1H), 7.55 (d, J=8.4 Hz, 1H), 7.34-7.25 (m, 2H), 7.13 (dd, J=11.0, 3.9 Hz, 1H), 4.00 (s, 3H), 2.35 (s, 3H), 2.18 (s, 3H), 2.07 (s, 3H).

<Example 29> Synthesis of 7-bromo-N-(5-hydroxy-3,4,6-trimethylpyridin-2-yl)-1H-indole-2-carboxamide (Formula X-03)

The target compound was prepared according to the method of general preparation procedure 2 of examples.
$^1$H-NMR (($CD_3$)$_2$SO) δ 11.62 (s, 1H), 10.64 (d, J=0.8 Hz, 1H), 9.09-8.86 (m, 1H), 7.70 (d, J=7.9 Hz, 1H), 7.46 (dd, J=14.5, 4.5 Hz, 2H), 7.04 (t, J=7.8 Hz, 1H), 2.39 (s, 3H), 2.22 (s, 3H), 2.09 (s, 3H).

<Example 30> Synthesis of 6-chloro-N-(5-hydroxy-3,4,6-trimethylpyridin-2-yl)-1H-indole-2-carboxamide (Formula X-04)

The target compound was prepared according to the method of general preparation procedure 2 of examples.
$^1$H-NMR (($CD_3$)$_2$SO) δ 11.83 (s, 1H), 10.36 (s, 1H), 8.65 (s, 1H), 7.68 (d, J=8.5 Hz, 1H), 7.42 (d, J=14.2 Hz, 2H), 7.07 (dd, J=8.5, 1.6 Hz, 1H), 2.34 (s, 3H), 2.17 (s, 3H), 2.03 (s, 3H).

<Example 31> Synthesis of 6-bromo-N-(5-hydroxy-3,4,6-trimethylpyridin-2-yl)-1H-indole-2-carboxamide (Formula X-05)

The target compound was prepared according to the method of general preparation procedure 2 of examples.
$^1$H-NMR (($CD_3$)$_2$SO) δ 11.79 (s, 1H), 10.32 (s, 1H), 8.62 (s, 1H), 7.63 (d, J=8.7 Hz, 2H), 7.38 (d, J=1.3 Hz, 1H), 7.18 (dd, J=8.5, 1.8 Hz, 1H), 2.35 (s, 3H), 2.18 (s, 3H), 2.04 (s, 3H).

<Example 32> Synthesis of 5-fluoro-N-(5-hydroxy-3,4,6-trimethylpyridin-2-yl)-1H-indole-2-carboxamide (Formula X-06)

The target compound was prepared according to the method of general preparation procedure 2 of examples.
$^1$H-NMR (($CD_3$)$_2$SO) δ 11.77 (s, 1H), 10.30 (s, 1H), 8.62 (s, 1H), 7.43 (dt, J=6.6, 3.0 Hz, 2H), 7.35 (d, J=1.5 Hz, 1H), 7.07 (td, J=9.4, 2.5 Hz, 1H), 2.35 (s, 3H), 2.18 (s, 3H), 2.04 (s, 3H).

<Example 33> Synthesis of 5-bromo-N-(5-hydroxy-3,4,6-trimethylpyridin-2-yl)-1H-indole-2-carboxamide (Formula X-07)

The target compound was prepared according to the method of general preparation procedure 2 of examples.
$^1$H-NMR (($CD_3$)$_2$SO) δ 11.85 (s, 1H), 10.31 (s, 1H), 8.61 (s, 1H), 7.87 (d, J=1.2 Hz, 1H), 7.35 (dd, J=9.5, 7.8 Hz, 3H), 2.35 (s, 3H), 2.18 (s, 3H), 2.05 (s, 3H).

<Example 34> Synthesis of 5-chloro-N-(5-hydroxy-3,4,6-trimethylpyridin-2-yl)-1H-indole-2-carboxamide (Formula X-08)

The target compound was prepared according to the method of general preparation procedure 2 of examples.
$^1$H-NMR (($CD_3$)$_2$SO) δ 11.90 (s, 1H), 10.37 (s, 1H), 8.67 (s, 1H), 7.73 (d, J=1.8 Hz, 1H), 7.44 (d, J=8.8 Hz, 1H), 7.35 (s, 1H), 7.20 (dd, J=8.8, 2.0 Hz, 1H), 2.34 (s, 3H), 2.17 (s, 3H), 2.04 (s, 3H).

<Example 35> Synthesis of N-(5-hydroxy-3,4,6-trimethylpyridin-2-yl)-5-methyl-1H-indole-2-carboxamide (Formula X-09)

The target compound was prepared according to the method of general preparation procedure 2 of examples.
$^1$H-NMR (($CD_3$)$_2$SO) δ 11.54 (d, J=1.1 Hz, 1H), 10.22 (s, 1H), 8.63 (s, 1H), 7.41 (s, 1H), 7.30 (dd, J=12.6, 4.9 Hz, 2H), 7.03 (dd, J=8.4, 1.4 Hz, 1H), 2.36 (d, J=8.1 Hz, 6H), 2.17 (s, 3H), 2.04 (s, 3H).

<Example 36> Synthesis of N-(5-hydroxy-3,4,6-trimethylpyridin-2-yl)-5-(trifluoromethyl)-1H-indole-2-carboxamide (Formula X-10)

The target compound was prepared according to the method of general preparation procedure 2 of examples.

$^1$H-NMR ((CD$_3$)$_2$SO) δ 12.13 (s, 1H), 10.44 (s, 1H), 8.64 (s, 1H), 8.10 (s, 1H), 7.62 (d, J=8.7 Hz, 1H), 7.59-7.44 (m, 2H), 2.35 (s, 3H), 2.18 (s, 3H), 2.05 (s, 3H).

<Example 37> Synthesis of N-(5-hydroxy-3,4,6-trimethylpyridin-2-yl)-5-(trifluoromethoxy)-1H-indole-2-carboxamide (Formula X-11)

The target compound was prepared according to the method of general preparation procedure 2 of examples.
$^1$H-NMR ((CD$_3$)$_2$SO) δ 12.08 (s, 1H), 10.74 (s, 1H), 9.31 (s, 1H), 7.71 (s, 1H), 7.53 (d, J=9.2 Hz, 2H), 7.21 (d, J=8.8 Hz, 1H), 2.44 (s, 3H), 2.26 (s, 3H), 2.11 (s, 3H).

<Example 38> Synthesis of N-(5-hydroxy-3,4,6-trimethylpyridin-2-yl)-6-methoxy-1H-indole-2-carboxamide (Formula X-12)

The target compound was prepared according to the method of general preparation procedure 2 of examples.
$^1$H-NMR ((CD$_3$)$_2$SO) δ 11.42 (s, 1H), 10.07 (s, 1H), 8.54 (s, 1H), 7.51 (d, J=8.7 Hz, 1H), 7.28 (s, 1H), 6.90 (s, 1H), 6.71 (dd, J=8.7, 2.3 Hz, 1H), 3.78 (s, 3H), 2.34 (s, 3H), 2.18 (s, 3H), 2.04 (s, 3H).

<Example 39> Synthesis of N-(5-hydroxy-3,4,6-trimethylpyridin-2-yl)-5-methoxy-1H-indole-2-carboxamide (Formula X-13)

The target compound was prepared according to the method of general preparation procedure 2 of examples.
$^1$H-NMR ((CD$_3$)$_2$SO) δ 11.85 (s, 1H), 10.31 (s, 1H), 8.61 (s, 1H), 7.87 (d, J=1.2 Hz, 1H), 7.35 (dd, J=9.5, 7.8 Hz, 3H), 2.35 (s, 3H), 2.18 (s, 3H), 2.05 (s, 3H).

<Example 40> Synthesis of N-(5-hydroxy-3,4,6-trimethylpyridin-2-yl)-5,6-dimethoxy-1H-indole-2-carboxamide (Formula X-14)

The target compound was prepared according to the method of general preparation procedure 2 of examples.
$^1$H-NMR ((CD$_3$)$_2$SO) δ 11.33 (s, 1H), 10.04 (s, 1H), 8.55 (s, 1H), 7.24 (d, J=1.7 Hz, 1H), 7.09 (s, 1H), 6.90 (s, 1H), 3.77 (s, 6H), 2.34 (s, 3H), 2.17 (s, 3H), 2.04 (s, 3H).

<Example 41> Synthesis of N-(5-hydroxy-3,4,6-trimethylpyridin-2-yl)benzofuran-2-carboxamide (Formula X-15)

The target compound was prepared according to the method of general preparation procedure 2 of examples.
$^1$H-NMR ((CD$_3$)$_2$SO) δ 10.44 (s, 1H), 8.66 (s, 1H), 7.81 (d, J=7.7 Hz, 1H), 7.76-7.65 (m, 2H), 7.53-7.45 (m, 1H), 7.35 (t, J=7.5 Hz, 1H), 2.34 (s, 3H), 2.17 (s, 3H), 2.04 (s, 3H).

<Example 42> Synthesis of 5-chloro-N-(5-hydroxy-3,4,6-trimethylpyridin-2-yl)benzofuran-2-carboxamide (Formula X-16)

The target compound was prepared according to the method of general preparation procedure 2 of examples.
$^1$H-NMR ((CD$_3$)$_2$SO) δ 10.75 (s, 1H), 9.28-9.04 (m, 1H), 7.93 (d, J=2.2 Hz, 1H), 7.75 (d, J=9.2 Hz, 2H), 7.53 (dd, J=8.7, 2.2 Hz, 2H), 2.41 (s, 3H), 2.24 (s, 3H), 2.10 (s, 3H).

<Example 43> Synthesis of 5-bromo-N-(5-hydroxy-3,4,6-trimethylpyridin-2-yl)benzofuran-2-carboxamide (Formula X-17)

The target compound was prepared according to the method of general preparation procedure 2 of examples.
$^1$H-NMR ((CD$_3$)$_2$SO) δ 10.44 (s, 1H), 8.66 (s, 1H), 7.81 (d, J=7.7 Hz, 1H), 7.76-7.65 (m, 2H), 7.53-7.45 (m, 1H), 7.35 (t, J=7.5 Hz, 1H), 2.34 (s, 3H), 2.17 (s, 3H), 2.04 (s, 3H).

<Example 44> Synthesis of N-(5-hydroxy-3,4,6-trimethylpyridin-2-yl)-7-methoxybenzofuran-2-carboxamide (Formula X-18)

The target compound was prepared according to the method of general preparation procedure 2 of examples.
$^1$H-NMR ((CD$_3$)$_2$SO) δ 10.53 (s, 1H), 8.90 (d, J=2.5 Hz, 1H), 7.76 (s, 1H), 7.40-7.22 (m, 2H), 7.09 (d, J=7.6 Hz, 1H), 3.98 (s, 3H), 2.37 (s, 3H), 2.20 (s, 3H), 2.07 (s, 3H).

<Example 45> Synthesis of N-(5-hydroxy-3,4,6-trimethylpyridin-2-yl)-3-methylbenzofuran-2-carboxamide (Formula X-19)

The target compound was prepared according to the method of general preparation procedure 2 of examples.
$^1$H-NMR ((CD$_3$)$_2$SO) δ 10.10 (s, 1H), 8.58 (s, 1H), 7.77 (d, J=7.7 Hz, 1H), 7.62 (d, J=8.2 Hz, 1H), 7.55-7.46 (m, 1H), 7.41-7.33 (m, 1H), 2.55 (s, 3H), 2.33 (s, 3H), 2.17 (s, 3H), 2.06 (s, 3H).

<Example 46> Synthesis of N-(5-hydroxy-3,4,6-trimethylpyridin-2-yl)benzo[b]thiophene-2-carboxamide (Formula X-20)

The target compound was prepared according to the method of general preparation procedure 2 of examples.
$^1$H-NMR ((CD$_3$)$_2$SO) δ 11.33 (s, 1H), 10.17-9.79 (m, 1H), 8.55 (s, 1H), 8.04 (dd, J=14.2, 7.7 Hz, 2H), 7.62-7.38 (m, 2H), 2.53 (s, 3H), 2.33 (s, 3H), 2.20 (s, 3H).

<Example 47> Synthesis of 3-chloro-N-(5-hydroxy-3,4,6-trimethylpyridin-2-yl)benzo[b]thiophene-2-carboxamide (Formula X-21)

The target compound was prepared according to the method of general preparation procedure 2 of examples.
$^1$H-NMR ((CD$_3$)$_2$SO) δ 10.26 (s, 1H), 8.67 (s, 1H), 8.13 (dd, J=6.2, 3.0 Hz, 1H), 7.92 (dd, J=6.3, 3.0 Hz, 1H), 7.61 (dd, J=6.1, 3.2 Hz, 2H), 2.33 (s, 3H), 2.18 (s, 3H), 2.11 (s, 3H).

<Example 48> Synthesis of 3-bromo-N-(5-hydroxy-3,4,6-trimethylpyridin-2-yl)benzo[b]thiophene-2-carboxamide (Formula X-22)

The target compound was prepared according to the method of general preparation procedure 2 of examples.
$^1$H-NMR ((CD$_3$)$_2$SO) δ 10.37 (s, 1H), 8.63 (s, 1H), 8.19-8.09 (m, 1H), 7.94-7.84 (m, 1H), 7.60 (dd, J=6.1, 3.1 Hz, 2H), 2.33 (s, 3H), 2.18 (s, 3H), 2.12 (s, 3H).

<Example 49> Synthesis of 3-chloro-N-(5-hydroxy-3,4,6-trimethylpyridin-2-yl)-6-methylbenzo[b]thiophene-2-carboxamide (Formula X-23)

The target compound was prepared according to the method of general preparation procedure 2 of examples.

¹H-NMR ((CD₃)₂SO) δ 10.16 (s, 1H), 8.64 (s, 1H), 7.92 (s, 1H), 7.81 (d, J=8.3 Hz, 1H), 7.44 (dd, J=8.3, 0.9 Hz, 1H), 3.32 (s, 3H), 2.34 (s, 3H), 2.19 (s, 3H), 2.12 (s, 3H).

<Example 50> Synthesis of 3-chloro-6-fluoro-N-(5-hydroxy-3,4,6-trimethylpyridin-2-yl)benzo[b]thiophene-2-carboxamide (Formula X-24)

The target compound was prepared according to the method of general preparation procedure 2 of examples.
¹H-NMR ((CD₃)₂SO) δ 10.40 (s, 1H), 9.12 (s, 1H), 8.10 (dd, J=9.1, 2.3 Hz, 1H), 7.96 (dd, J=9.0, 5.1 Hz, 1H), 7.49 (td, J=9.0, 2.4 Hz, 1H), 2.40 (s, 3H), 2.23 (s, 3H), 2.14 (s, 3H).

<Example 51> Synthesis of 3,6-dichloro-N-(5-hydroxy-3,4,6-trimethylpyridin-2-yl)benzo[b]thiophene-2-carboxamide (Formula X-25)

The target compound was prepared according to the method of general preparation procedure 2 of examples.
¹H-NMR ((CD₃)₂SO) δ 10.27 (s, 1H), 8.65 (s, 1H), 8.34 (d, J=1.6 Hz, 1H), 7.91 (d, J=8.7 Hz, 1H), 7.63 (dd, J=8.7, 1.9 Hz, 1H), 2.32 (s, 3H), 2.18 (s, 3H), 2.10 (s, 3H).

<Example 52> Synthesis of 3-chloro-N-(5-hydroxy-3,4,6-trimethylpyridin-2-yl)-6-methoxybenzo[b]thiophene-2-carboxamide (Formula X-26)

The target compound was prepared according to the method of general preparation procedure 2 of examples.
¹H-NMR ((CD₃)₂SO) δ 10.16 (s, 1H), 8.64 (s, 1H), 7.92 (s, 1H), 7.81 (d, J=8.3 Hz, 1H), 7.44 (dd, J=8.3, 0.9 Hz, 1H), 3.32 (s, 3H), 2.34 (s, 3H), 2.19 (s, 3H), 2.12 (s, 3H).

<Example 53> Synthesis of 3-chloro-6-fluoro-N-(5-methoxy-3,4,6-trimethylpyridin-2-yl)benzo[b]thiophene-2-carboxamide (Formula XI-01)

A 1:1 mixed solvent (2 mL) of THF and water was added to compound X-24 (20 mg), to which K₂CO₃ (76 mg) and CH₃I (34 μL) were sequentially added. The reaction mixture was stirred at room temperature for 24 hours and then concentrated under reduced pressure. The residue was diluted with CH₂Cl₂ and water, and the aqueous layer was extracted several times with CH₂Cl₂. The CH₂Cl₂ solution was dried over anhydrous MgSO₄, filtered, and concentrated under reduced pressure. The residue was purified by silica gel column chromatography (CH₂Cl₂:MeOH=40:1) to give compound XI-01 (13 mg) as a white solid.
¹H-NMR ((CD₃)₂SO) δ 10.48 (s, 1H), 8.11 (dd, J=9.1, 2.3 Hz, 1H), 8.00-7.92 (m, 1H), 7.50 (td, J=9.0, 2.4 Hz, 1H), 3.69 (s, 3H), 2.37 (s, 3H), 2.23 (s, 3H), 2.12 (s, 3H).

<Example 54> Synthesis of 3-chloro-6-fluoro-N-(5-methoxy-3,4,6-trimethylpyridin-2-yl)-N-methylbenzo[b]thiophene-2-carboxamide (Formula XI-02)

K₂CO₃ (17 mg) and CH₃I (13 μL) were sequentially added to a DMF (1 mL) solution of compound X-24 (15 mg). The reaction mixture was stirred at room temperature for 24 hours. The reaction mixture was diluted with EtOAc and washed with water and saturated brine. The EtOAc solution was dried over anhydrous MgSO₄, filtered, and concentrated under reduced pressure. The residue was purified by silica gel column chromatography (EtOAc: Hexanes=3:7) to give compound XI-02 (10 mg) as a yellow solid.
¹H-NMR ((CD₃)₂SO) δ 7.90 (dd, J=9.1, 2.3 Hz, 1H), 7.78 (dd, J=8.9, 5.1 Hz, 1H), 7.36 (td, J=9.0, 2.3 Hz, 1H), 3.59 (s, 3H), 3.25 (s, 3H), 2.24 (s, 4H), 2.13 (s, 3H), 2.10 (s, 3H).

General Preparation Procedure 3 of Examples

According to the preparation method of reaction formula C below, the compounds of examples 55-59 (Compounds XI-03~ XI-07) were prepared.

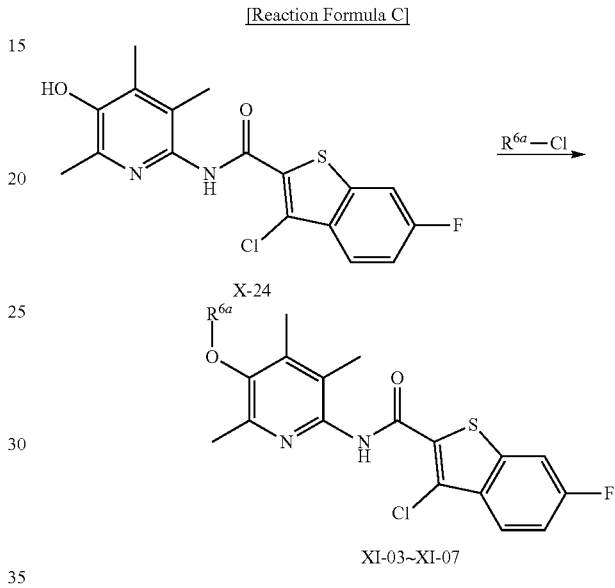

[Reaction Formula C]

In reaction formula C above,
R⁶ᵃ is —(CH₂)mC(=O)NH(CH₂)nRᵇ, and m, n and Rᵇ are as defined in this specification.
NaH (0.3 mmol) and N-substituted-2-chloroacetamide (0.2 mmol) were sequentially added to a DMF (1 mL) solution of compound X-24 (0.1 mmol), followed by stirring at room temperature until the compound X-24 disappeared on TLC. The reaction mixture was diluted with EtOAc and washed with water and saturated brine. The EtOAc solution was dried over anhydrous MgSO₄, filtered, and concentrated under reduced pressure. The obtained residue was purified by silica gel column chromatography to give compounds XI-03~XI-07.

<Example 55> Synthesis of 3-chloro-6-fluoro-N-(5-(2-(isopropylamino)-2-oxoethoxy)-3,4,6-trimethylpyridin-2-yl)benzo[b]thiophene-2-carboxamide (Formula XI-03)

The target compound was prepared according to the method of general preparation procedure 3 of examples.
¹H-NMR ((CD₃)₂SO) δ 10.49 (s, 1H), 8.11 (dd, J=9.1, 2.3 Hz, 1H), 8.04 (d, J=8.1 Hz, 1H), 7.96 (dd, J=9.0, 5.1 Hz, 1H), 7.50 (td, J=9.0, 2.4 Hz, 1H), 4.21 (s, 2H), 4.01 (tt, J=13.2, 6.6 Hz, 1H), 2.38 (s, 3H), 2.25 (s, 3H), 2.12 (s, 3H), 1.14 (s, 3H), 1.13 (s, 3H).

<Example 56> Synthesis of 3-chloro-N-(5-(2-(cyclopropylamino)-2-oxoethoxy)-3,4,6-trimethylpyridin-2-yl)-6-fluorobenzo[b]thiophene-2-carboxamide (Formula XI-04)

The target compound was prepared according to the method of general preparation procedure 3 of examples.

$^1$H-NMR (CDCl$_3$) δ 9.19 (s, 1H), 7.89 (dd, J=9.0, 4.9 Hz, 1H), 7.53 (dd, J=8.3, 2.1 Hz, 1H), 7.33-7.22 (m, 1H), 6.86 (s, 1H), 4.25 (s, 2H), 2.90-2.82 (m, 1H), 2.48 (s, 3H), 2.28 (s, 3H), 2.22 (s, 3H), 0.92-0.84 (m, 2H), 0.68-0.61 (m, 2H).

<Example 57> Synthesis of 3-chloro-N-(5-(2-(cyclohexylamino)-2-oxoethoxy)-3,4,6-trimethylpyridin-2-yl)-6-fluorobenzo[b]thiophene-2-carboxamide (Formula XI-05)

The target compound was prepared according to the method of general preparation procedure 3 of examples.

$^1$H-NMR (CDCl$_3$) δ 9.25 (s, 1H), 7.90 (dd, J=9.0, 4.9 Hz, 1H), 7.54 (dd, J=8.3, 2.2 Hz, 1H), 7.32-7.23 (m, 1H), 6.67 (d, J=8.3 Hz, 1H), 4.26 (s, 2H), 3.92 (dt, J=10.5, 7.4 Hz, 1H), 2.51 (s, 3H), 2.30 (s, 3H), 2.23 (s, 3H), 2.04-1.97 (m, 2H), 1.81-1.72 (m, 2H), 1.66 (dd, J=9.2, 3.8 Hz, 1H), 1.42 (ddd, J=15.1, 9.0, 5.8 Hz, 2H), 1.34-1.26 (m, 2H), 1.21 (d, J=3.6 Hz, 1H).

<Example 58> Synthesis of N-(5-(2-(benzylamino)-2-oxoethoxy)-3,4,6-trimethylpyridin-2-yl)-3-chloro-6-fluorobenzo[b]thiophene-2-carboxamide (Formula XI-06)

The target compound was prepared according to the method of general preparation procedure 3 of examples.

$^1$H-NMR ((CD$_3$)$_2$SO) δ 10.50 (s, 1H), 8.83 (t, J=6.2 Hz, 1H), 8.11 (dd, J=9.1, 2.3 Hz, 1H), 7.96 (dd, J=9.0, 5.1 Hz, 1H), 7.50 (td, J=9.0, 2.4 Hz, 1H), 7.37-7.29 (m, 4H), 7.28-7.22 (m, 1H), 4.40 (d, J=6.1 Hz, 2H), 4.33 (s, 2H), 2.39 (s, 3H), 2.26 (s, 3H), 2.12 (s, 3H).

<Example 59> Synthesis of 3-chloro-6-fluoro-N-(3,4,6-trimethyl-5-(2-oxo-2-(phenylamino)ethoxy)pyridin-2-yl)benzo[b]thiophene-2-carboxamide (Formula XI-07)

The target compound was prepared according to the method of general preparation procedure 3 of examples.

$^1$H-NMR ((CD$_3$)$_2$SO) δ 10.53 (s, 1H), 10.14 (s, 1H), 8.13 (dd, J=9.0, 2.3 Hz, 1H), 7.98 (dd, J=8.9, 5.1 Hz, 1H), 7.76-7.70 (m, 2H), 7.52 (td, J=9.0, 2.4 Hz, 1H), 7.40-7.33 (m, 2H), 7.15-7.09 (m, 1H), 4.49 (s, 2H), 2.45 (s, 3H), 2.32 (s, 3H), 2.16 (s, 3H).

General Preparation Procedure 4 of Examples

According to the preparation method of reaction formula D below, the compounds of examples 60-68 (Compounds XI-08~ XI-16) were prepared.

[Reaction Formula D]

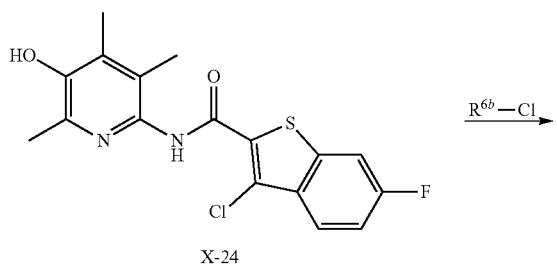

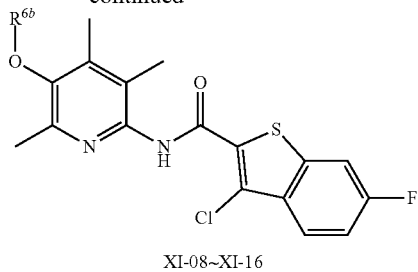

In reaction formula D above, $R^{6b}$ is —C(=O)R$^c$, and R$^c$ is as defined in this specification.

Method (1): Et$_3$N (0.2 mmol) and acid chloride (0.1 mmol) were sequentially added to the CH$_2$Cl$_2$ (1 mL) suspension of compound X-24 (0.1 mmol), followed by stirring at room temperature until the compound X-24 disappeared on TLC. The reaction mixture was diluted with CH$_2$Cl$_2$ and washed with water, saturated NaHCO$_3$ solution, water, and saturated brine in that order. The CH$_2$Cl$_2$ solution was dried over anhydrous MgSO$_4$, filtered, and concentrated under reduced pressure. The obtained residue was purified by silica gel column chromatography to give compounds XI-08~XI-16.

Method (2): EDCI (0.15 mmol), HOBt (0.15 mmol) and Et$_3$N (0.25 mmol) were added to a DMF (1 mL) solution of compound X-24 (0.1 mmol). Carboxylic acid (0.2 mmol) was added thereto, and the reaction mixture was stirred at room temperature until the compound X-24 disappeared on TLC. The reaction mixture was diluted with CH$_2$Cl$_2$ and washed with water and saturated brine in that order. The CH$_2$Cl$_2$ solution was dried over anhydrous MgSO$_4$, filtered, and concentrated under reduced pressure. The obtained residue was purified by silica gel column chromatography to give compounds XI-08~XI-16.

<Example 60> Synthesis of 6-(3-chloro-6-fluorobenzo[b]thiophene-2-carboxamido)-2,4,5-trimethylpyridin-3-yl benzoate (Formula XI-08)

The target compound was prepared according to the method (1) of general preparation procedure 4 of examples.

$^1$H-NMR ((CD$_3$)$_2$SO) δ 10.65 (s, 1H), 8.26-8.21 (m, 2H), 8.12 (dd, J=9.1, 2.3 Hz, 1H), 7.98 (dd, J=9.0, 5.1 Hz, 1H), 7.84-7.78 (m, 1H), 7.70-7.63 (m, 2H), 7.51 (td, J=9.0, 2.4 Hz, 1H), 2.28 (s, 3H), 2.19 (s, 3H), 2.15 (s, 3H).

<Example 61> Synthesis of 6-(3-chloro-6-fluorobenzo[b]thiophene-2-carboxamido)-2,4,5-trimethylpyridin-3-yl 4-fluorobenzoate (Formula XI-09)

The target compound was prepared according to the method (1) of general preparation procedure 4 of examples.

$^1$H-NMR (CDCl$_3$) δ 9.35 (s, 1H), 8.36-8.20 (m, 2H), 7.91 (dd, J=9.0, 4.9 Hz, 1H), 7.54 (dd, J=8.3, 2.1 Hz, 1H), 7.28 (dd, J=8.9, 2.3 Hz, 1H), 7.26-7.20 (m, 2H), 2.44 (s, 3H), 2.28 (s, 3H), 2.23 (s, 3H).

<Example 62> Synthesis of 6-(3-chloro-6-fluorobenzo[b]thiophene-2-carboxamido)-2,4,5-trimethylpyridin-3-yl 3-methoxybenzoate (Formula XI-10)

The target compound was prepared according to the method (1) of general preparation procedure 4 of examples.

¹H-NMR (CDCl₃) δ 9.21 (s, 1H), 7.89 (dd, J=9.0, 5.0 Hz, 1H), 7.84 (d, J=7.8 Hz, 1H), 7.71 (dd, J=2.4, 1.5 Hz, 1H), 7.53 (dd, J=8.3, 2.2 Hz, 1H), 7.45 (t, J=8.0 Hz, 1H), 7.31-7.13 (m, 3H), 3.89 (s, 3H), 2.42 (s, 3H), 2.26 (s, 3H), 2.21 (s, 3H).

<Example 63> Synthesis of 6-(3-chloro-6-fluorobenzo[b]thiophene-2-carboxamido)-2,4,5-trimethylpyridin-3-yl 4-methoxybenzoate (Formula XI-11)

The target compound was prepared according to the method (1) of general preparation procedure 4 of examples.
¹H-NMR ((CD₃)₂SO) δ 10.63 (s, 1H), 8.21-8.15 (m, 2H), 8.12 (dd, J=9.1, 2.4 Hz, 1H), 7.97 (dd, J=8.9, 5.1 Hz, 1H), 7.51 (td, J=9.0, 2.4 Hz, 1H), 7.21-7.14 (m, 2H), 3.90 (s, 3H), 2.26 (s, 3H), 2.18 (s, 3H), 2.13 (s, 3H).

<Example 64> Synthesis of 6-(3-chloro-6-fluorobenzo[b]thiophene-2-carboxamido)-2,4,5-trimethylpyridin-3-yl 5-fluoropicolinate (Formula XI-12)

The target compound was prepared according to the method (2) of general preparation procedure 4 of examples.
¹H-NMR ((CD₃)₂SO) δ 10.66 (s, 1H), 8.88 (d, J=2.9 Hz, 1H), 8.45 (dd, J=8.8, 4.5 Hz, 1H), 8.13 (dd, J=9.1, 2.3 Hz, 1H), 8.05 (td, J=8.6, 2.9 Hz, 1H), 7.98 (dd, J=9.0, 5.1 Hz, 1H), 7.51 (td, J=9.0, 2.4 Hz, 1H), 2.28 (s, 3H), 2.20 (s, 3H), 2.16 (s, 3H).

<Example 65> Synthesis of 6-(3-chloro-6-fluorobenzo[b]thiophene-2-carboxamido)-2,4,5-trimethylpyridin-3-yl 6-fluoronicotinate (Formula XI-13)

The target compound was prepared according to the method (2) of general preparation procedure 4 of examples.
¹H-NMR ((CD₃)₂SO) δ 10.66 (s, 1H), 9.12 (d, J=2.5 Hz, 1H), 8.79-8.73 (m, 1H), 8.13 (dd, J=9.1, 2.3 Hz, 1H), 7.98 (dd, J=9.0, 5.1 Hz, 1H), 7.55-7.47 (m, 2H), 2.29 (s, 3H), 2.20 (s, 3H), 2.17 (s, 3H).

<Example 66> Synthesis of 6-(3-chloro-6-fluorobenzo[b]thiophene-2-carboxamido)-2,4,5-trimethylpyridin-3-yl 5-chloropicolinate (Formula XI-14)

The target compound was prepared according to the method (2) of general preparation procedure 4 of examples.
¹H-NMR ((CD₃)₂SO) δ 10.66 (s, 1H), 8.93 (dd, J=2.4, 0.6 Hz, 1H), 8.35 (dd, J=8.4, 0.6 Hz, 1H), 8.27 (dd, J=8.4, 2.4 Hz, 1H), 8.12 (dd, J=9.1, 2.3 Hz, 1H), 7.98 (dd, J=9.0, 5.1 Hz, 1H), 7.51 (td, J=9.0, 2.4 Hz, 1H), 2.28 (s, 3H), 2.19 (s, 3H), 2.16 (s, 3H).

<Example 67> Synthesis of 6-(3-chloro-6-fluorobenzo[b]thiophene-2-carboxamido)-2,4,5-trimethylpyridin-3-yl 6-chloropicolinate (Formula XI-15)

The target compound was prepared according to the method (1) of general preparation procedure 4 of examples.
¹H-NMR ((CD₃)₂SO) δ 10.66 (s, 1H), 9.22 (dd, J=2.5, 0.6 Hz, 1H), 8.60 (dd, J=8.4, 2.5 Hz, 1H), 8.12 (dd, J=9.1, 2.3 Hz, 1H), 7.98 (dd, J=9.0, 5.1 Hz, 1H), 7.83 (dd, J=8.4, 0.6 Hz, 1H), 7.51 (td, J=9.0, 2.4 Hz, 1H), 2.29 (s, 3H), 2.20 (s, 3H), 2.16 (s, 3H).

<Example 68> Synthesis of 6-(3-chloro-6-fluorobenzo[b]thiophene-2-carboxamido)-2,4,5-trimethylpyridin-3-yl (3r,5r,7r)-adamantane-1-carboxylate (Formula XI-16)

The target compound was prepared according to the method (1) of general preparation procedure 4 of examples.
¹H-NMR ((CD₃)₂SO) δ 10.58 (s, 1H), 8.12 (dd, J=9.1, 2.3 Hz, 1H), 7.97 (dd, J=9.0, 5.1 Hz, 1H), 7.51 (td, J=9.0, 2.4 Hz, 1H), 2.20 (s, 3H), 2.15 (s, 3H), 2.07 (m, 12H), 1.76 (m, 6H).

<Example 69> Synthesis of 6-(3-chloro-6-fluorobenzo[b]thiophene-2-carboxamido)-2,4,5-trimethylpyridin-3-yl morpholine-4-carboxylate (Formula XI-17)

Compound X-24 (200 mg) and NaH (44 mg) were dissolved in DMF (1.8 mL), to which 1H-imidazol-1-yl-4-morpholinylmethanone (100 mg) was added, and the mixture was stirred at room temperature for 24 hours. The reaction solution was diluted with EtOAc and washed with water and saturated brine. The EtOAc solution was dried over anhydrous MgSO₄, filtered, and concentrated under reduced pressure. The residue was purified by column chromatography (CH₂Cl₂:MeOH=99:1) to give the target compound XI-17 (40 mg) as a yellow solid.
¹H-NMR ((CD₃)₂SO) δ 10.57 (s, 1H), 8.12 (dd, J=9.1, 2.3 Hz, 1H), 7.97 (dd, J=9.0, 5.1 Hz, 1H), 7.51 (td, J=9.0, 2.4 Hz, 1H), 3.68 (s, 6H), 3.45 (d, J=12.6 Hz, 2H), 2.26 (s, 3H), 2.15 (s, 3H), 2.12 (s, 3H).

The numbers, chemical structures and names of the compounds of the present invention prepared above are summarized in Table 1 below.

TABLE 1

| Number | Example | Structure | Name |
|---|---|---|---|
| IX-01 | 1 | 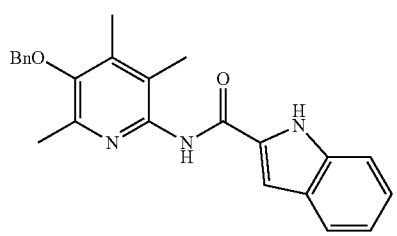 | N-(5-(benzyloxy)-3,4,6-trimethylpyridin-2-yl)-1H-indole-2-carboxamide |

TABLE 1-continued

| Number | Example | Structure | Name |
|---|---|---|---|
| IX-02 | 2 | 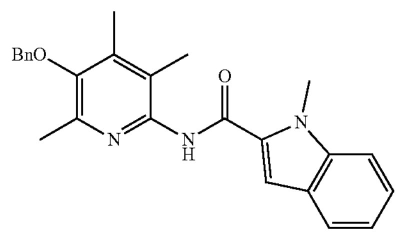 [SMILES: Cc1nc(NC(=O)c2cc3ccccc3n2C)c(C)c(C)c1OCc1ccccc1] | N-(5-(benzyloxy)-3,4,6-trimethylpyridin-2-yl)-1-methyl-1H-indole-2-carboxamide |
| IX-03 | 3 | 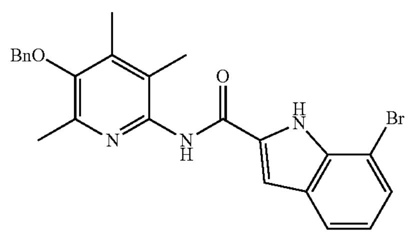 [SMILES: Cc1nc(NC(=O)c2cc3cccc(Br)c3[nH]2)c(C)c(C)c1OCc1ccccc1] | N-(5-(benzyloxy)-3,4,6-trimethylpyridin-2-yl)-7-bromo-1H-indole-2-carboxamide |
| IX-04 | 4 | 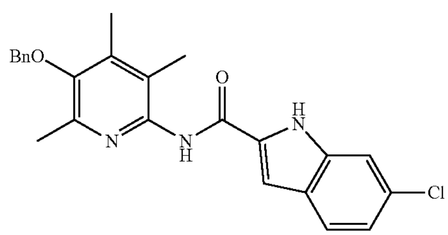 [SMILES: Cc1nc(NC(=O)c2cc3ccc(Cl)cc3[nH]2)c(C)c(C)c1OCc1ccccc1] | N-(5-(benzyloxy)-3,4,6-trimethylpyridin-2-yl)-6-chloro-1H-indole-2-carboxamide |
| IX-05 | 5 | 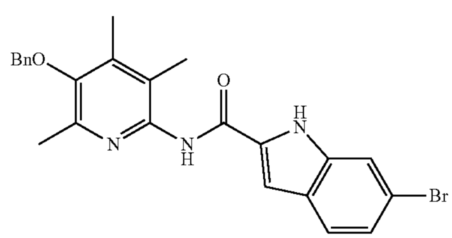 [SMILES: Cc1nc(NC(=O)c2cc3ccc(Br)cc3[nH]2)c(C)c(C)c1OCc1ccccc1] | N-(5-(benzyloxy)-3,4,6-trimethylpyridin-2-yl)-6-bromo-1H-indole-2-carboxamide |
| IX-06 | 6 | 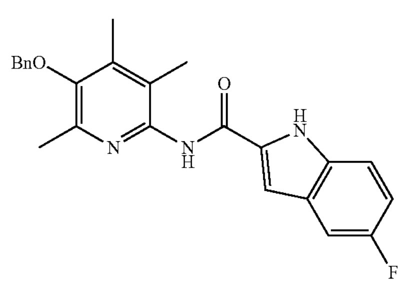 [SMILES: Cc1nc(NC(=O)c2cc3cc(F)ccc3[nH]2)c(C)c(C)c1OCc1ccccc1] | N-(5-(benzyloxy)-3,4,6-trimethylpyridin-2-yl)-5-fluoro-1H-indole-2-carboxamide |
| IX-07 | 7 | 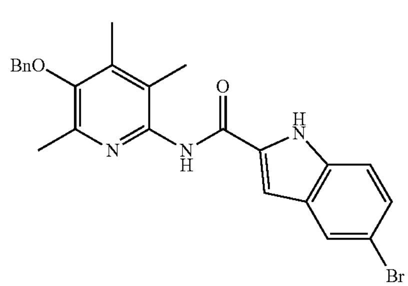 | N-(5-(benzyloxy)-3,4,6-trimethylpyridin-2-yl)-5-bromo-1H-indole-2-carboxamide |

TABLE 1-continued

| Number | Example | Structure | Name |
|---|---|---|---|
| IX-08 | 8 | 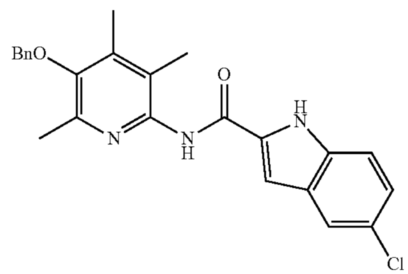 [SMILES: Cc1nc(NC(=O)c2cc3cc(Br)ccc3[nH]2)c(C)c(C)c1OCc1ccccc1] | N-(5-(benzyloxy)-3,4,6-trimethylpyridin-2-yl)-5-chloro-1H-indole-2-carboxamide |
| IX-09 | 9 | 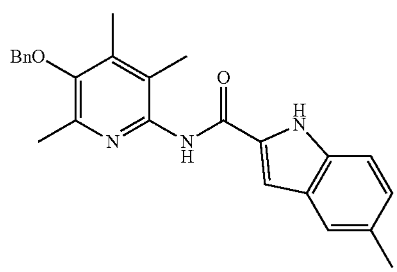 [SMILES: Cc1ccc2[nH]c(C(=O)Nc3nc(C)c(OCc4ccccc4)c(C)c3C)cc2c1] | N-(5-(benzyloxy)-3,4,6-trimethylpyridin-2-yl)-5-methyl-1H-indole-2-carboxamide |
| IX-10 | 10 | 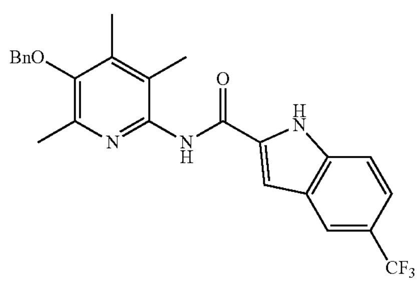 [SMILES: Cc1nc(NC(=O)c2cc3cc(C(F)(F)F)ccc3[nH]2)c(C)c(C)c1OCc1ccccc1] | N-(5-(benzyloxy)-3,4,6-trimethylpyridin-2-yl)-5-(trifluoromethyl)-1H-indole-2-carboxamide |
| IX-11 | 11 | 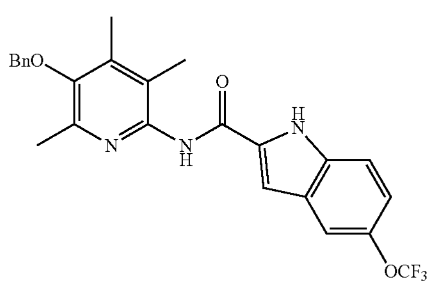 [SMILES: Cc1nc(NC(=O)c2cc3cc(OC(F)(F)F)ccc3[nH]2)c(C)c(C)c1OCc1ccccc1] | N-(5-(benzyloxy)-3,4,6-trimethylpyridin-2-yl)-5-(trifluoromethoxy)-1H-indole-2-carboxamide |
| IX-12 | 12 | 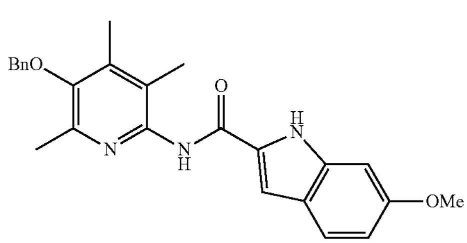 [SMILES: COc1ccc2cc(C(=O)Nc3nc(C)c(OCc4ccccc4)c(C)c3C)[nH]c2c1] | N-(5-(benzyloxy)-3,4,6-trimethylpyridin-2-yl)-6-methoxy-1H-indole-2-carboxamide |

TABLE 1-continued

| Number | Example | Structure | Name |
|---|---|---|---|
| IX-13 | 13 | 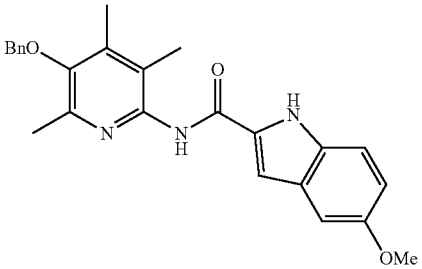 [SMILES: COc1ccc2[nH]c(C(=O)Nc3nc(C)c(OCc4ccccc4)c(C)c3C)cc2c1] | N-(5-(benzyloxy)-3,4,6-trimethylpyridin-2-yl)-5-methoxy-1H-indole-2-carboxamide |
| IX-14 | 14 | 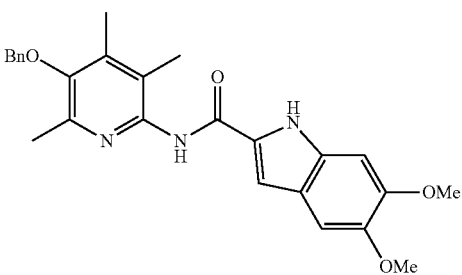 [SMILES: COc1cc2cc(C(=O)Nc3nc(C)c(OCc4ccccc4)c(C)c3C)[nH]c2cc1OC] | N-(5-(benzyloxy)-3,4,6-trimethylpyridin-2-yl)-5,6-dimethoxy-1H-indole-2-carboxamide |
| IX-15 | 15 | 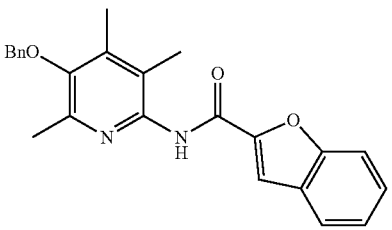 [SMILES: Cc1nc(NC(=O)c2cc3ccccc3o2)c(C)c(C)c1OCc1ccccc1] | N-(5-(benzyloxy)-3,4,6-trimethylpyridin-2-yl)benzofuran-2-carboxamide |
| IX-16 | 16 | 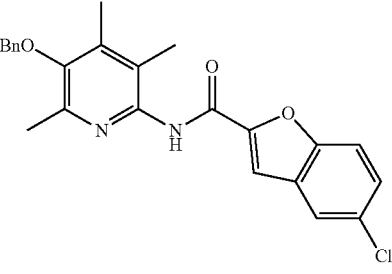 [SMILES: Cc1nc(NC(=O)c2cc3cc(Cl)ccc3o2)c(C)c(C)c1OCc1ccccc1] | N-(5-(benzyloxy)-3,4,6-trimethylpyridin-2-yl)-5-chlorobenzofuran-2-carboxamide |
| IX-17 | 17 | 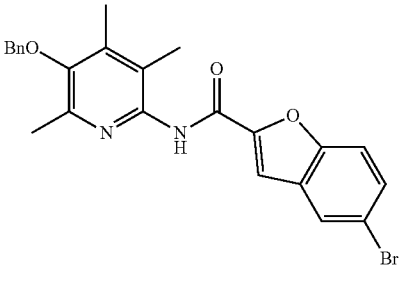 | N-(5-(benzyloxy)-3,4,6-trimethylpyridin-2-yl)-5-bromobenzofuran-2-carboxamide |
| IX-18 | 18 | 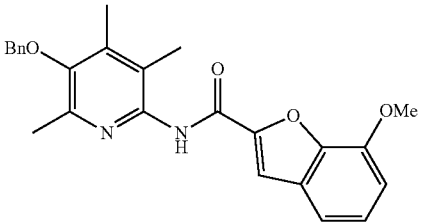 [SMILES: COc1cccc2cc(C(=O)Nc3nc(C)c(OCc4ccccc4)c(C)c3C)oc12] | N-(5-(benzyloxy)-3,4,6-trimethylpyridin-2-yl)-7-methoxybenzofuran-2-carboxamide |

TABLE 1-continued

| Number | Example | Structure | Name |
|---|---|---|---|
| IX-19 | 19 | 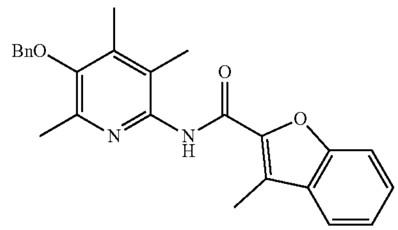 [SMILES: Cc1nc(NC(=O)c2oc3ccccc3c2C)c(C)c(C)c1OCc1ccccc1] | N-(5-(benzyloxy)-3,4,6-trimethylpyridin-2-yl)-3-methylbenzofuran-2-carboxamide |
| IX-20 | 20 | 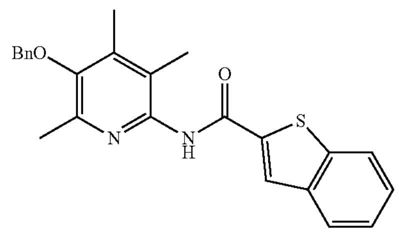 [SMILES: Cc1nc(NC(=O)c2cc3ccccc3s2)c(C)c(C)c1OCc1ccccc1] | N-(5-(benzyloxy)-3,4,6-trimethylpyridin-2-yl)benzo[bthiophene-2-carboxamide |
| IX-21 | 21 | 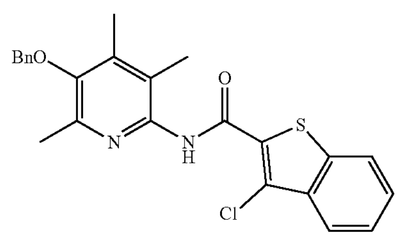 [SMILES: Cc1nc(NC(=O)c2sc3ccccc3c2Cl)c(C)c(C)c1OCc1ccccc1] | N-(5-(benzyloxy)-3,4,6-trimethylpyridin-2-yl)-3-chlorobenzo[b]thiophene-2-carboxamide |
| IX-22 | 22 | 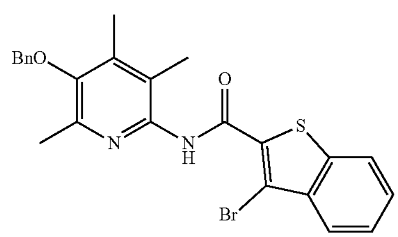 [SMILES: Cc1nc(NC(=O)c2sc3ccccc3c2Br)c(C)c(C)c1OCc1ccccc1] | N-(5-(benzyloxy)-3,4,6-trimethylpyridin-2-yl)-3-bromobenzo[b]thiophene-2-carboxamide |
| IX-23 | 23 | 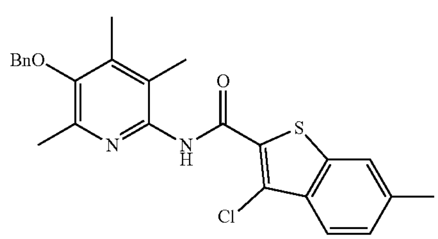 [SMILES: Cc1ccc2c(Cl)c(C(=O)Nc3nc(C)c(OCc4ccccc4)c(C)c3C)sc2c1] | N-(5-(benzyloxy)-3,4,6-trimethylpyridin-2-yl)-3-chloro-6-methylbenzo[b]thiophene-2-carboxamide |
| IX-24 | 24 | 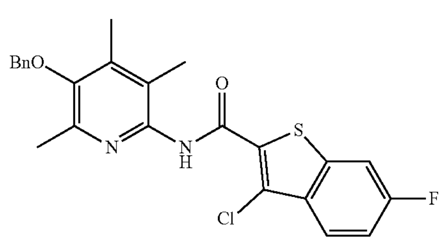 [SMILES: Cc1nc(NC(=O)c2sc3cc(F)ccc3c2Cl)c(C)c(C)c1OCc1ccccc1] | N-(5-(benzyloxy)-3,4,6-trimethylpyridin-2-yl)-3-chloro-6-fluorobenzo[b]thiophene-2-carboxamide |

TABLE 1-continued

| Number | Example | Structure | Name |
|---|---|---|---|
| IX-25 | 25 | 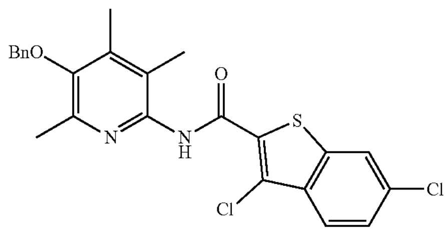 [SMILES: Cc1nc(NC(=O)c2sc3cc(Cl)ccc3c2Cl)c(C)c(C)c1OCc1ccccc1] | N-(5-(benzyloxy)-3,4,6-trimethylpyridin-2-yl)-3,6-dichlorobenzo[b]thiophene-2-carboxamide |
| IX-26 | 26 | 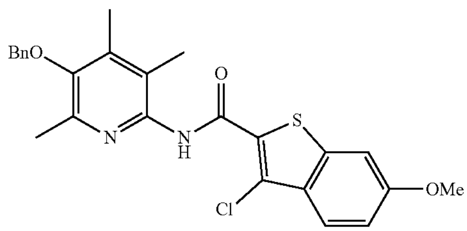 [SMILES: COc1ccc2c(Cl)c(C(=O)Nc3nc(C)c(OCc4ccccc4)c(C)c3C)sc2c1] | N-(5-(benzyloxy)-3,4,6-trimethylpyridin-2-yl)-3-chloro-6-methoxybenzo[b]thiophene-2-carboxamide |
| X-01 | 27 | 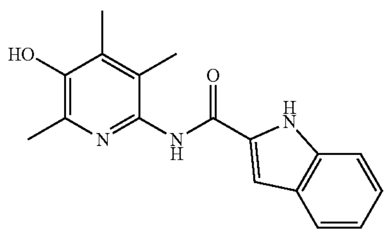 | N-(5-hydroxy-3,4,6-trimethylpyridin-2-yl)-1H-indole-2-carboxamide |
| X-02 | 28 | 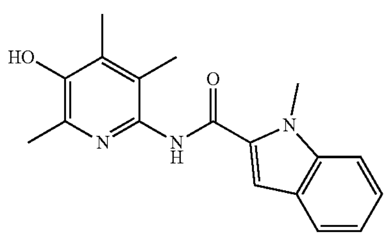 [SMILES: Cc1nc(NC(=O)c2cc3ccccc3n2C)c(C)c(C)c1O] | N-(5-hydroxy-3,4,6-trimethylpyridin-2-yl)-1-methyl-1H-indole-2-carboxamide |
| X-03 | 29 | 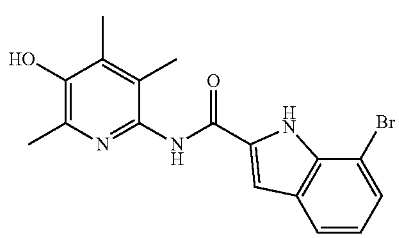 [SMILES: Cc1nc(NC(=O)c2cc3cccc(Br)c3[nH]2)c(C)c(C)c1O] | 7-bromo-N-(5-hydroxy-3,4,6-trimethylpyridin-2-yl)-1H-indole-2-carboxamide |
| X-04 | 30 | 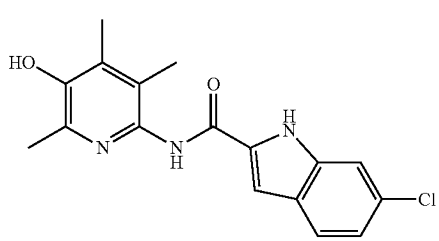 [SMILES: Cc1nc(NC(=O)c2cc3ccc(Br)cc3[nH]2)c(C)c(C)c1O] | 6-chloro-N-(5-hydroxy-3,4,6-trimethylpyridin-2-yl)-1H-indole-2-carboxamide |

TABLE 1-continued

| Number | Example | Structure | Name |
|---|---|---|---|
| X-05 | 31 | 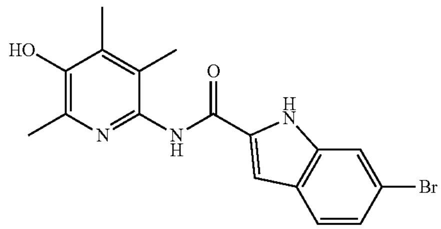 | 6-bromo-N-(5-hydroxy-3,4,6-trimethylpyridin-2-yl)-1H-indole-2-carboxamide |
| X-06 | 32 | 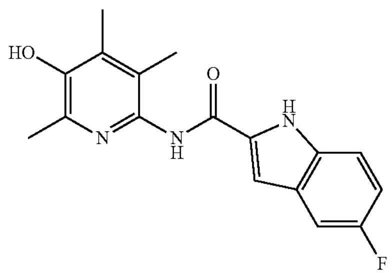 [SMILES: Cc1nc(NC(=O)c2cc3cc(F)ccc3[nH]2)c(C)c(C)c1O] | 5-fluoro-N-(5-hydroxy-3,4,6-trimethylpyridin-2-yl)-1H-indole-2-carboxamide |
| X-07 | 33 | 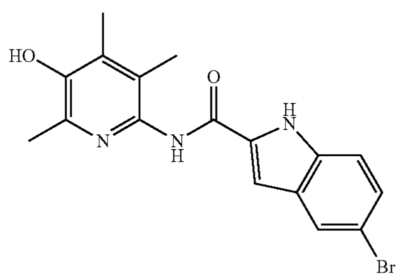 [SMILES: Cc1nc(NC(=O)c2cc3cc(Br)ccc3[nH]2)c(C)c(C)c1O] | 5-bromo-N-(5-hydroxy-3,4,6-trimethylpyridin-2-yl)-1H-indole-2-carboxamide |
| X-08 | 34 | 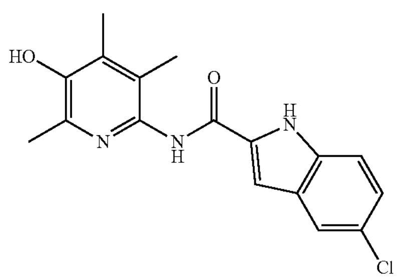 [SMILES: Cc1nc(NC(=O)c2cc3cc(Cl)ccc3[nH]2)c(C)c(C)c1O] | 5-chloro-N-(5-hydroxy-3,4,6-trimethylpyridin-2-yl)-1H-indole-2-carboxamide |
| X-09 | 35 | 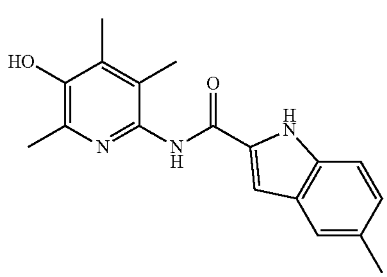 [SMILES: Cc1ccc2[nH]c(C(=O)Nc3nc(C)c(O)c(C)c3C)cc2c1] | N-(5-hydroxy-3,4,6-trimethylpyridin-2-yl)-5-methyl-1H-indole-2-carboxamide |

TABLE 1-continued

| Number | Example | Structure | Name |
|---|---|---|---|
| X-10 | 36 | 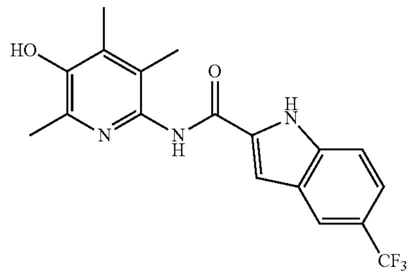 [SMILES: Cc1nc(NC(=O)c2cc3cc(C(F)(F)F)ccc3[nH]2)c(C)c(C)c1O] | N-(5-hydroxy-3,4,6-trimethylpyridin-2-yl)-5-(trifluoromethyl)-1H-indole-2-carboxamide |
| X-11 | 37 | 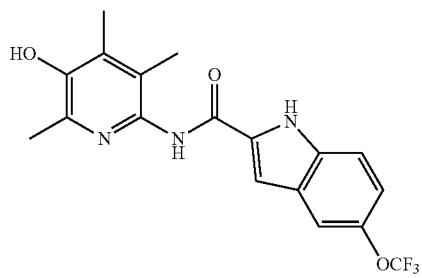 [SMILES: Cc1nc(NC(=O)c2cc3cc(OC(F)(F)F)ccc3[nH]2)c(C)c(C)c1O] | N-(5-hydroxy-3,4,6-trimethylpyridin-2-yl)-5-(trifluoromethoxy)-1H-indole-2-carboxamide |
| X-12 | 38 | 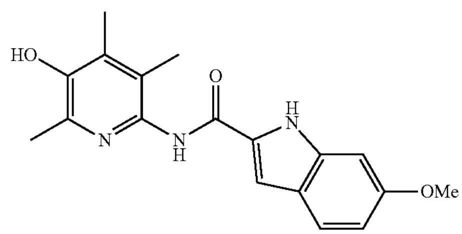 [SMILES: COc1ccc2cc(C(=O)Nc3nc(C)c(O)c(C)c3C)[nH]c2c1] | N-(5-hydroxy-3,4,6-trimethylpyridin-2-yl)-6-methoxy-1H-indole-2-carboxamide |
| X-13 | 39 | 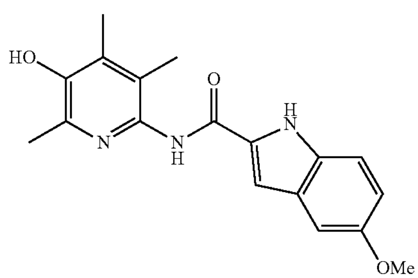 [SMILES: COc1ccc2[nH]c(C(=O)Nc3nc(C)c(O)c(C)c3C)cc2c1] | N-(5-hydroxy-3,4,6-trimethylpyridin-2-yl)-5-methoxy-1H-indole-2-carboxamide |
| X-14 | 40 | 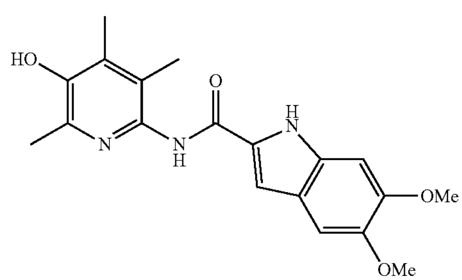 [SMILES: COc1cc2cc(C(=O)Nc3nc(C)c(O)c(C)c3C)[nH]c2cc1OC] | N-(5-hydroxy-3,4,6-trimethylpyridin-2-yl)-5,6-dimethoxy-1H-indole-2-carboxamide |
| X-15 | 41 | 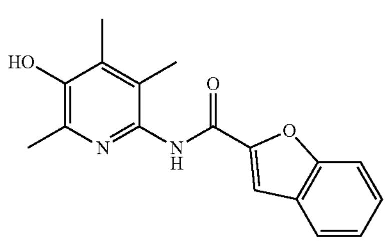 [SMILES: Cc1nc(NC(=O)c2cc3ccccc3o2)c(C)c(C)c1O] | N-(5-hydroxy-3,4,6-trimethylpyridin-2-yl)benzofuran-2-carboxamide |

TABLE 1-continued

| Number | Example | Structure | Name |
|---|---|---|---|
| X-16 | 42 | 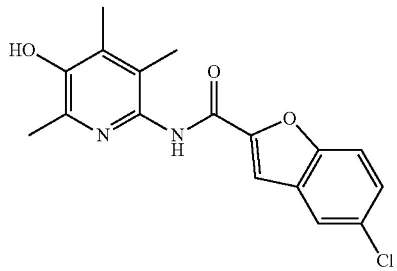 [SMILES: Cc1nc(NC(=O)c2cc3cc(Cl)ccc3o2)c(C)c(C)c1O] | 5-chloro-N-(5-hydroxy-3,4,6-trimethylpyridin-2-yl)benzofuran-2-carboxamide |
| X-17 | 43 | 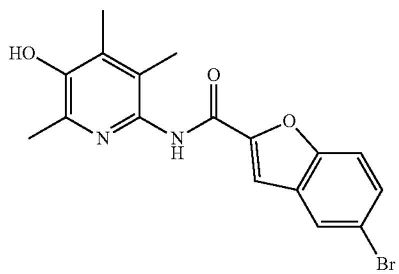 [SMILES: Cc1nc(NC(=O)c2cc3cc(Br)ccc3o2)c(C)c(C)c1O] | 5-bromo-N-(5-hydroxy-3,4,6-trimethylpyridin-2-yl)benzofuran-2-carboxamide |
| X-18 | 44 | 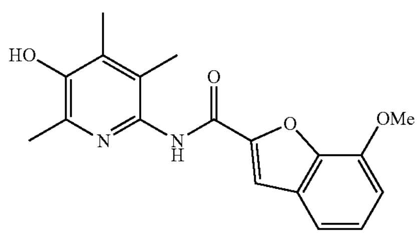 [SMILES: COc1cccc2cc(C(=O)Nc3nc(C)c(O)c(C)c3C)oc12] | N-(5-hydroxy-3,4,6-trimethylpyridin-2-yl)-7-methoxybenzofuran-2-carboxamide |
| X-19 | 45 | 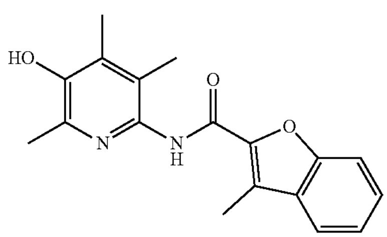 [SMILES: Cc1nc(NC(=O)c2oc3ccccc3c2C)c(C)c(C)c1O] | N-(5-hydroxy-3,4,6-trimethylpyridin-2-yl)-3-methylbenzofuran-2-carboxamide |
| X-20 | 46 | 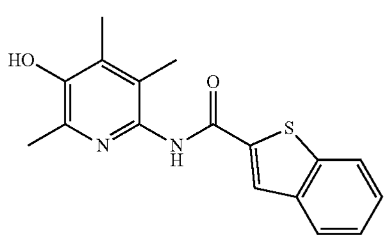 [SMILES: Cc1nc(NC(=O)c2cc3ccccc3s2)c(C)c(C)c1O] | N-(5-hydroxy-3,4,6-trimethylpyridin-2-yl)benzo[b]thiophene-2-carboxamide |
| X-21 | 47 | 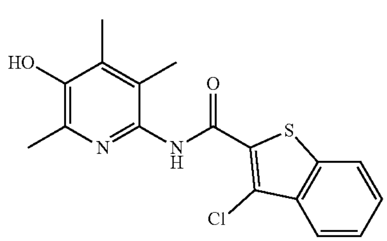 [SMILES: Cc1nc(NC(=O)c2sc3ccccc3c2Cl)c(C)c(C)c1O] | 3-chloro-N-(5-hydroxy-3,4,6-trimethylpyridin-2-yl)benzo[b]thiophene-2-carboxamide |

TABLE 1-continued

| Number | Example | Structure | Name |
|---|---|---|---|
| X-22 | 48 | 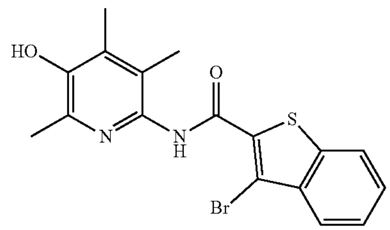 [SMILES: Cc1nc(NC(=O)c2sc3ccccc3c2Br)c(C)c(C)c1O] | 3-bromo-N-(5-hydroxy-3,4,6-trimethylpyridin-2-yl)benzo[b]thiophene-2-carboxamide |
| X-23 | 49 | 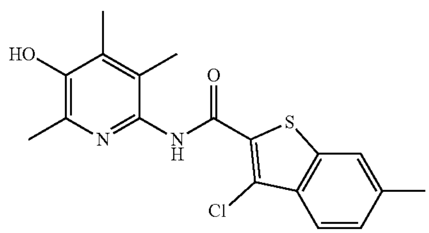 [SMILES: Cc1ccc2c(Cl)c(C(=O)Nc3nc(C)c(O)c(C)c3C)sc2c1] | 3-chloro-N-(5-hydroxy-3,4,6-trimethylpyridin-2-yl)-6-methylbenzo[b]thiophene-2-carboxamide |
| X-24 | 50 | 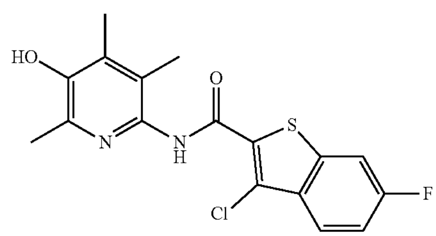 [SMILES: Cc1nc(NC(=O)c2sc3cc(F)ccc3c2Cl)c(C)c(C)c1O] | 3-chloro-6-fluoro-N-(5-hydroxy-3,4,6-trimethyl pyridin-2-yl)benzo[b]thiophene-2-carboxamide |
| X-25 | 51 | 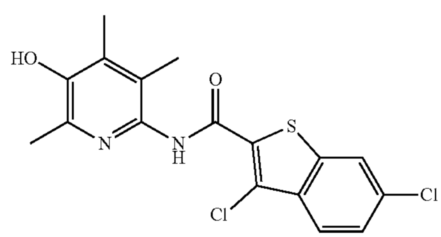 [SMILES: Cc1nc(NC(=O)c2sc3cc(Cl)ccc3c2Cl)c(C)c(C)c1O] | 3,6-dichloro-N-(5-hydroxy-3,4,6-trimethylpyridin-2-yl)benzo[b]thiophene-2-carboxamide |
| X-26 | 52 | 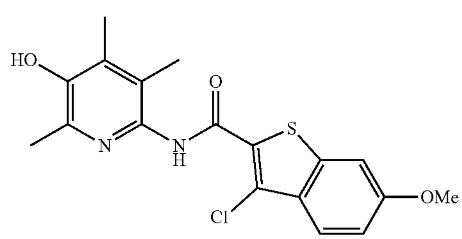 [SMILES: COc1ccc2c(Cl)c(C(=O)Nc3nc(C)c(O)c(C)c3C)sc2c1] | 3-chloro-N-(5-hydroxy-3,4,6-trimethylpyridin-2-yl)-6-methoxybenzo[b]thiophene-2-carboxamide |
| XI-01 | 53 | 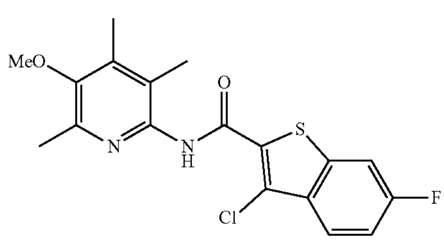 [SMILES: COc1c(C)nc(NC(=O)c2sc3cc(F)ccc3c2Cl)c(C)c1C] | 3-chloro-6-fluoro-N-(5-methoxy-3,4,6-trimethylpyridin-2-yl)benzo[b]thiophene-2-carboxamide |

TABLE 1-continued

| Number | Example | Structure | Name |
|---|---|---|---|
| XI-02 | 54 | 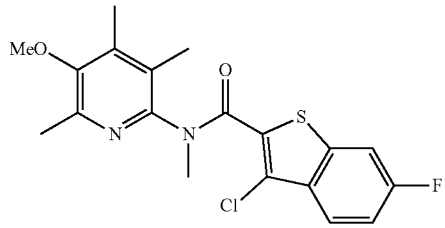 [SMILES: COc1c(C)nc(N(C)C(=O)c2sc3cc(F)ccc3c2Cl)c(C)c1C] | 3-chloro-6-fluoro-N-(5-methoxy-3,4,6-trimethylpyridin-2-yl)-N-methylbenzo[b]thiopheec-2-carboxamide |
| XI-03 | 55 | 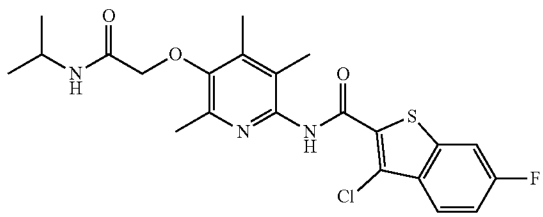 [SMILES: Cc1nc(NC(=O)c2sc3cc(F)ccc3c2Cl)c(C)c(C)c1OCC(=O)NC(C)C] | 3-chloro-6-fluoro-N-(5-(2-(isopropylamino)-2-oxoethoxy)-3,4,6-trimethylpyridin-2-yl)benzo[b]thiophene-2-carboxamide |
| XI-04 | 56 | 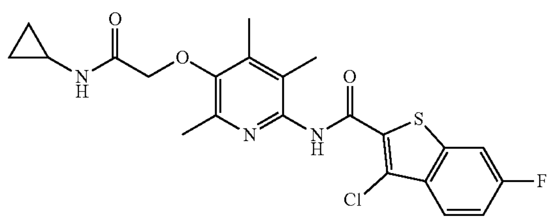 [SMILES: Cc1nc(NC(=O)c2sc3cc(F)ccc3c2Cl)c(C)c(C)c1OCC(=O)NC1CC1] | 3-chloro-N-(5-(2-(cyclopropylamino)-2-oxoethoxy)-3,4,6-trimethylpyridin-2-yl)-6-fluorobenzo[b]thiophene-2-carboxamide |
| XI-05 | 57 | 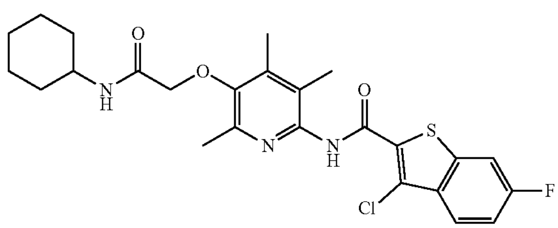 [SMILES: Cc1nc(NC(=O)c2sc3cc(F)ccc3c2Cl)c(C)c(C)c1OCC(=O)NC1CCCCC1] | 3-chloro-N-(5-(2-(cyclohexylamino)-2-oxoethoxy)-3,4,6-trimethylpyridin-2-yl)-6-fluorobenzo[b]thiophene-2-carboxamide |
| XI-06 | 58 | 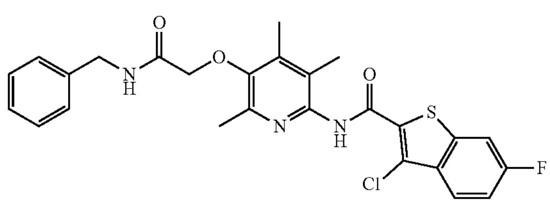 [SMILES: Cc1nc(NC(=O)c2sc3cc(F)ccc3c2Cl)c(C)c(C)c1OCC(=O)NCc1ccccc1] | N-(5-(2-(benzylamino)-2-oxoethoxy)-3,4,6-trimethyl yridin-2-yl)-3-chloro-6-fluorobenzo[b]thiophene-2-carboxamide |
| XI-07 | 59 | 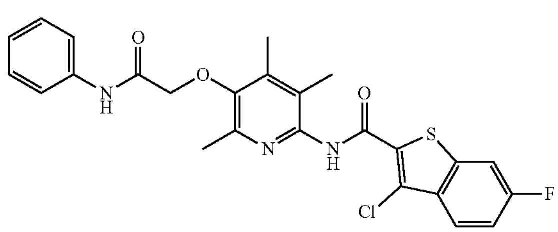 [SMILES: Cc1nc(NC(=O)c2sc3cc(F)ccc3c2Cl)c(C)c(C)c1OCC(=O)Nc1ccccc1] | 3-chloro-6-fluoro-N-(3,4,6-trimethyl-5-(2-oxo-2-(phenylamino)ethoxy)pyridin-2-yl)benzo[b]thiophene-2-carboxamide |
| XI-08 | 60 | 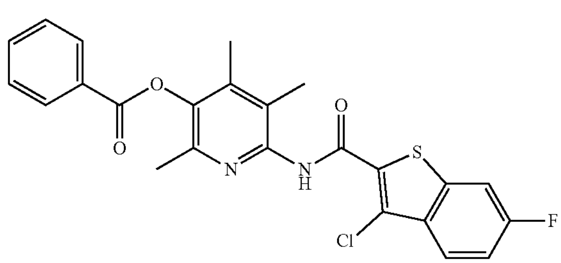 [SMILES: Cc1nc(NC(=O)c2sc3cc(F)ccc3c2Cl)c(C)c(C)c1OC(=O)c1ccccc1] | 6-(3-chloro-6-fluorobenzo[b]thiophene-2-carboxamido)-2,4,5-trimethylpyridin-3-yl benzoate |

TABLE 1-continued

| Number | Example | Structure | Name |
|---|---|---|---|
| XI-09 | 61 | 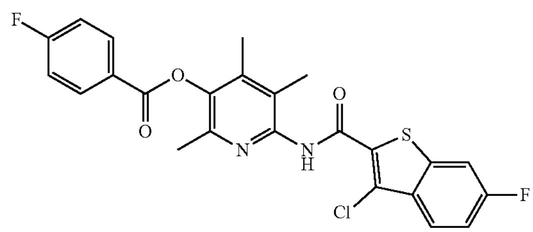 [SMILES: Cc1nc(NC(=O)c2sc3cc(F)ccc3c2Cl)c(C)c(C)c1OC(=O)c1ccc(F)cc1] | 6-(3-chloro-6-fluorobenzo[b]thiophene-2-carboxamido)-2,4,5-trimethylpyridin-3-yl 4-fluorobenzoate |
| XI-10 | 62 | 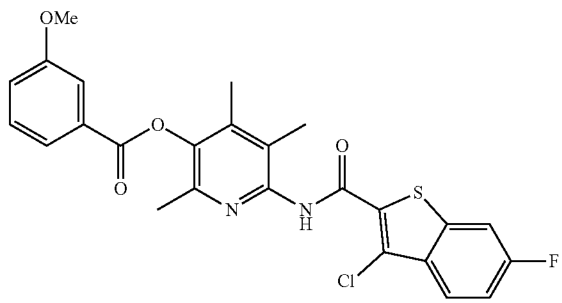 [SMILES: COc1cccc(C(=O)Oc2c(C)nc(NC(=O)c3sc4cc(F)ccc4c3Cl)c(C)c2C)c1] | 6-(3-chloro-6-fluorobenzo[b]thiophene-2-carboxamido)-2,4,5-trimethylpyridin-3-yl 3-methoxybenzoate |
| XI-11 | 63 | 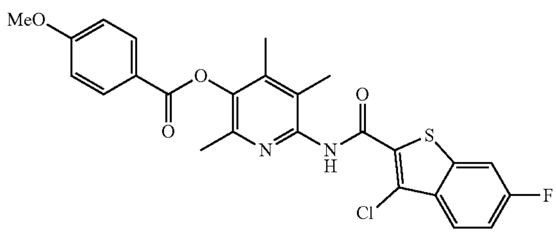 [SMILES: COc1ccc(C(=O)Oc2c(C)nc(NC(=O)c3sc4cc(F)ccc4c3Cl)c(C)c2C)cc1] | 6-(3-chloro-6-fluorobenzo[b]thiophene-2-carboxamido)-2,4,5-trimethylpyridin-3-yl 4-methoxybenzoate |
| XI-12 | 64 | 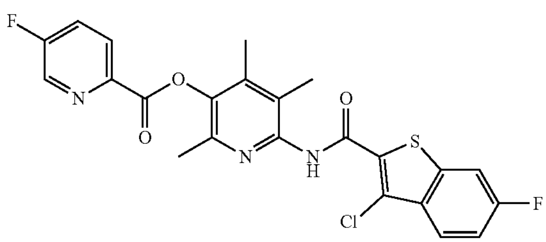 [SMILES: Cc1nc(NC(=O)c2sc3cc(F)ccc3c2Cl)c(C)c(C)c1OC(=O)c1ccc(F)cn1] | 6-(3-chloro-6-fluorobenzo[b]thiophene-2-carboxamido)-2,4,5-trimethylpyridin-3-yl 5-fluoropicolinate |
| XI-13 | 65 | 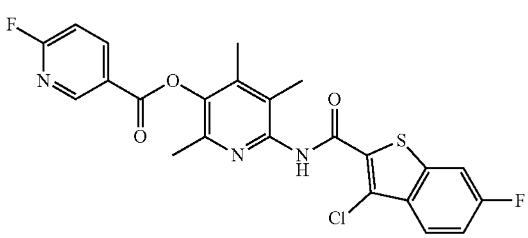 [SMILES: Cc1nc(NC(=O)c2sc3cc(F)ccc3c2Cl)c(C)c(C)c1OC(=O)c1ccc(F)nc1] | 6-(3-chloro-6-fluorobenzo[b]thiophene-2-carboxamido)-2,4,5-trimethylpyridin-3-yl 6-fluoronicotinate |
| XI-14 | 66 | 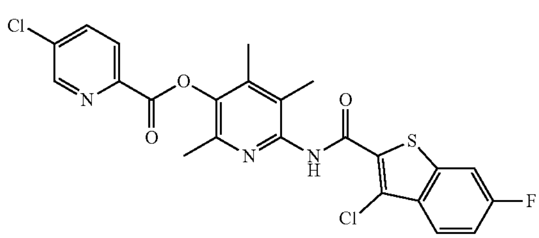 [SMILES: Cc1nc(NC(=O)c2sc3cc(F)ccc3c2Cl)c(C)c(C)c1OC(=O)c1ccc(Cl)cn1] | 6-(3-chloro-6-fluorobenzo[b]thiophene-2-carboxamido)-2,4,5-trimethylpyridin-3-yl 5-chloropicolinate |

TABLE 1-continued

| Number | Example | Structure | Name |
|---|---|---|---|
| XI-15 | 67 | 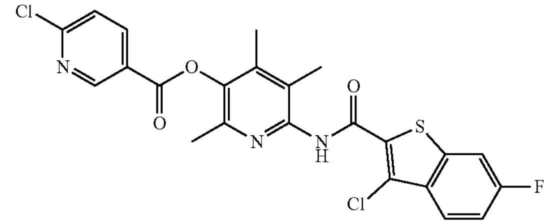 | 6-(3-chloro-6-fluorobenzo[b]thiophene-2-carboxamido)-2,4,5-trimethylpyridin-3-yl 6-chloropicolinate |
| XI-16 | 68 | 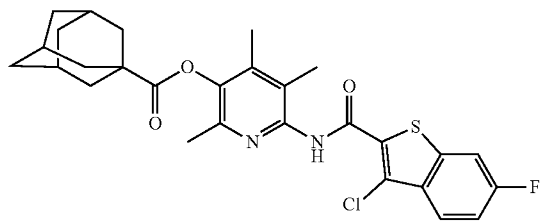 [SMILES: Cc1nc(NC(=O)c2sc3cc(F)ccc3c2Cl)c(C)c(C)c1OC(=O)C12CC3CC(CC(C3)C1)C2] | 6-(3-chloro-6-fluorobenzo[b]thiophene-2-carboxamido)-2,4,5-trimethylpyridin-3-yl (3r,5r,7r)-adamantane-1-carboxylate |
| XI-17 | 69 | 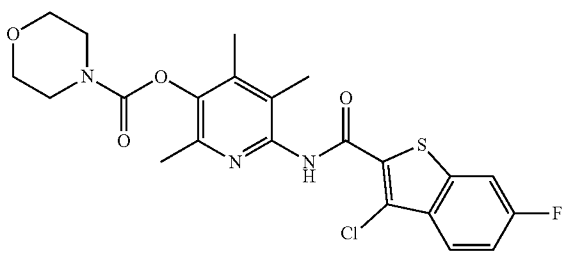 [SMILES: Cc1nc(NC(=O)c2sc3cc(F)ccc3c2Cl)c(C)c(C)c1OC(=O)N1CCOCC1] | 6-(3-chloro-6-fluorobenzo[b]thiophene-2-carboxamido)-2,4,5-trimethylpyridin-3-yl morpholine-4-carboxylate |

<Experimental Example 1> Activity Test for Inhibiting Adhesion of Monocytes and Intestinal Epithelial Cells Induced by TNF-α

<Test Method>

HT-29 human colon cancer-derived epithelial cells and U937 human-derived monocytes were cultured in RPMI 1640 medium containing 10% FBS and 1% penicillin/streptomycin (PS) in a 37° C., 5% $CO_2$ incubator. When the cells grew more than 80% of the bottom area of the culture flask, they were passaged at a ratio of 1:3 and used in this experiment. HT-29 cells were cultured in a 24-well plate at the density of $2\times10^5$ cells/cm$^2$, and the test drug was pretreated in a medium containing 1% FBS and 1% PS for 1 hour. Thereafter, 10 μg/mL of BCECF-AM was treated thereto and reacted at 37° C. for 30 minutes. U937 cells loaded with BCECF and TNF-α (10 ng/mL) were reacted with HT-29 cells previously treated with the test drug at 37° C. for 3 hours. Upon completion of the reaction, the medium was removed, and the culture flask was washed twice with PBS to remove non-adherent U937 cells. In the next step, the cells were lysed by treating with 0.1% Triton X-100 (0.1 M Tris) and reacted at room temperature for 30 minutes. Then, fluorescence was measured and quantified using a fluostar optima microplate reader (BMG Labtechnologies, Germany) (Carvalho et al., 1996; Thapa et al., 2008).

Carvalho, D., Savage, C. O., Black, C. M. and Pearson, J. D., IgG antiendothelial cell autoantibodies from scleroderma patients induce leukocyte adhesion to human vascular endothelial cells in vitro. Induction of adhesion molecule expression and involvement of endothelium-derived cytokines. J. Clin. Invest. 97, 111-119 (1996).

Thapa, D., Lee, J. S., Park, S. Y., Bae, Y. H., Bae, S. K., Kwon, J. B., Kim, K. J., Kwak, M. K., Park, Y. J., Choi, H. G. and Kim, J. A., Clotrimazole Ameliorates Intestinal Inflammation and Abnormal Angiogenesis by Inhibiting Interleukin-8 Expression through a Nuclear Factor-kB-Dependent Manner. J. Pharmacol. Exp. Ther. 327, 353-364 (2008).

TABLE 2

| Compound | Inhibitory activity (%) |
|---|---|
| 5-ASA | 3.8 |
| X-01 | 43.2 |
| X-02 | 29.1 |
| X-03 | 14.5 |
| X-04 | 30.3 |
| X-05 | 7.5 |
| X-06 | 49.9 |
| X-07 | 88.9 |
| X-08 | 31.0 |
| X-09 | 82.8 |
| X-10 | 57.2 |
| X-11 | 32.8 |
| X-12 | 50.9 |
| X-13 | 36.7 |
| X-14 | 36.9 |
| X-15 | 4.8 |
| X-16 | 25.1 |
| X-17 | 8.5 |
| X-18 | 55.1 |
| X-19 | 25.1 |
| X-20 | 16.5 |
| X-21 | 13.4 |
| X-22 | 26.8 |
| X-23 | 9.1 |
| X-24 | 90.3 |
| X-25 | 19.5 |
| X-26 | 45.1 |
| XI-01 | 9.3 |

TABLE 2-continued

| Compound | Inhibitory activity (%) |
|---|---|
| XI-02 | 18.5 |
| XI-03 | 60.6 |
| XI-04 | 13.9 |
| XI-05 | 25.5 |
| XI-06 | 62.1 |
| XI-07 | 84.1 |
| XI-08 | 7.7 |
| XI-09 | 3.4 |
| XI-10 | 46.5 |
| XI-11 | 77.2 |
| XI-12 | 31.9 |
| XI-13 | 20.7 |
| XI-14 | 38.1 |
| XI-15 | 20.3 |
| XI-16 | 29.2 |
| XI-17 | 65.7 |

As shown in table 2 illustrating the results of investigating the inhibitory activity of the test drug (1 μM) on the adhesion of intestinal epithelial cells (HT-29) and monocytic cells (U937) induced by TNF-α, the inhibitory rate of 5-ASA (positive control), an active metabolite of sulfasalazine which is a drug currently used in clinical trials for the treatment of inflammatory bowel disease, was 3.8%, showing little effect, whereas compound X-24 of the present invention exhibited the inhibitory rate of 90.3%, showing very excellent activity.

In addition, compound X-07 showed the inhibitory rate of 88.9%, compound XI-07 showed the inhibitory rate of 84.1%, compound X-09 showed the inhibitory rate of 82.8%, and compound XI-11 showed the inhibitory rate of 77.2%.

The compounds showing the inhibitory rate of 50% or more are listed in the order of excellent inhibitory activity as follows: compound XI-17> compound XI-06> compound XI-03> compound X-10> compound X-18> compound X-12. Except for compound XI-09, all other compounds were confirmed to have better inhibitory activity than that of 5-ASA.

From the above results, it was confirmed that the compound represented by formula 1 of the present invention can be effectively used for the treatment of inflammatory bowel disease, and it can be seen that the compound of the present invention can be used as a substitute for existing drugs.

<Experimental Example 2> Activity Test for Inhibiting Adhesion of Monocytes and Intestinal Epithelial Cells Induced by IL-6

<Test Method>

The inhibitory activity test for intestinal epithelial cell-monocyte adhesion by IL-6 was performed using the same method as in the case of TNF-α. HT-29 cells were cultured in a 24-well plate at the density of $2 \times 10^5$ cells/cm$^2$, and the test drug was pretreated in a medium containing 1% FBS and 1% PS for 1 hour. Thereafter, 10 μg/mL of BCECF-AM was treated thereto and reacted at 37° C. for 30 minutes. U937 cells loaded with BCECF and IL-6 (10 ng/mL) were reacted with HT-29 cells previously treated with the test drug at 37° C. for 3 hours. Upon completion of the reaction, the medium was removed, and the culture flask was washed twice with PBS to remove non-adherent U937 cells. In the next step, the cells were lysed by treating with 0.1% Triton X-100 (0.1 M Tris) and reacted at room temperature for 30 minutes. Then, fluorescence was measured and quantified using a fluostar optima microplate reader (BMG Labtechnologies, Germany).

TABLE 3

| Compound | inhibitory activity (%) |
|---|---|
| 5-ASA | <1.7 |
| Tofacitinib | 49.1 |
| X-01 | 34.0 |
| X-02 | 21.1 |
| X-03 | 5.0 |
| X-04 | 25.1 |
| X-05 | 3.4 |
| X-06 | 42.9 |
| X-07 | 80.3 |
| X-08 | 21.3 |
| X-09 | 71.7 |
| X-10 | 47.9 |
| X-11 | 24.2 |
| X-12 | 46.0 |
| X-13 | 23.4 |
| X-14 | 29.5 |
| X-15 | 42.4 |
| X-16 | 15.1 |
| X-17 | 3.6 |
| X-18 | 48.8 |
| X-19 | 18.7 |
| X-20 | 27.0 |
| X-21 | 11.4 |
| X-22 | 19.7 |
| X-23 | 8.7 |
| X-24 | 79.2 |
| X-25 | 9.0 |
| X-26 | 38.4 |
| XI-01 | 4.7 |
| XI-02 | 10.9 |
| XI-03 | 49.9 |
| XI-04 | 6.5 |
| XI-05 | 14.5 |
| XI-06 | 54.1 |
| XI-07 | 72.8 |
| XI-08 | 6.8 |
| XI-09 | 21.2 |
| XI-10 | 13.1 |
| XI-11 | 67.0 |
| XI-12 | 18.0 |
| XI-13 | 15.2 |
| XI-14 | 26.8 |
| XI-15 | 13.6 |
| XI-16 | 20.3 |
| XI-17 | 59.6 |

As shown in table 3 illustrating the results of investigating the inhibitory activity of the test drug (1 μM) on the adhesion of intestinal epithelial cells (HT-29) and monocytic cells (U937) induced by IL-6, the inhibitory rate of the existing drug 5-ASA was less than 1.7% at the concentration of 1 μM, showing little effect, whereas tofacitinib showed the inhibitory rate of 49.1%.

The inhibitory rate of compound X-07 of the present invention was 80.3%, showing very good activity. In addition, compound X-24 showed the inhibitory rate of 79.2%, compound XI-07 showed the inhibitory rate of 72.8%, compound X-09 showed the inhibitory rate of 71.7%, compound XI-11 showed the inhibitory rate of 67%, compound XI-17 showed the inhibitory rate of 59.6%, and compound XI-06 showed the inhibitory rate of 54.1%. All other compounds were confirmed to have better inhibitory activity than that of 5-ASA.

The results ($IC_{50}$) of investigating the inhibitory activity of the two compounds having excellent activity on the adhesion of intestinal epithelial cells and monocytic cells induced by TNF-α and IL-6 are shown in table 4 below.

TABLE 4

| Compound | TNF-α (IC$_{50}$) | IL-6 (IC$_{50}$) |
| --- | --- | --- |
| 5-ASA | 18.1 mM | 25.1 mM |
| Tofacitinib | 0.70 μM | 0.44 μM |
| X-09 | 0.30 μM | 0.34 μM |
| X-24 | 0.23 μM | 0.35 μM |

As shown in table 4, in the case of 5-ASA used as a control drug, the IC$_{50}$ for inhibition of adhesion by TNF-α was 18.1 mM, and the IC$_{50}$ for inhibition of adhesion by IL-6 was 25.1 mM. On the other hand, in the case of compound X-09 of the present invention, the IC$_{50}$ for inhibition of adhesion by TNF-α and IL-6 were 0.30 μM and 0.34 μM, respectively. In the case of compound X-24, the IC$_{50}$ for inhibition of adhesion by TNF-α and IL-6 were 0.23 μM and 0.35 μM, respectively. Compounds X-09 and X-24 respectively showed excellent activity that was tens of thousands of times greater than that of 5-ASA, and also showed superior activity compared to that of tofacitinib.

From the above results, it was confirmed that the compound represented by formula 1 of the present invention can be effectively used for the treatment of inflammatory bowel disease, and it can be seen that the compound of the present invention can be used as a substitute for existing drugs.

<Experimental Example 3> In Vivo Efficacy Test According to Oral Administration of Compounds in TNBS-Induced Inflammatory Bowel Disease Rat Model <Test Method>

Sprague Dawley rats aged 7-8 weeks were purchased from OrientBio (Korea), stabilized with general solid feed for 3 days, and then used in this experiment. Feed and water were freely supplied during the experiment period, and the temperature of the breeding room was maintained at 25±1° C. and the relative humidity at 50±10%. Lighting management was controlled in a 12-hour light-dark cycle by an automatic lighting controller. Experimental groups were divided into 5 groups (control group, TNBS alone treated group, TNBS+sulfasalazine (300 mg/kg) treated group, TNBS+tofacitinib (30 mg/kg) treated group, TNBS+test drug (1 mg/kg) treated group) in which 6 animals in each group and the average body weight were 180±10 g according to a randomized block design.

(1) Inducing Enteritis by Rectal Administration of TNBS

After anesthetizing rats that had been fasted for 24 hours with diethyl ether, 0.8 mL of 5% TNBS diluted with 50v/v % ethanol was slowly injected into the lumen of the colon using a 1 mL syringe connected to a polyethylene catheter, and then, the rats were left standing for 60 seconds in an inverted position in order to prevent 5% TNBS from leaking into the anus. For the control group, only vehicle [50v/v % ethanol] was injected in the same manner as in the other groups (Thapa et al., 2008).

(2) Drug Administration

In order to investigate the effect of the drug, the drug was administered at a constant time every day for 5 days from the day after the TNBS treatment.

(3) Weight Observation

Changes in body weight of each rat were observed from the fasting stage to the TNBS administration and drug administration process using a digital mass meter.

(4) Measurement of Colon Weight

The colon of the rat was extracted, and the tissue 5-6 cm away from the anus was cut into a length of 1 cm, and the weight of the tissue was measured.

(5) Staining of Colon Tissue and Measurement of Mucosal Damage

The weighed rat tissues were fixed with 4% paraformaldehyde solution, and then transferred to 30% sucrose solution. When the tissues subside, they were taken out and cut into 25 m thick using a cryomicrotome (Microm HM 450, Thermo Fisher Scientific, Germany) and stored in a cryopreservation solution. After washing the tissue section with KPBS, the tissue section was attached to a slide glass, dried, and then stained with hematoxylin & Eosin and observed under a microscope. The degree of mucosal damage and recovery was scored as shown in table 5 below, and a total score of 6 points per rat was confirmed.

TABLE 5

| Colon mucosal damage | Score |
| --- | --- |
| 1) Inflammatory cell infiltration | |
| Occasional inflammatory cells in the lamina propria | 0 |
| Increased numbers of inflammatory cells in the lamina propria | 1 |
| Confluence of inflammatory cells, extending into the submucosa | 2 |
| Transmural extension of the infiltrate | 3 |
| 2) Tissue damage | |
| No mucosal damage | 0 |
| Discrete lymphoepithelial lesions | 1 |
| Surface mucosal erosion or focal ulceration | 2 |
| Extensive mucosal damage and extension into deeper structures of the bowel wall | 3 |

<Analysis of Effect of Oral Administration of Compounds on TNBS-Induced Enteritis>

The in vivo enteritis inhibitory activity at a fixed dose (1 mg/kg) of the compounds showing excellent activity in the in vitro adhesion inhibition test was measured as the intestinal weight recovery rate and body weight recovery rate, and the results are shown in table 6. In addition, the dose-dependent activity of compound X-09 is shown in table 7.

TABLE 6

| Compound | Dose | Intestinal weight recovery rate (%) | Body weight recovery rate (%) |
| --- | --- | --- | --- |
| Sulfasalazine | 300 mg/kg | 69.6 | 86.6 |
| X-24 | 1 mg/kg | 97.4 | 86.6 |
| X-07 | 1 mg/kg | 94.9 | 72.9 |
| X-09 | 1 mg/kg | 94.0 | 72.7 |
| XI-07 | 1 mg/kg | 91.0 | 82.9 |
| XI-17 | 1 mg/kg | 79.8 | 60.2 |

TABLE 7

| Compound | Dose | Intestinal weight recovery rate (%) | Body weight recovery rate (%) |
| --- | --- | --- | --- |
| Sulfasalazine | 300 mg/kg | 69.6 | 86.6 |
| Triamcinolone | 10 mg/kg | 84.5 | 70.0 |
| X-09 | 0.3 mg/kg | 47.0 | 17.2 |
| X-09 | 1 mg/kg | 85.2 | 69.3 |
| X-09 | 3 mg/kg | 91.7 | 74.6 |
| X-09 | 10 mg/kg | 98.9 | 80.8 |

1. Weight Change

In a colitis model in which intestinal inflammation was induced by treatment with 5% TNBS in rats weighing 180-190 g, the change in body weight was observed at a certain time every day for 5 days based on the body weight before TNBS treatment. As a result, the body weight of the vehicle-treated control group rats continued to increase, and the weight of the TNBS-treated group rats continued to decrease, and the body weight recovered slightly from the $5^{th}$ day, but the body weight was significantly reduced compared to the normal group rats. The body weight of the rats treated with 300 mg/kg of sulfasalazine, a positive control group, was gradually recovered, and although the body weight was decreased compared to that of the vehicle-treated control group rats, it was significantly increased compared to the body weight of the rats treated with TNBS alone, resulting in a weight recovery rate of 50.5%. The pyridinol compounds showed a recovery rate of 60.2%~86.6% when 1 mg/kg was administered. The compounds are listed in the order of excellent weight recovery rate as follows: compounds X-24, XI-07, X-07, X-09, and XI-17. For compound X-09, the dose-dependent activity was measured by adding 10 mg/kg of triamcinolone in addition to 300 mg/kg of sulfasalazine, a positive control. As a result, it was confirmed that the compound X-09 exhibited a dose-dependent body weight recovery activity and was more effective than triamcinolone at the same concentration.

2. Morphological Observation

After 5 days of drug administration, the colon was extracted and visually inspected. As a result, the colon of the rats treated with TNBS showed edema and hyperemia compared to the control group rats, and edema and congestion of the appendix and adhesions of the intestinal tissues were observed. In the group treated with 300 mg/kg of sulfasalazine, a positive control group, the symptoms observed with the naked eye and adhesions between other organs and colonic congestion were also significantly suppressed. In the group treated with the pyridinol compound, the symptoms improved more than the group treated with 300 mg/kg of sulfasalazine. It was also confirmed that the compound X-09 exhibited a dose-dependent therapeutic activity for enteritis and was more effective than triamcinolone at the same concentration.

3. Measurement of Colon Weight

The degree of inflammation of the rat colon is a key scale (important index) of IBD progression that is more important than body weight change. The colon was extracted and the weight of the tissue 5-6 cm away from the anus was measured. As a result, the weight of the colon with edema was significantly increased in the rats of the group treated with TNBS alone, compared to the vehicle-treated control group rats. In the rats of the group treated with 300 mg/kg of sulfasalazine, a positive control, the weight recovery rate of the colon tissue was 69.6%. The pyridinol compounds showed a recovery rate of 79.8%~97.4% when 1 mg/kg was administered. The compounds are listed in the order of excellent weight recovery rate as follows: compounds X-24, XI-07, X-07, X-09, and XI-17. It was also confirmed that the compound X-09 exhibited a dose-dependent body weight recovery activity and was more effective than triamcinolone at the same concentration.

4. Measurement of Mucosal Damage Recovery of Rat Colon

Figure 1B:
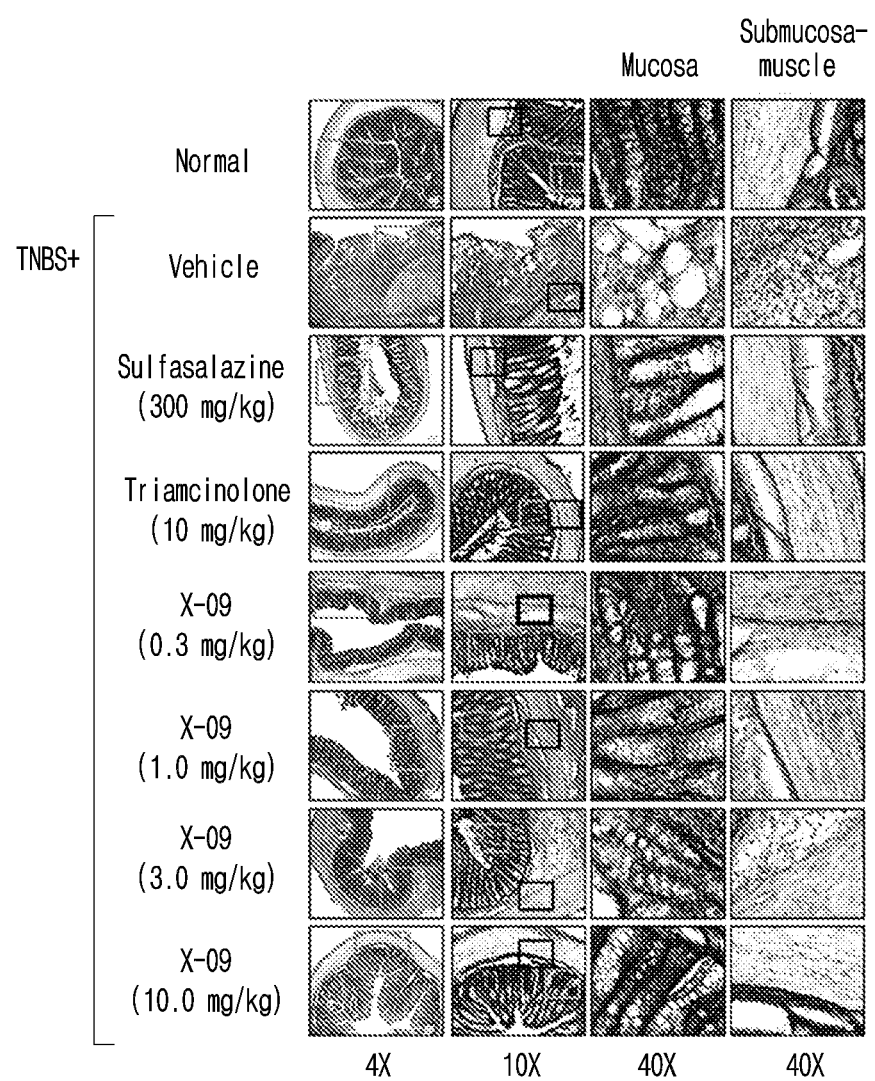

After observing the morphology of the colon in the dose-dependent activity measurement experiment, hematoxylin-eosin staining of the colon tissue was performed to score and compare the degree of colon mucosal damage. As a result, it was confirmed that the compound X-09 exhibited a dose-dependent mucosal damage recovery activity and was more effective than triamcinolone at the same concentration (FIG. 1).

From the results of Experimental Example 3, it was confirmed that the compound represented by formula 1 of the present invention can be effectively used for the treatment of inflammatory bowel disease, and it can be seen that the compound of the present invention can be used as a substitute for existing drugs.

<Experimental Example 4> In Vivo Efficacy Test According to Oral Administration of Compounds in Dextran Sulfate Sodium (DSS)-Induced Inflammatory Bowel Disease Mouse Model <Test Method>

C57BL/6 mice aged 7-8 weeks were purchased from OrientBio (Korea), stabilized with general solid feed for 7 days, and then used in this experiment. Feed and water were freely supplied during the experiment period, and the temperature of the breeding room was maintained at 25±1° C. and the relative humidity at 50±10%. Lighting management was controlled in a 12-hour light-dark cycle by an automatic lighting controller.

Figure 2A:
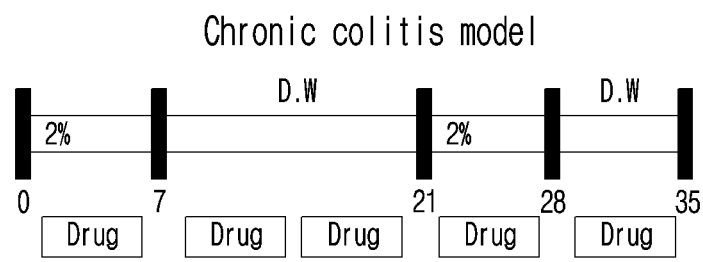
FIG. 2A is a schematic diagram showing the drug administration time for measuring the pharmacological effect of the compound of the present invention in the DSS-induced chronic enteritis animal model of Experimental Example 4.
Figure 3A:
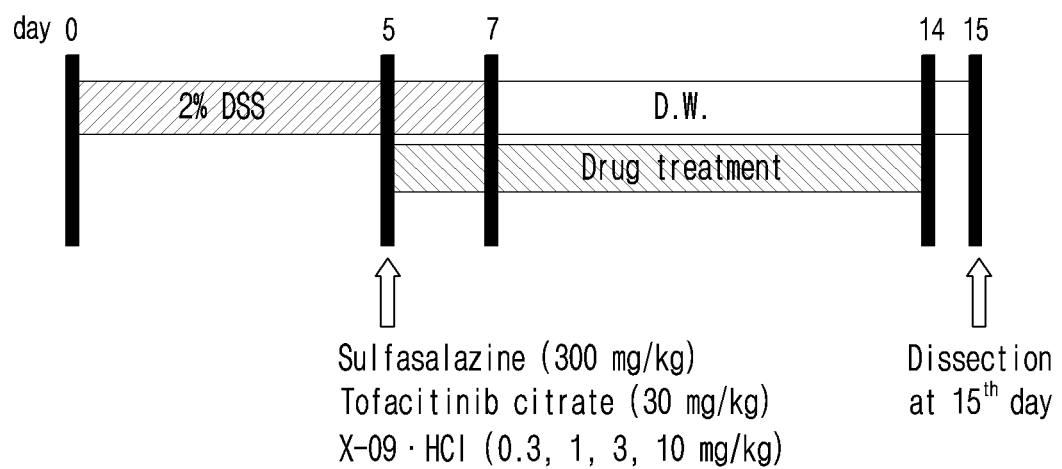
FIG. 3A is a schematic diagram showing the drug administration time for measuring the pharmacological effect of the compound of the present invention in the DSS-induced acute enteritis animal model of Experimental Example 4.

(1) Inducing Acute-Chronic Enteritis by DSS and Measuring Preventive and Therapeutic Effects of Drugs Enteritis was induced in mice by allowing them to freely ingest drinking water containing 2% DSS salt (M.W. 36,000~50,000, MP Biomedicals, LLC, OH, USA). For the chronic enteritis model, DSS was administered using a schedule of DSS administration for the first 7 days, administration of normal drinking water for 14 days, repeated administration of DSS for 7 days from the $21^{st}$ day, and administration of normal drinking water for 7 days. The drug was administered once a day, 6 days a week from the first day of DSS treatment (FIG. 2A). Experimental groups were divided into 6 groups (control group, DSS alone treated group, DSS+sulfasalazine (300 mg/kg) treated group, DSS+tofacitinib (30 mg/kg) treated group, DSS+test drug (1 mg/kg) treated group, and DSS+test drug (3 mg/kg) treated group) in which 6 animals in each group and the average body weight were 20±1 g according to a randomized block design. In order to measure the dose-dependent therapeutic effect of the drug in the acute enteritis model, DSS was administered for 5 days to induce enteritis, and then the drug was administered for 14 days to measure the degree of recovery and treatment of enteritis (FIG. 3A). The drug was administered orally once daily for 10 days at a fixed time.

(2) Weight Observation

Changes in body weight of each mouse were observed during the DSS and drug administration using a digital mass meter.

(3) Measurement of Colon Length and Weight

The colon of the mouse was extracted, and the length and weight from the anus to the cecum were measured.

(4) Measurement of MPO

The degree of neutrophil infiltration in the tissue was measured by the amount of MPO, a neutrophil marker enzyme. The colon tissue with a size of 1 cm was washed with cold PBS and weighed, to which a lysis buffer (pH7.4, 200 mM NaCl, 5 mM EDTA, 10 mM tris, 10% glycerin, 1 mM PMSF, 1 µg/mL leupeptin and 28 µg/mL aprotinin) was added (500 µL of per 10 mg of tissue weight), and then homogenized using Bead Blaster® D2400 homogenizer (Benchmark Scientific, NJ, USA). The homogenized sample was centrifuged twice at 1500×g for 5 minutes to obtain a supernatant, and then 100 µL of this supernatant was measured using a kit. The homogenized sample was centrifuged twice at 1500×g for 5 minutes to obtain a supernatant, and then 100 µL of this supernatant was measured using MPO ELISA kit (HK210, Hycult Biotechnology, Netherlands). The supernatant was added to a 96 well plate (100 µL/well) coated with an anti-mouse MPO antibody, and incubated for 1 hour at room temperature, followed by washing 3 times with a washing buffer. A reconstituted tracer was added to the plate (100 µL/well), which was reacted at room temperature for 1 hour, washed 3 times, and then 100 µL of streptavidin-peroxidase conjugate was added to each well of the plate. The plate was reacted at room temperature for 1 hour, washed, and 100 µl of TMB substrate solution was added to each well of the plate, followed by reaction for 30 minutes. The reaction was terminated by adding 100 µL of a stop solution to each well of the plate, and absorbance was measured at 450 nm. MPO activity means the amount of 1 µM hydrogen peroxide reduced from water at 25° C. for 1 minute. This was calculated as the amount of MPO contained in 1 mL of the colon tissue homogenate.

(5) Tissue Staining

Tissue staining was performed in the same manner as in the case of hematoxylin/eosin staining of the rat colon tissue, and scoring indexes of mucosal damage and recovery were applied in the same way.

<Analysis of Effect of Oral Administration of Compounds on DSS-Induced Acute and Chronic Mouse Enteritis>

The inhibitory activity of compound X-24 against DSS-induced chronic mouse enteritis was measured, and the results are shown in table 8. The dose-dependent therapeutic efficacy of compound X-09 on DSS-induced acute mouse enteritis was measured, and the results are shown in table 9.

TABLE 8

| Compound | Dose | Chronic enteritis (DSS-water-DSS administration/total 35 days) | |
|---|---|---|---|
| | | Intestinal weight recovery rate (%) | Body weight recovery rate (%) |
| Sulfasalazine | 300 mg/kg | 66.9 | 22.8 |
| Tofacitinib | 30 mg/kg | 68.2 | 29.5 |
| X-24 | 1 mg/kg | 58.1 | 22.8 |
| X-24 | 3 mg/kg | 98.2 | 73.3 |

TABLE 9

| Compound | Dose | Acute enteritis | |
|---|---|---|---|
| | | Intestinal weight recovery rate (%) | Body weight recovery rate (%) |
| Sulfasalazine | 300 mg/kg | 66.2 | 65.9 |
| Tofacitinib | 30 mg/kg | 80.9 | 80.8 |
| X-09 | 0.3 mg/kg | 48.4 | 56.5 |
| X-09 | 1 mg/kg | 76.7 | 72.0 |
| X-09 | 3 mg/kg | 89.0 | 80.7 |
| X-09 | 10 mg/kg | 96.4 | 88.1 |

1. Weight Change

Figure 2B:
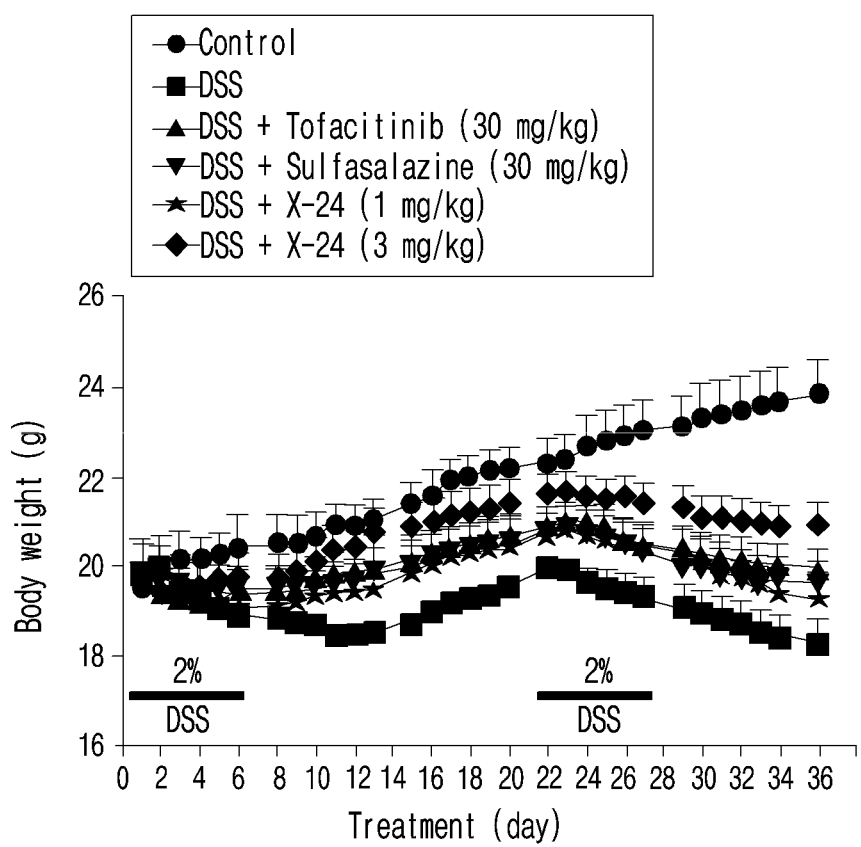
FIG. 2B is a graph showing the changes in the body weight according to the treatment of the compound of the present invention in the DSS-induced chronic enteritis animal model of Experimental Example 4.

In a chronic enteritis model in which chronic inflammation was induced by supplying water containing 2% DSS for 7 days, water for 14 days, and then water containing 2% DSS for 7 days in mice weighing 19-21 g, the efficacy of the pyridinol compound was measured. The changes in body weight were observed in the chronic enteritis model. As a result, the weight of the vehicle-treated control group mouse continued to increase, and the weight of the DSS-treated group mouse was decreased due to the DSS treatment and began to recover the weight while drinking water, but the weight significantly decreased again due to the second DSS administration. The weight recovery rate of the mouse of the group treated with 300 mg/kg of sulfasalazine or 30 mg/kg of tofacitinib, a positive control group, after 35 days was 22.8% and 29.4%, respectively, compared to the vehicle-treated control group mouse. On the other hand, the mouse of the group treated with the pyridinol compound X-24 showed a dose-dependent body weight recovery rate (22.8%, 73.3%) (FIG. 2B).

Figure 3B:
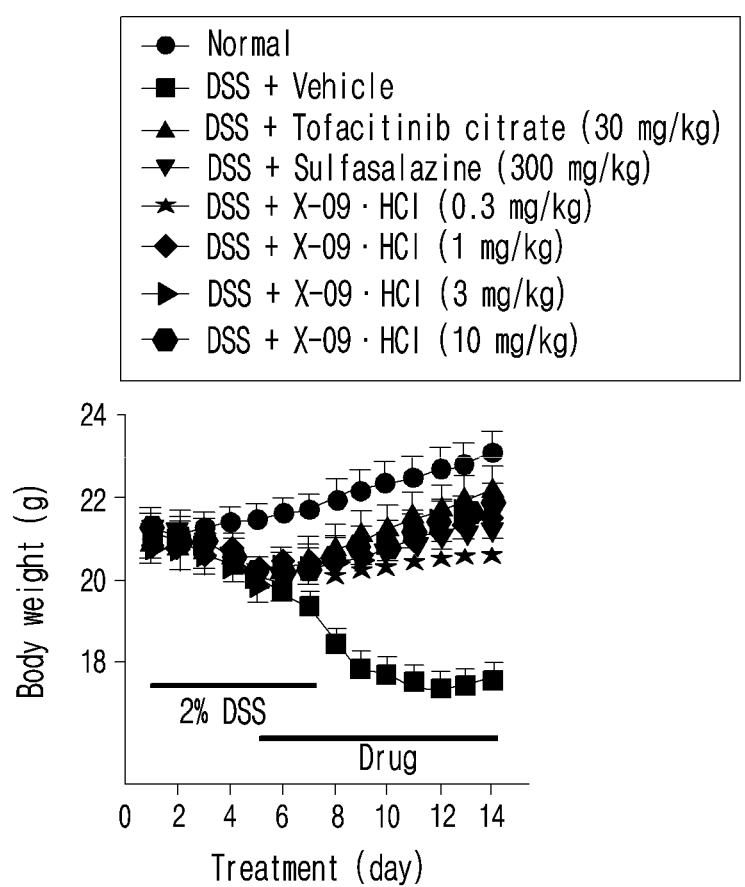
FIG. 3B is a graph showing the changes in the body weight according to the treatment of the compound of the present invention in the DSS-induced acute enteritis animal model of Experimental Example 4.

In an acute enteritis model in which intestinal inflammation was induced by supplying water containing 2% DSS for 7 days in mice weighing 19-21 g, the change in body weight was observed at a certain time every day based on the body weight before DSS treatment. As a result, the body weight of the vehicle-treated control group mice continued to increase, and the weight of the DSS-treated group mice continued to decrease, and thus the body weight was significantly reduced compared to the normal group mice. The body weight of the mice treated with 300 mg/kg of sulfasalazine or 30 mg/kg of tofacitinib, a positive control group, was gradually recovered, and although the body weight was decreased compared to that of the vehicle-treated control group rats, it was significantly increased compared to the body weight of the mice treated with DSS alone, resulting in a weight recovery rate of 65.9% and 80.9%, respectively. The dose-dependent efficacy of the compound X-09 on DSS-induced acute intestinal inflammation according to the oral administration was measured. As a result, the mice of the group treated with the pyridinol compound X-09 showed weight recovery rates of 56.5, 72.0, 80.7, and 88.1% at the compound concentrations of 0.3, 1, 3, and 10 mg/kg, respectively (FIG. 3B).

2. Morphological Observation

Figure 2C:
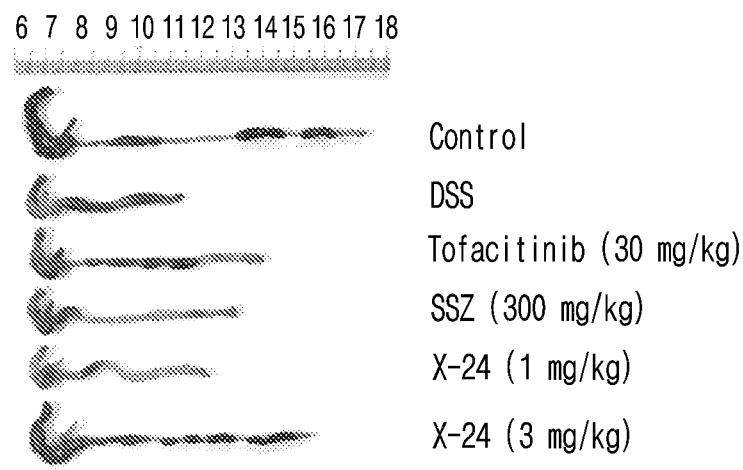
FIG. 2C is a diagram showing the morphological changes of the colon according to the treatment of the compound of the present invention in the DSS-induced chronic enteritis animal model of Experimental Example 4.
Figure 3C:
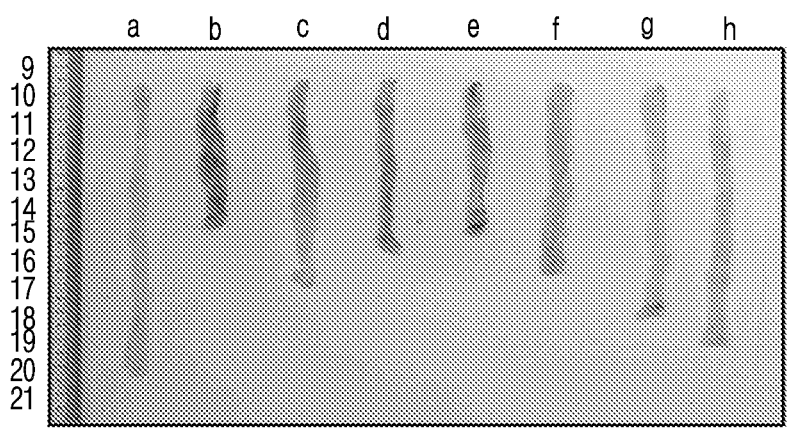
FIG. 3C is a diagram showing the morphological changes of the colon according to the treatment of the compound of the present invention in the DSS-induced acute enteritis animal model of Experimental Example 4.

After 7 days of drug administration, the colon was extracted and visually inspected. As a result, the colon of the mice treated with DSS was significantly shorter compared to the control group, and edema and hyperemia were observed. In addition, edema and congestion of the appendix and adhesions of intestinal tissues were observed. In the group treated with 300 mg/kg of sulfasalazine or 30 mg/kg of tofacitinib, a positive control group, the recovery of intestinal length was observed, and the macroscopic symptoms and adhesions between other organs and colonic congestion were also significantly suppressed. In the group treated with the pyridinol compound, it was observed that the symptoms were more ameliorated than the group treated with 30 mg/kg of tofacitinib as well as the group treated with 300 mg/kg of sulfasalazine (FIG. 2C). The compound X-09 showed a dose-dependent therapeutic efficacy, and the therapeutic effect in the group treated with 10 mg/kg of the compound X-09 was significantly superior to that of the control group treated with 30 mg/kg of tofacitinib (FIG. 3C).

3. Measurement of Colon Weight

Figure 2D:
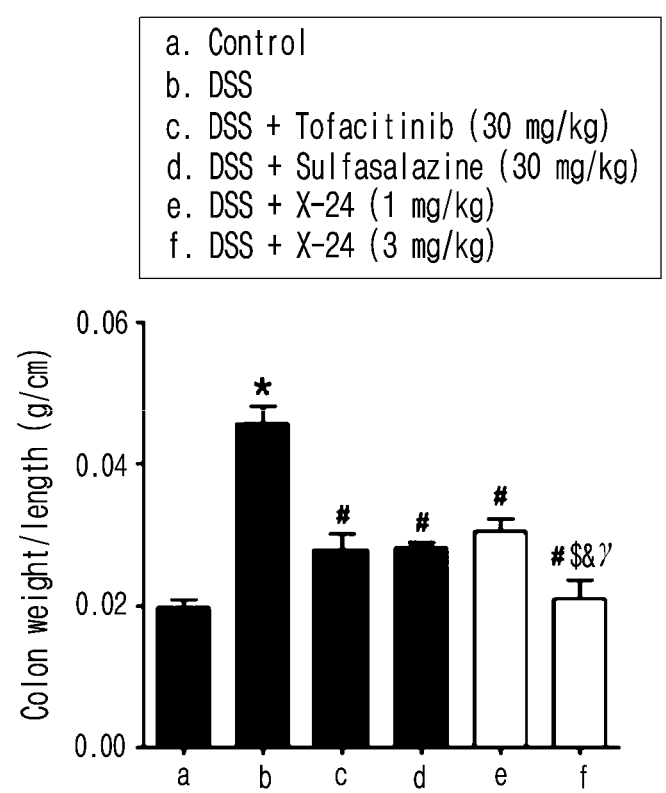
FIG. 2D is a graph showing the changes in the intestinal weight according to the treatment of the compound of the present invention in the DSS-induced chronic enteritis animal model of Experimental Example 4.

The Colon of the Mouse was Extracted and the Tissue Weight Between the anus and the cecum was measured. As a result, the weight of the colon with edema was significantly increased in the mice of the group treated with DSS alone, compared to the vehicle-treated control group mice. In the case of the chronic enteritis model, the recovery rate of intestinal tissue weight of the mice treated with 300 mg/kg of sulfasalazine or 30 mg/kg of tofacitinib, a positive control, was 67.3% and 68.8%, respectively. Compound X-24 showed dose-dependent recovery rates (58.1% and 98.2%) at 1 mg/kg and 3 mg/kg (FIG. 2D).

Figure 3D:
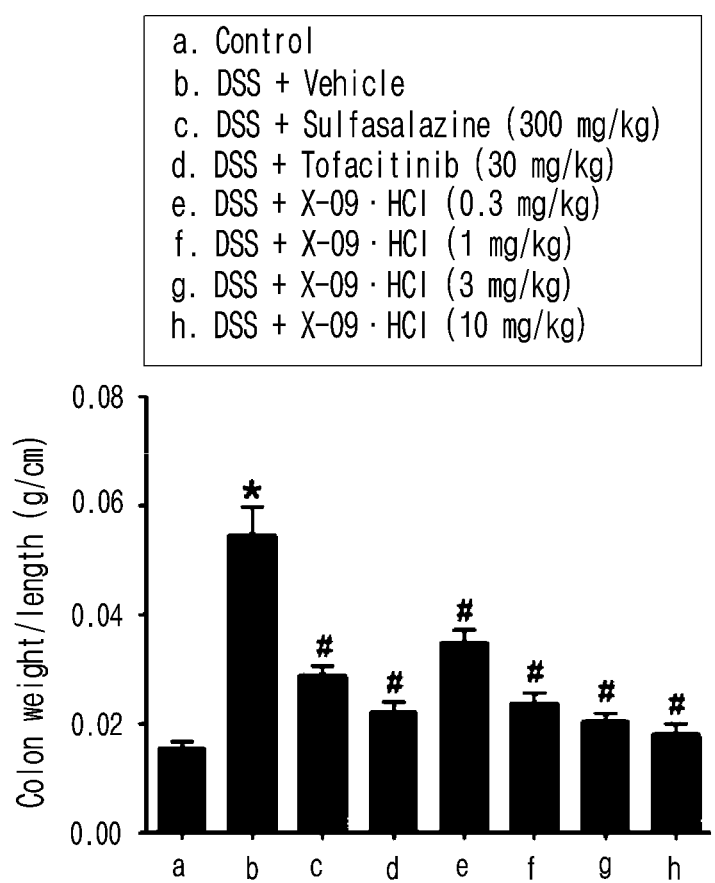
FIG. 3D is a graph showing the changes in the intestinal weight according to the treatment of the compound of the present invention in the DSS-induced acute enteritis animal model of Experimental Example 4.
Figure 3E:
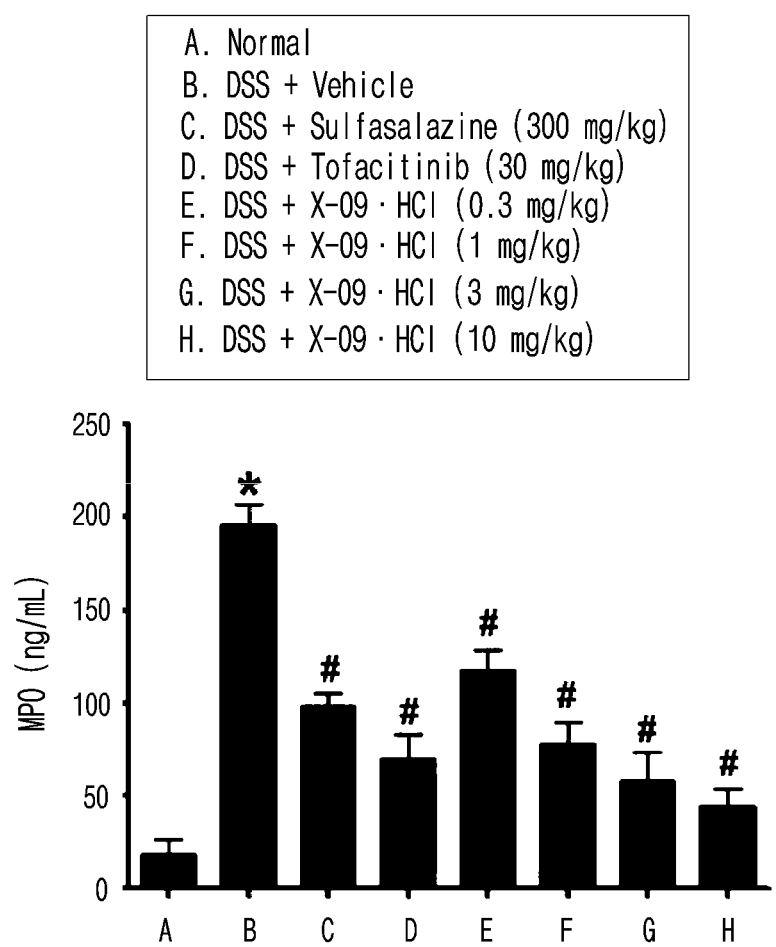
FIG. 3E is a graph showing the changes in the neutrophil marker enzyme MPO according to the treatment of the compound of the present invention in the DSS-induced acute enteritis animal model of Experimental Example 4.

The therapeutic efficacy of the compounds was measured in the acute enteritis model. As a result, the intestinal tissue weight recovery was observed in the group treated with 300 mg/kg of sulfasalazine or 30 mg/kg of tofacitinib, a positive control. Compound X-09 showed a dose-dependent effect, and exhibited a superior effect than the positive control group at 3 mg/kg and 10 mg/kg (FIG. 3D). In addition, the level of MPO, a biochemical index of tissue inflammation, was measured. As a result, the level of MPO significantly increased by DSS was decreased by compound X-09 dose-dependently, and the groups treated with the compound X-09 at the concentrations of 3 mg/kg and 10 mg/kg showed a superior effect than the positive control group (FIG. 3E).

4. Measurement of Mucosal Damage Recovery of Mouse Colon

Figure 4A:
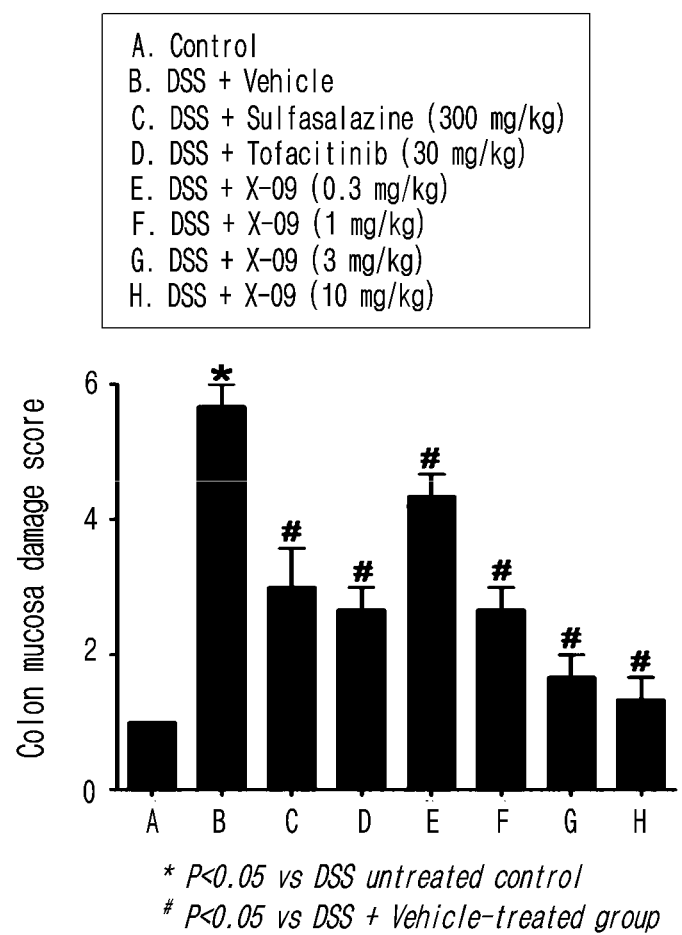
FIGS. 4A-4B are a set of diagrams showing the degree of damage of the intestinal mucosa by performing hematoxylin-eosin staining on the intestinal tissue after observing the shape of the mouse colon in the concentration-dependent efficacy measurement experiment of Experimental Example 4.
Figure 4B:
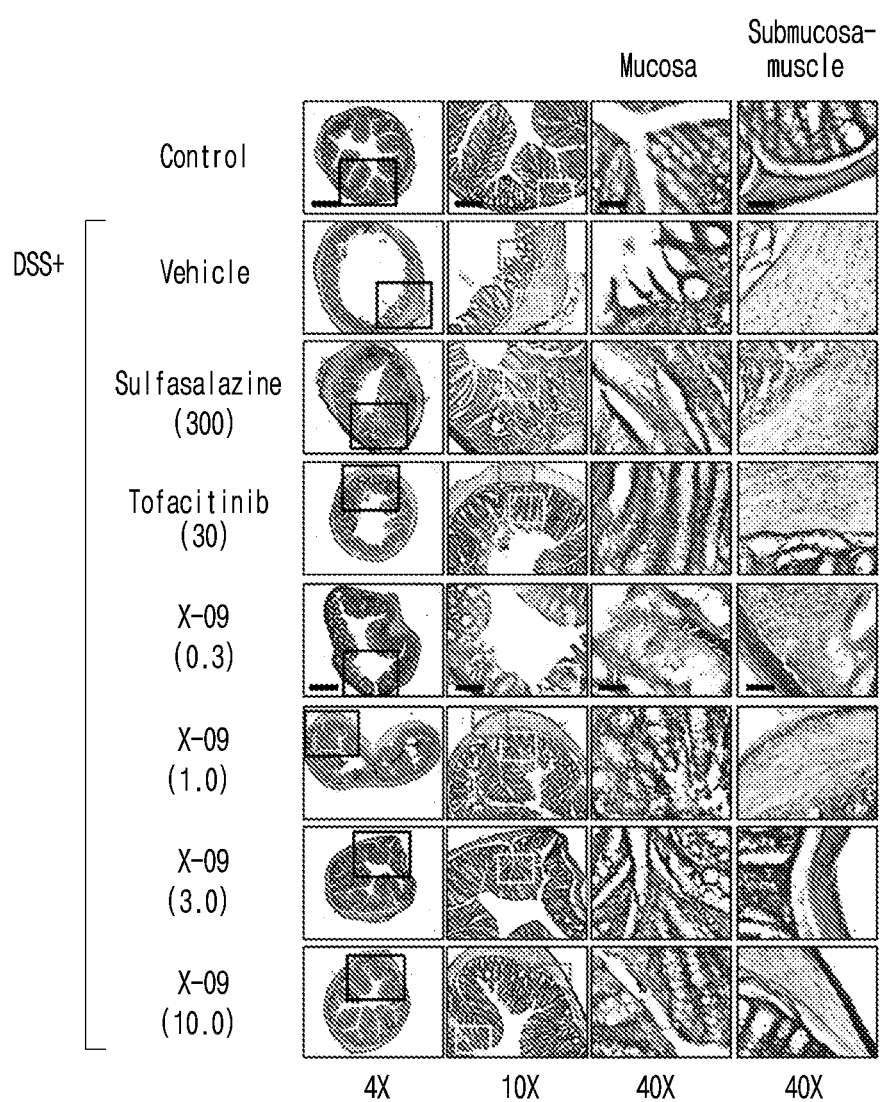

After observing the morphology of the colon in the dose-dependent activity measurement experiment, hematoxylin-eosin staining of the colon tissue was performed to score and compare the degree of colon mucosal damage. As a result, the compound X-09 showed a dose-dependent mucosal damage recovery effect, and it was confirmed that the effect was superior to that of the control group, tofacitinib (FIG. 4).

From the results of Experimental Example 4, it was confirmed that the compound represented by formula 1 of the present invention can be effectively used for the treatment of inflammatory bowel disease, and it can be seen that the compound of the present invention can be used as a substitute for existing drugs.

<Experimental Example 5> In Vivo Efficacy Test According to Oral Administration of Compounds in Collagen-Induced Rheumatoid Arthritis Animal Model <Test Method>

12-week-old normal male mice and arthritis-induced DBA/1J mice were purchased from Central Lab. Animal Inc [To induce arthritis, DBA/1J mice were sensitized by injecting a mixed solution of Complete Freund's Adjuvant (CFA; DIFCO, Detroit, MI) and Bovine Type II collagen (1:1, v/v) intradermally at the pinna base at 8 weeks of age, and then, secondary sensitization was performed by intradermal injection at the tail head at 11 weeks of age]. The purchased arthritis mice were acclimatized to the laboratory environment for a week, and then oral administration of the drug was started.

(1) Visual Observation and Measurement of Arthritis

Visual observation of arthritic lesions was performed using the following scores based on a reference (Barnett et al., 1998).

0: No edema or swelling,
1: Mild swelling and redness localized to the foot or ankle joint,
2: Mild swelling and redness from the ankle joint to the tarsal bone,
3: Moderate swelling and redness from the ankle joint to the tarsal bone,
4: Swelling, redness and joint stiffness from the ankle to the entire leg.

Therefore, the highest score for arthritic lesions was 16 per mouse. Observations were performed twice a week for 5 weeks from the day of drug administration, and the evaluation data were prepared by two people who did not know the experimental group and the control group.

In addition, photographs were taken to visually identify the degree of arthritis.

(2) Measurement of Hind Paw Thickness

The hind paw thickness, which is one of the pathological indices of rheumatoid arthritis, was measured using a caliper.

(3) Articular Tissue Staining

The right hind leg of each mouse was extracted, and all skin and muscles were removed, leaving only the bones and joints. The hind leg was fixed in 4% paraformaldehyde solution for 2 days, then immersed in 10% formic acid for 5 days to decalcify, and then immersed in 30% sucrose solution. When the tissue subsided, the articular tissue was cut into 30 m thick using a cryomicrotome (Microm HM 450, Thermo Fisher Scientific, Germany) and stored in a cryopreservation solution. Staining was performed using the stored tissue sections. After attaching the tissue sections to the slide glass, they were hydrated with 100%, 95%, 70%, and 50% ethanol solutions, and some were stained with safranin and others were stained with hematoxylin/eosin. For safranin staining, the tissue sections were first stained with 0.1% fast green solution, washed with 1% acetic acid solution, and then stained with 1% safranin solution. Thereafter, the tissue sections were dehydrated by immersing in ethanol solutions in the reverse order of hydration, and then preserved in xylene solution and mounting solution, and photographed under a microscope. Hematoxylin/eosin staining was performed in the same manner as in the colon tissue staining. The tissue sections were dehydrated, preserved in xylene solution and mounting solution, and observed under a microscope.

The degree of microscopic tissue damage of the stained articular tissue was measured using the following scores.

Grade 1: No damage on articular surface,
Grade 2: Discontinuous articular surface,
Grade 3: Vertical cracks in joint,
Grade 4: Corrosion in joint,
Grade 5: Exposure of joint erosion,
Grade 6: Joint deformity.

(4) Lymphocyte Isolation and Stimulation

After the spleen and draining lymph nodes of the mice were extracted, the number of immune cells was counted. To confirm the distribution of Th1 and Th17 cells, the immune cells obtained from each organ were stimulated using PMA/Ionomycin and Golgi stop.

After staining using an anti-IFN-γ antibody that can identify Th1 cells, an anti-IL-17 antibody that can identify Th17 cells, and an anti-CD8 antibody that can identify cytotoxic T cells, the proportion of inflammatory cells among the total immune cells was confirmed using flow cytometry.

Barnett M L, Kremer J M, St Clair E W, Clegg D O, Furst D, Weisman M, et al. Treatment of rheumatoid arthritis with oral type II collagen. Results of a multicenter, double-blind, placebo-controlled trial. Arthritis Rheum 1998; 41:290-7.

<Analysis of Effect of Oral Administration of Compound X-09 in Collagen-Induced Rheumatoid Arthritis (CIA) Animal Model>

Figure 5A:
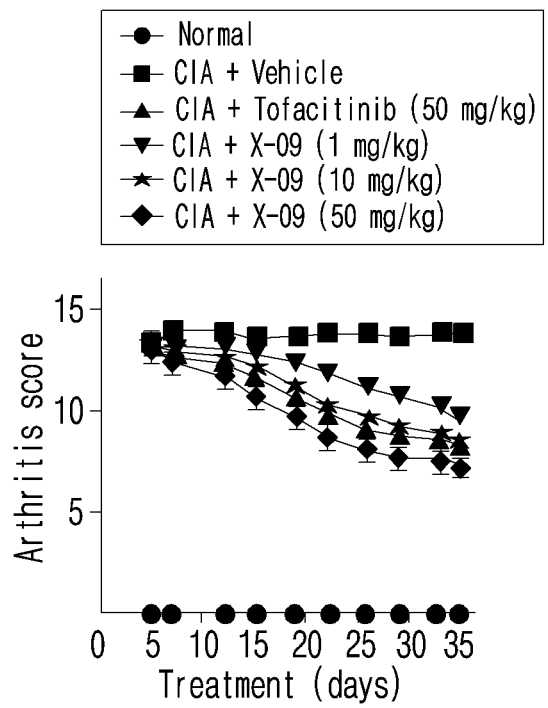
FIG. 5A is a graph showing the arthritis score according to the treatment of the compound of the present invention in the rheumatoid animal model of Experimental Example 5.
Figure 5B:
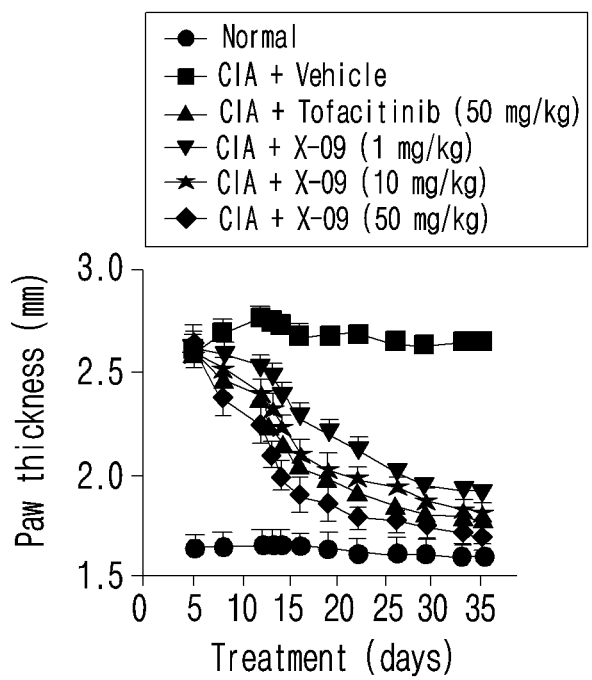
FIG. 5B is a graph showing the changes of the mouse paw thickness according to the treatment of the compound of the present invention in the rheumatoid animal model of Experimental Example 5.
Figure 5C:
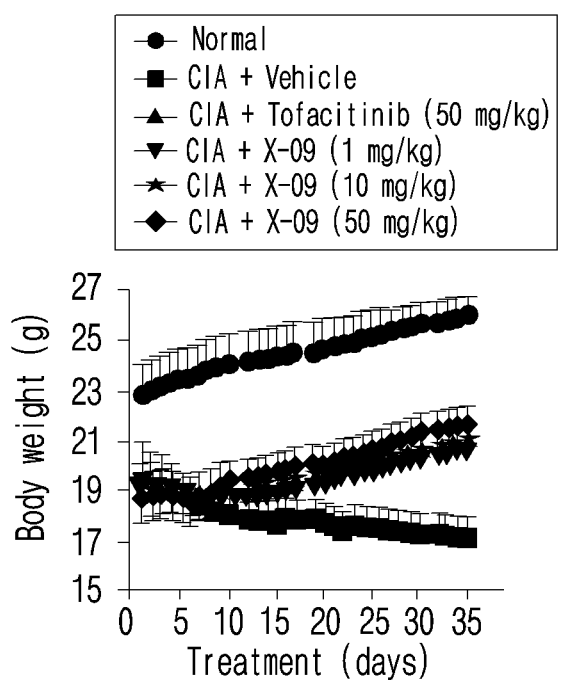
FIG. 5C is a graph showing the changes of the mouse body weight according to the treatment of the compound of the present invention in the rheumatoid animal model of Experimental Example 5.

The visual observation scores and weight changes for the degree of arthritis are shown in FIG. 5. Arthritis-induced mice exhibited an average arthritis score of 12.8 at a nearly similar level until the 4th day of drug administration. The mice in the vehicle-administered group maintained the degree of arthritis without improvement, and exhibited an arthritis index of 13.8 points on the 35th day. However, when tofacitinib or Compound X-09 was administered, the degree of arthritis was significantly improved dose dependently. On the $35^{th}$ day of drug administration, the group treated with 50 mg/kg of compound X-09 showed the best efficacy with an arthritis score of 7.2, followed by the group treated with 50 mg/kg of tofacitinib, the group treated with 10 mg/kg of compound X-09, and the group treated with 1 mg/kg of compound X-09 (FIG. 5A). The hind paw thickness of arthritic mice was 2.58 to 2.61 mm on the fourth day of drug administration, which was significantly increased compared to the average hind paw thickness of normal mice, 1.64 mm. On day $35^{th}$ day of drug administration, the hind paw thickness increased by inflammatory edema was maintained at 2.65 mm, and was significantly reduced to 1.70 mm in the group treated with 50 mg/kg of compound X-09, and the hind paw thickness was reduced in the order of the group treated with 50 mg/kg of tofacitinib, the group treated with 10 mg/kg of compound X-09, and the group treated with 1 mg/kg of compound X-09 (FIG. 5B). The body weight of the arthritis mice was significantly reduced compared to that of the normal mice of the same age, and the body weight was gradually recovered in proportion to the degree of arthritis improvement (FIG. 5C).

Figure 6:
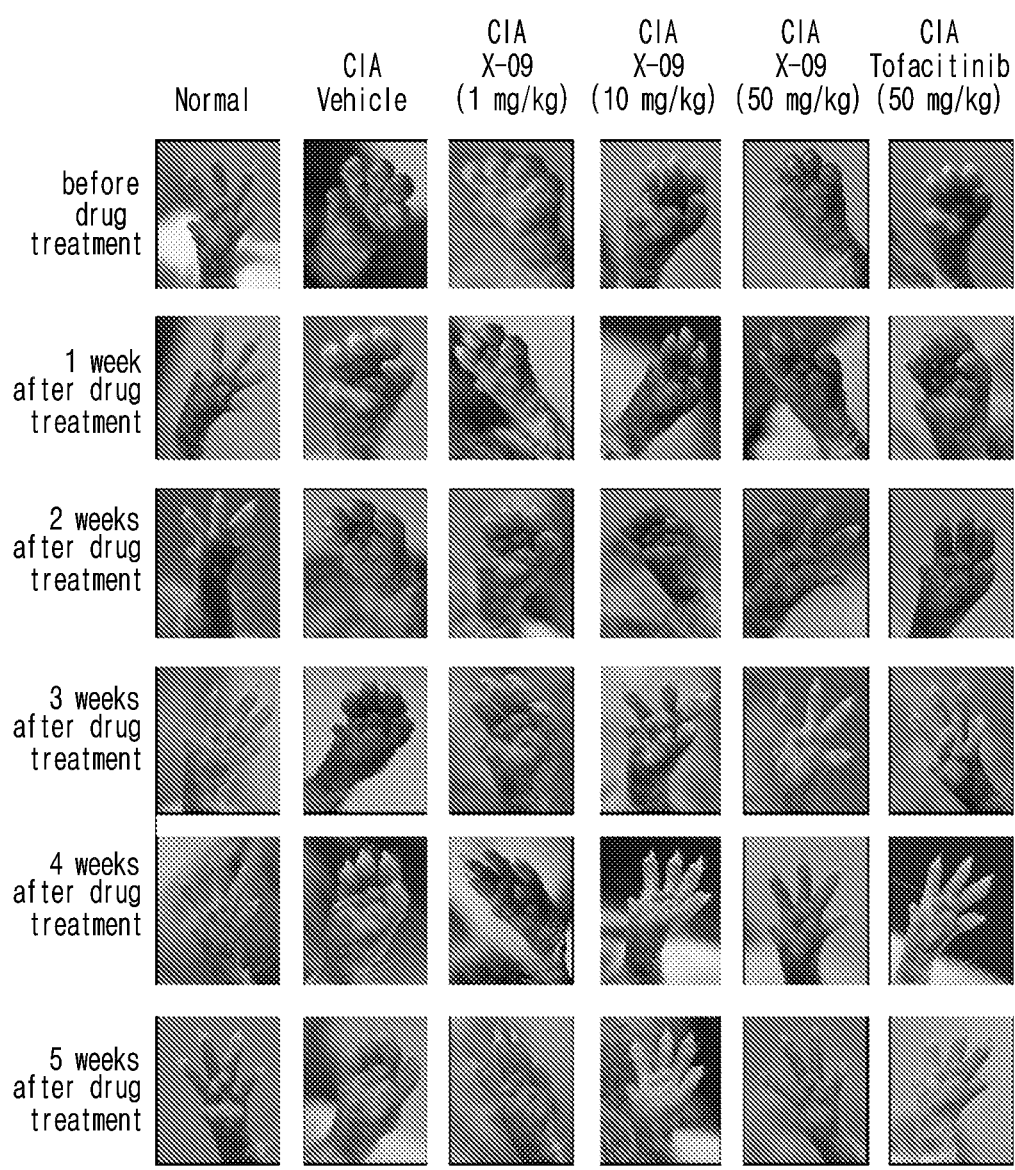
FIG. 6 is a set of photographic images showing the weekly change in the degree of arthritis according to the treatment of the compound of the present invention in the rheumatoid animal model of Experimental Example 5.
Figure 7A:
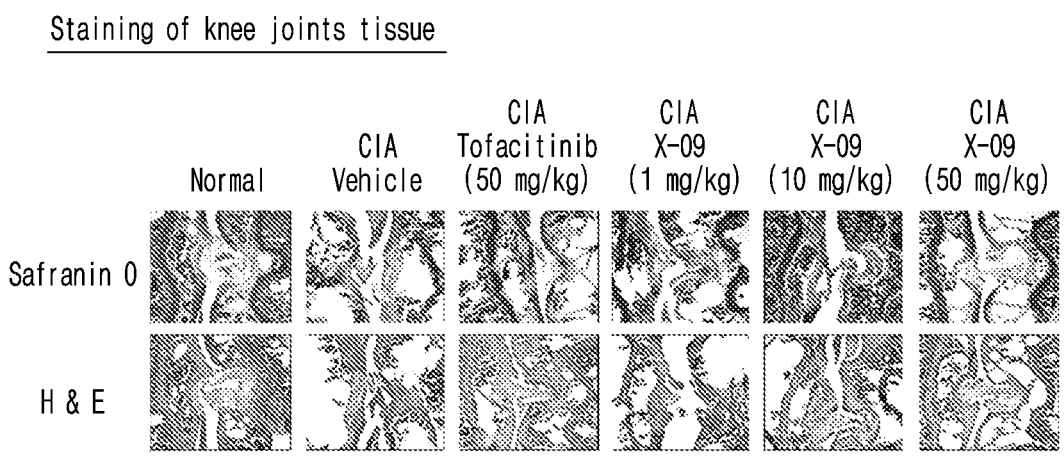
FIGS. 7A-7B are a set of images showing the degree of the articular tissue recovery according to the treatment of the compound of the present invention by hematoxylin & eosin staining and safranin O staining in the rheumatoid animal model of Experimental Example 5 in terms of scores.
Figure 7B:
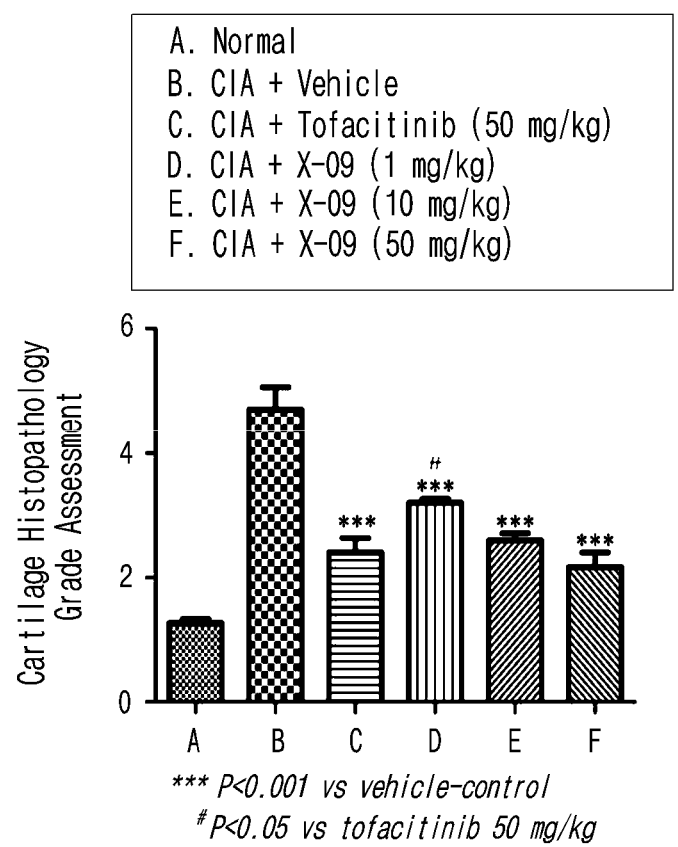

The weekly changes in the degree of arthritis of the hind paws were shown as photographic images (FIG. 6). The articular tissue was stained with hematoxylin & eosin and safranin O, and the degree of recovery of the articular tissue was converted into a score (FIG. 7).

Figure 8A:
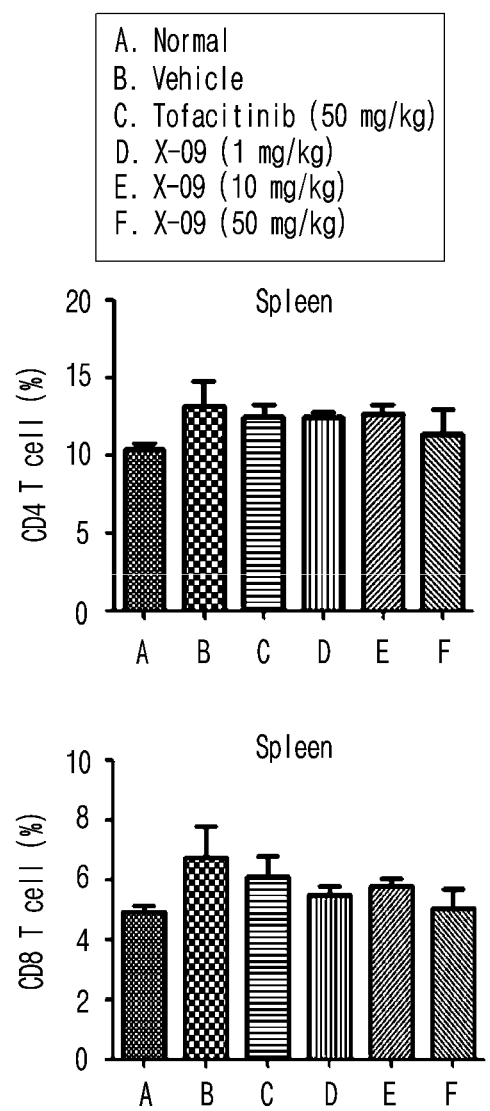
FIG. 8A is a set of graphs showing the results of analyzing the total number of immune cells in the spleen according to the treatment of the compound of the present invention in the rheumatoid animal model of Experimental Example 5.
Figure 8B:
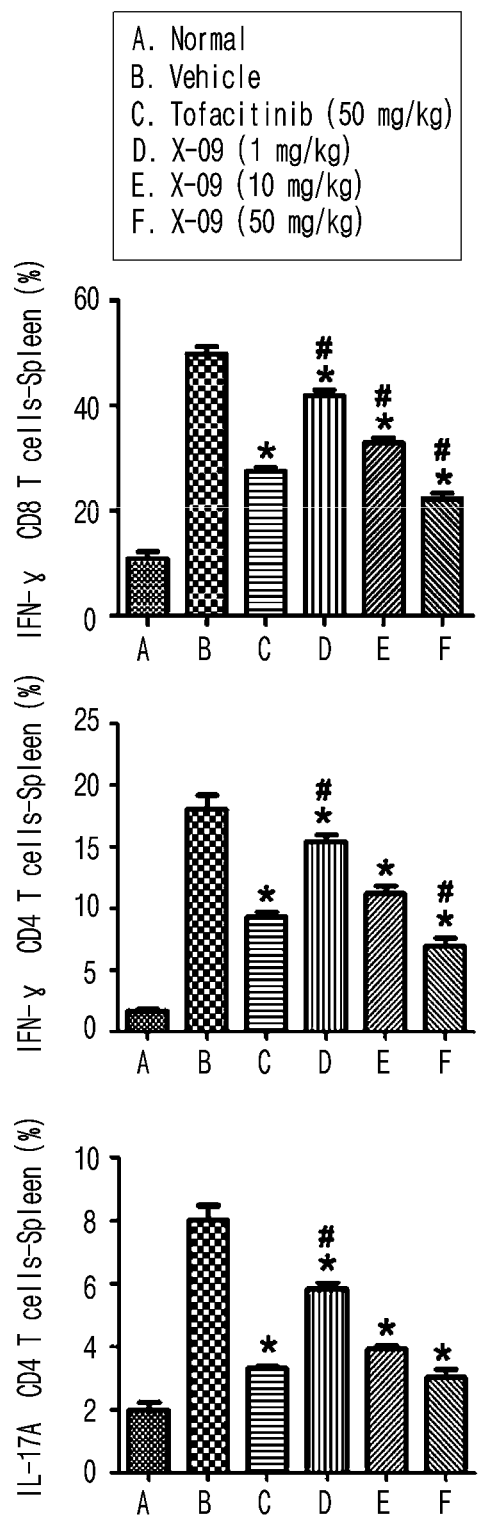
FIG. 8B is a set of graphs showing the results of analyzing the number of inflammatory cells in the spleen according to the treatment of the compound of the present invention in the rheumatoid animal model of Experimental Example 5.
Figure 8C:
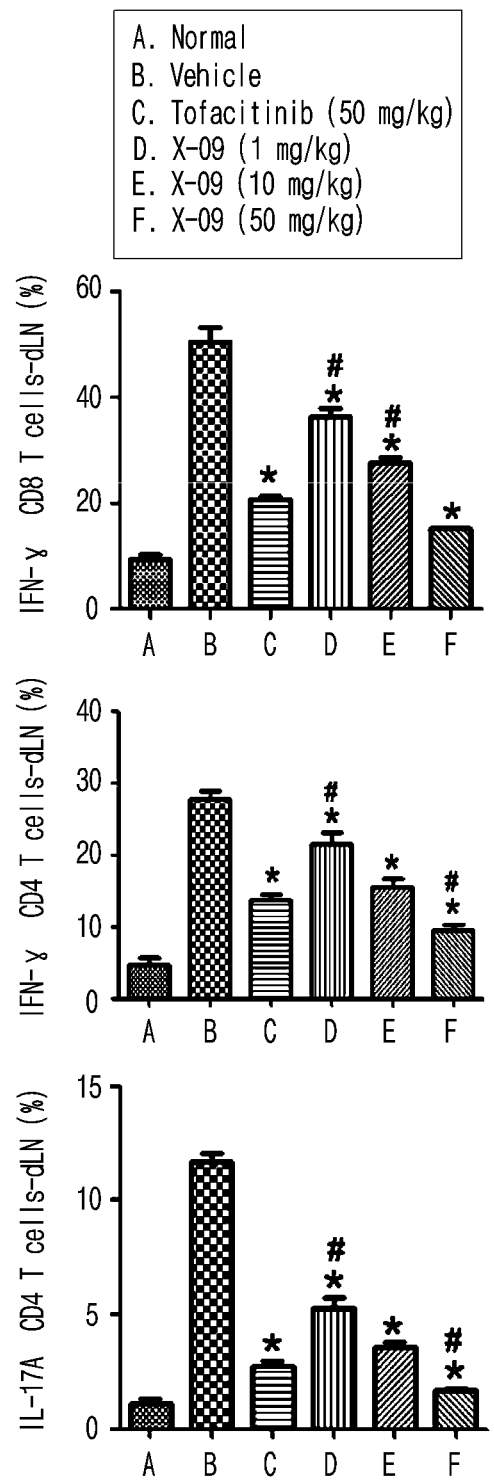
FIG. 8C is a set of graphs showing the results of analyzing the number of inflammatory cells in the draining lymph node according to the treatment of the compound of the present invention in the rheumatoid animal model of Experimental Example 5.

After 35 days of drug administration, immune cells were isolated from the spleen and draining lymph nodes and analyzed. As a result, it was confirmed that the total number of immune cells in the spleen was not significantly different from that of the normal group (FIG. 8A), but the number of inflammatory cells Th1 and Th17 and the number of activated CD8 cells were significantly reduced. From the above results, it was confirmed that the dose-dependent decrease by the compound X-09 (FIG. 8B). The number of inflammatory cells Th1 and Th17 and the number of activated CD8 cells secreting interferon gamma were also significantly reduced in the draining lymph node (FIG. 8C), and the compound X-09 showed a dose-dependent effect.

From the above results, it was confirmed that the compound represented by formula 1 of the present invention can be effectively used for the treatment of rheumatoid arthritis.

Therefore, the compounds according to the present invention can be effectively used as a pharmaceutical composition for the prevention and treatment of autoimmune diseases, in particular, inflammatory bowel disease or rheumatoid arthritis, as confirmed in the above experiments.

What is claimed is:

1. A compound represented by formula 1, or a pharmaceutically acceptable salt thereof:

[Formula 1]

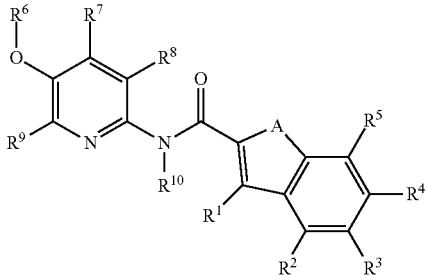

(In formula 1,

A is $NR^a$, O or S, wherein the $R^a$ is hydrogen, or straight chained or branched $C_{1-5}$ alkyl;

$R^1$, $R^2$, $R^3$, $R^4$, and $R^5$ are independently hydrogen, halogen, straight chained or branched $C_{1-5}$ alkyl, or straight chained or branched $C_{1-5}$ alkoxy, wherein the alkyl and alkoxy may be independently substituted with one or more halogens;

$R^6$ is hydrogen, straight chained or branched $C_{1-5}$ alkyl, $-(CH_2)_mC(=O)NH(CH_2)_nR^b$ or $-C(=O)R^c$, wherein the alkyl may be substituted with one or more halogens, and m and n are independently integers of 0 to 5, $R^b$ is hydrogen, straight chained or branched $C_{1-10}$ alkyl, $C_{3-10}$ cycloalkyl or $C_{6-10}$ aryl, $R^c$ is adamantanyl

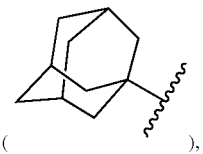

3-10 membered heterocycloalkyl with at least one N, O or S heteroatom, $C_{6-10}$ aryl, or 5-10 membered heteroaryl with at least one N, O or S heteroatom, wherein the aryl and heteroaryl may be independently substituted with at least one selected from halogen, straight chained or branched $C_{1-5}$ alkyl or straight chained or branched $C_{1-5}$ alkoxy;

$R^7$, $R^8$, and $R^9$ are independently straight chained or branched $C_{1-5}$ alkyl; and $R^{10}$ is hydrogen, or straight chained or branched $C_{1-5}$ alkyl).

2. The compound, or the pharmaceutically acceptable salt thereof, according to claim 1, wherein:

A is $NR^a$, O or S, wherein the $R^a$ is hydrogen, or straight chained or branched $C_{1-3}$ alkyl;

$R^1$, $R^2$, $R^3$, $R^4$, and $R^5$ are independently hydrogen, halogen, straight chained or branched $C_{1-3}$ alkyl, or straight chained or branched $C_{1-3}$ alkoxy, wherein the alkyl and alkoxy may be independently substituted with one or more halogens;

$R^6$ is hydrogen, straight chained or branched $C_{1-3}$ alkyl, $-(CH_2)_mC(=O)NH(CH_2)_nR^b$ or $-C(=O)R^c$, wherein the alkyl may be substituted with one or more halogens, and m and n are independently integers of 0 to 3, $R^b$ is hydrogen, straight chained or branched $C_{1-6}$ alkyl, $C_{3-8}$ cycloalkyl or phenyl, $R^c$ is adamantanyl

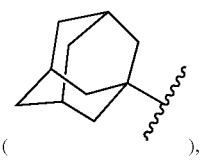

3-8 membered heterocycloalkyl with at least one N, O or S heteroatom, phenyl, or 5-6 membered heteroaryl with at least one N, O or S heteroatom, wherein the phenyl and heteroaryl may be independently substituted with at least one selected from the group consisting of halogen, straight chained or branched $C_{1-3}$ alkyl and straight chained or branched $C_{1-3}$ alkoxy;

$R^7$, $R^8$, and $R^9$ are independently straight chained or branched $C_{1-3}$ alkyl; and $R^{10}$ is hydrogen, or straight chained or branched $C_{1-3}$ alkyl.

3. The compound, or the pharmaceutically acceptable salt thereof, according to claim 1, wherein:

A is NR$^a$, O or S, wherein the R$^a$ is hydrogen or methyl;
R$^1$, R$^2$, R$^3$, R$^4$, and R$^5$ are independently hydrogen, —Cl, —Br, —F, methyl, methoxy, —CF$_3$ or —OCF$_3$;
R$^6$ is hydrogen, methyl, —(CH$_2$)mC(=O)NH(CH$_2$)nR$^b$, or —C(=O)R$^c$, wherein m is 1, and n is 0 or 1,
R$^b$ is hydrogen, straight chained or branched C$_{1-3}$ alkyl, C$_{3-6}$ cycloalkyl or phenyl,
R$^c$ is adamantanyl

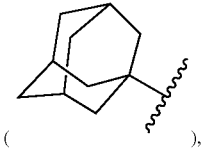 [SMILES: *C12CC3CC(CC(C3)C1)C2]

( ), 6 membered heterocycloalkyl with at least one N, O or S heteroatom, phenyl, or 6 membered heteroaryl with at least one N, O or S heteroatom, wherein the phenyl and heteroaryl may be independently substituted with at least one selected from the group consisting of halogen, and straight chained or branched C$_{1-3}$ alkoxy;
R$^7$, R$^8$, and R$^9$ are methyl; and
R$^{10}$ is hydrogen or methyl.

4. The compound, or the pharmaceutically acceptable salt thereof, according to claim 1, wherein:
R$^6$ is hydrogen, methyl, —(CH$_2$)C(=O)NHR$^b$, or —C(=O)R$^c$,
R$^b$ is hydrogen, isopropyl, cyclopropyl, cyclohexyl, phenyl or benzyl,
R$^c$ is adamantanyl

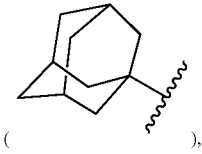 [SMILES: *C12CC3CC(CC(C3)C1)C2]

( ), morpholinyl, phenyl or pyridinyl, wherein the phenyl and pyridinyl may be independently substituted with at least one selected from the group consisting of F, Cl and methoxy.

5. The compound, or the pharmaceutically acceptable salt thereof, according to claim 1, wherein the compound represented by formula 1 is selected from the group consisting of the following compounds:

<27>N-(5-hydroxy-3,4,6-trimethylpyridin-2-yl)-1H-indole-2-carboxamide;
<28>N-(5-hydroxy-3,4,6-trimethylpyridin-2-yl)-1-methyl-1H-indole-2-carboxamide;
<29>7-bromo-N-(5-hydroxy-3,4,6-trimethylpyridin-2-yl)-1H-indole-2-carboxamide;
<30>6-chloro-N-(5-hydroxy-3,4,6-trimethylpyridin-2-yl)-1H-indole-2-carboxamide;
<31>6-bromo-N-(5-hydroxy-3,4,6-trimethylpyridin-2-yl)-1H-indole-2-carboxamide;
<32>5-fluoro-N-(5-hydroxy-3,4,6-trimethylpyridin-2-yl)-1H-indole-2-carboxamide;
<33>5-bromo-N-(5-hydroxy-3,4,6-trimethylpyridin-2-yl)-1H-indole-2-carboxamide;
<34>5-chloro-N-(5-hydroxy-3,4,6-trimethylpyridin-2-yl)-1H-indole-2-carboxamide;
<35>N-(5-hydroxy-3,4,6-trimethylpyridin-2-yl)-5-methyl-1H-indole-2-carboxamide;
<36>N-(5-hydroxy-3,4,6-trimethylpyridin-2-yl)-5-(trifluoromethyl)-1H-indole-2-carboxamide;
<37>N-(5-hydroxy-3,4,6-trimethylpyridin-2-yl)-5-(trifluoromethoxy)-1H-indole-2-carboxamide;
<38>N-(5-hydroxy-3,4,6-trimethylpyridin-2-yl)-6-methoxy-1H-indole-2-carboxamide;
<39>N-(5-hydroxy-3,4,6-trimethylpyridin-2-yl)-5-methoxy-1H-indole-2-carboxamide;
<40>N-(5-hydroxy-3,4,6-trimethylpyridin-2-yl)-5,6-dimethoxy-1H-indole-2-carboxamide;
<41>N-(5-hydroxy-3,4,6-trimethylpyridin-2-yl) benzofuran-2-carboxamide;
<42>5-chloro-N-(5-hydroxy-3,4,6-trimethylpyridin-2-yl) benzofuran-2-carboxamide;
<43>5-bromo-N-(5-hydroxy-3,4,6-trimethylpyridin-2-yl) benzofuran-2-carboxamide;
<44>N-(5-hydroxy-3,4,6-trimethylpyridin-2-yl)-7-methoxybenzofuran-2-carboxamide;
<45>N-(5-hydroxy-3,4,6-trimethylpyridin-2-yl)-3-methylbenzofuran-2-carboxamide;
<46>N-(5-hydroxy-3,4,6-trimethylpyridin-2-yl) benzo[b]thiophene-2-carboxamide;
<47>3-chloro-N-(5-hydroxy-3,4,6-trimethylpyridin-2-yl) benzo[b]thiophene-2-carboxamide;
<48>3-bromo-N-(5-hydroxy-3,4,6-trimethylpyridin-2-yl) benzo[b]thiophene-2-carboxamide;
<49>3-chloro-N-(5-hydroxy-3,4,6-trimethylpyridin-2-yl)-6-methylbenzo[b]thiophene-2-carboxamide;
<50>3-chloro-6-fluoro-N-(5-hydroxy-3,4,6-trimethylpyridin-2-yl) benzo[b]thiophene-2-carboxamide;
<51>3,6-dichloro-N-(5-hydroxy-3,4,6-trimethylpyridin-2-yl) benzo[b]thiophene-2-carboxamide;
<52>3-chloro-N-(5-hydroxy-3,4,6-trimethylpyridin-2-yl)-6-methoxybenzo[b]thiophene-2-carboxamide;
<53>3-chloro-6-fluoro-N-(5-methoxy-3,4,6-trimethylpyridin-2-yl) benzo[b]thiophene-2-carboxamide;
<54>3-chloro-6-fluoro-N-(5-methoxy-3,4,6-trimethylpyridin-2-yl)-N-methylbenzo[b]thiophene-2-carboxamide;
<55>3-chloro-6-fluoro-N-(5-(2-(isopropylamino)-2-oxoethoxy)-3,4,6-trimethylpyridin-2-yl) benzo[b]thiophene-2-carboxamide;
<56>3-chloro-N-(5-(2-(cyclopropylamino)-2-oxoethoxy)-3,4,6-trimethylpyridin-2-yl)-6-fluorobenzo[b]thiophene-2-carboxamide;
<57>3-chloro-N-(5-(2-(cyclohexylamino)-2-oxoethoxy)-3,4,6-trimethylpyridin-2-yl)-6-fluorobenzo[b]thiophene-2-carboxamide;
<58>N-(5-(2-(benzylamino)-2-oxoethoxy)-3,4,6-trimethylpyridin-2-yl)-3-chloro-6-fluorobenzo[b]thiophene-2-carboxamide;
<59>3-chloro-6-fluoro-N-(3,4,6-trimethyl-5-(2-oxo-2-(phenylamino) ethoxy) pyridin-2-yl) benzo[b]thiophene-2-carboxamide;
<60>6-(3-chloro-6-fluorobenzo[b]thiophene-2-carboxamido)-2,4,5-trimethylpyridin-3-yl benzoate;
<61>6-(3-chloro-6-fluorobenzo[b]thiophene-2-carboxamido)-2,4,5-trimethylpyridin-3-yl 4-fluorobenzoate;
<62>6-(3-chloro-6-fluorobenzo[b]thiophene-2-carboxamido)-2,4,5-trimethylpyridin-3-yl 3-methoxybenzoate;
<63>6-(3-chloro-6-fluorobenzo[b]thiophene-2-carboxamido)-2,4,5-trimethylpyridin-3-yl 4-methoxybenzoate;

<64> 6-(3-chloro-6-fluorobenzo [b]thiophene-2-carbox-amido)-2,4,5-trimethylpyridin-3-yl 5-fluoropicolinate;
<65> 6-(3-chloro-6-fluorobenzo [b]thiophene-2-carbox-amido)-2,4,5-trimethylpyridin-3-yl 6-fluoronicotinate;
<66> 6-(3-chloro-6-fluorobenzo [b]thiophene-2-carbox-amido)-2,4,5-trimethylpyridin-3-yl 5-chloropicolinate;
<67> 6-(3-chloro-6-fluorobenzo [b]thiophene-2-carbox-amido)-2,4,5-trimethylpyridin-3-yl 6-chloropicolinate;
<68> 6-(3-chloro-6-fluorobenzo [b]thiophene-2-carbox-amido)-2,4,5-trimethylpyridin-3-yl (3r,5r,7r)-adamantane-1-carboxylate;
<69> 6-(3-chloro-6-fluorobenzo [b]thiophene-2-carbox-amido)-2,4,5-trimethylpyridin-3-yl morpholine-4-carboxylate.

6. A method for preparing a compound represented by formula 1 comprising a step of preparing a compound represented by formula 1 by reacting a compound represented by formula 2 with a compound represented by formula 3, as shown in reaction formula 1 below:

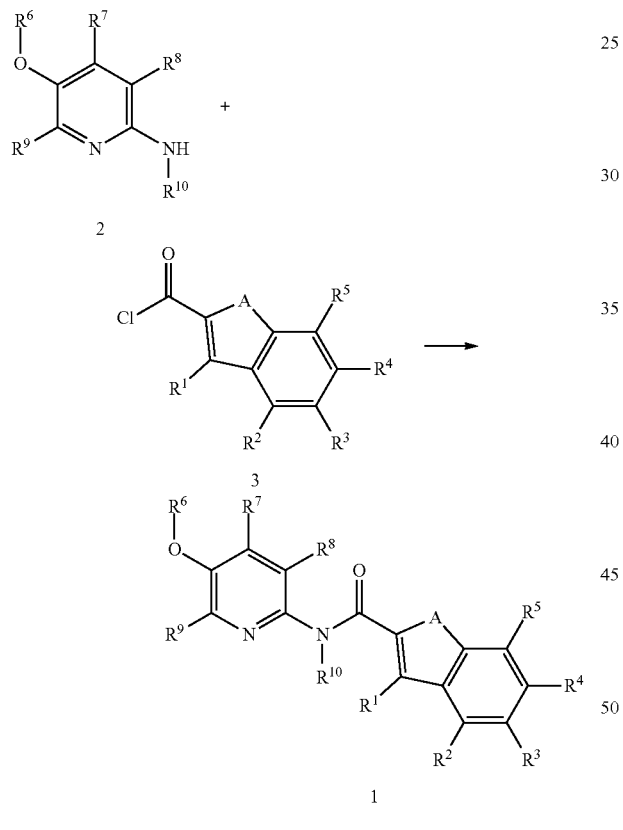

(In reaction formula 1,
A, $R^1$, $R^2$, $R^3$, $R^4$, $R^5$, $R^6$, $R^7$, $R^8$, $R^9$, and $R^{10}$ are as defined in formula 1 of claim 1).

7. A method for preparing a compound represented by formula 1b comprising the following steps, as shown in reaction formula 2 below:
preparing a compound represented by formula 4 by reacting a compound represented by formula 2a with a compound represented by formula 3 (step 1);
preparing a compound represented by formula 1a by deprotecting the compound represented by formula 4 obtained in step 1 above (step 2); and
preparing a compound represented by formula 1b by reacting the compound represented by formula 1a obtained in step 2 above with a compound represented by formula 5 (step 3):

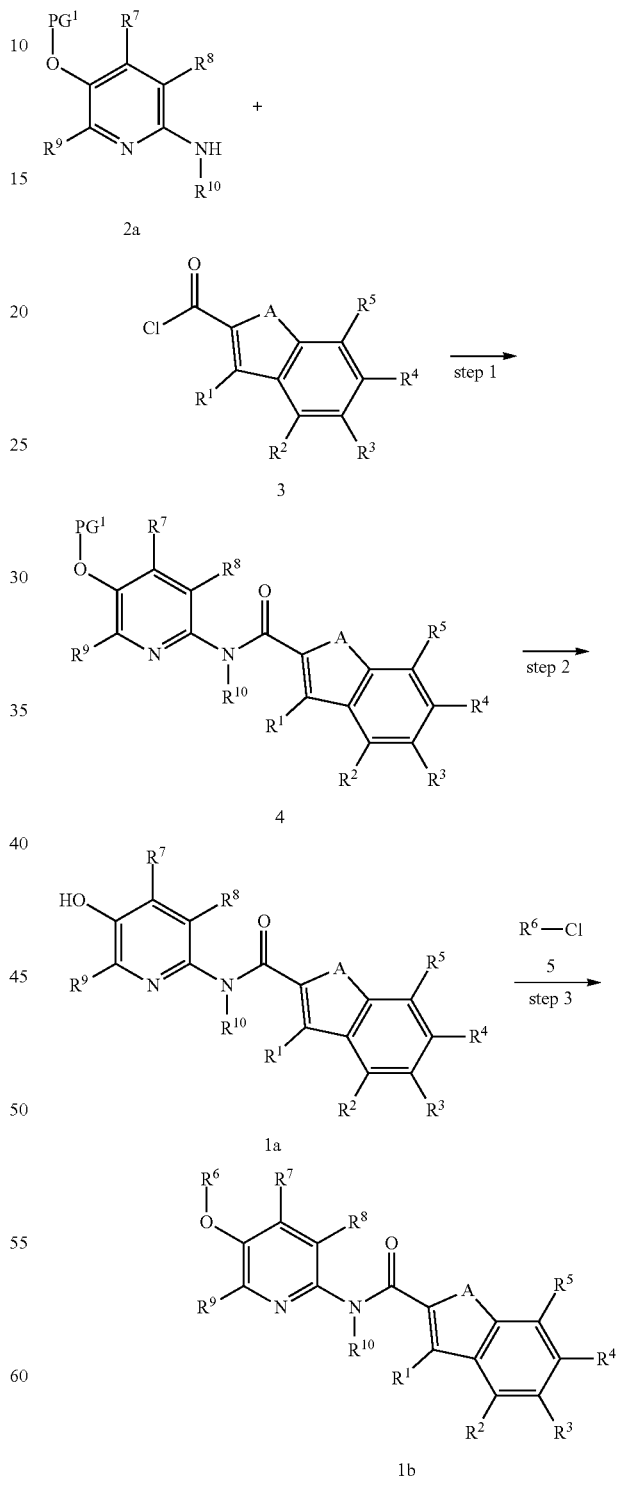

(In reaction formula 2,

A, $R^1$, $R^2$, $R^3$, $R^4$, $R^5$, $R^7$, $R^8$, $R^9$, and $R^{10}$ are as defined in formula 1 of claim 1;

$R^6$ is straight chained or branched $C_{1-5}$ alkyl, —$(CH_2)mC(=O)NH(CH_2)nR^b$ or —$C(=O)R^c$, wherein the alkyl may be substituted with one or more halogens, and m and n are independently integers of 0 to 5;

$PG^1$ is an alcohol protecting group selected from the group consisting of acetyl (Ac), benzoyl (Bz), benzyl (Bn), methylthiomethyl ether, MEM (β-methoxyethoxymethyl ether), DMT (dimethoxytrityl, [bis-(4-methoxyphenyl) phenylmethyl]), MOM (methoxymethyl ether), MMT (methoxytrityl [(4-methoxyphenyl) diphenylmethyl]), PMP (p-methoxybenzyl ether), Piv (pivaloyl), THP (tetrahydropyranyl), THF (tetrahydrofuran) and Trityl (triphenylmethyl, Tr); and X is halogen).

8. A method for treating inflammatory bowel disease comprising administering a compound represented by formula 1 of claim 1, or a pharmaceutically acceptable salt thereof, to a subject in need thereof.

9. The method for treating inflammatory bowel disease according to claim 8, wherein the compound inhibits the adhesion of monocytes to intestinal epithelial cells by TNF-α or IL-6.

10. The method for treating inflammatory bowel disease according to claim 8, wherein the inflammatory bowel disease is at least one selected from the group consisting of enteritis, colitis, ulcerative enteritis, Crohn's disease, Crohn's cytoma, irritable bowel syndrome, hemorrhagic rectal ulcer, pouchitis, peptic ulcer, intestinal Behcet's disease and gastritis.

11. A pharmaceutical composition comprising a compound represented by formula 1 of claim 1, or a pharmaceutically acceptable salt thereof; and a pharmaceutically acceptable excipient.

* * * * *